(12) United States Patent
Bell et al.

(10) Patent No.: US 7,851,464 B2
(45) Date of Patent: Dec. 14, 2010

(54) SPIROLACTAM ARYL CGRP RECEPTOR ANTAGONISTS

(75) Inventors: Ian M. Bell, Harleysville, PA (US); Harold G. Selnick, Ambler, PA (US); Michael R. Wood, Harleysville, PA (US); Cory R. Theberge, King of Prussia, PA (US); Craig A. Stump, Pottstown, PA (US); Steven N. Gallicchio, Wyndmoor, PA (US); C. Blair Zartman, Hatfield, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 142 days.

(21) Appl. No.: 12/085,057

(22) PCT Filed: Nov. 14, 2006

(86) PCT No.: PCT/US2006/044088

§ 371 (c)(1),
(2), (4) Date: May 14, 2008

(87) PCT Pub. No.: WO2007/061677

PCT Pub. Date: May 31, 2007

(65) Prior Publication Data

US 2009/0247514 A1    Oct. 1, 2009

Related U.S. Application Data

(60) Provisional application No. 60/737,976, filed on Nov. 18, 2005.

(51) Int. Cl.
| | | |
|---|---|---|
| A61K 31/437 | (2006.01) | |
| A61K 31/4375 | (2006.01) | |
| A61K 31/438 | (2006.01) | |
| A61K 31/4985 | (2006.01) | |
| A61K 31/551 | (2006.01) | |
| C07D 243/10 | (2006.01) | |
| C07D 487/22 | (2006.01) | |
| C07D 471/22 | (2006.01) | |
| C07D 241/38 | (2006.01) | |
| C07D 401/14 | (2006.01) | |

(52) U.S. Cl. .................... 514/219; 514/278; 514/250; 544/233; 540/555; 546/18

(58) Field of Classification Search .................. None
See application file for complete search history.

(56) References Cited

U.S. PATENT DOCUMENTS

| 5,436,261 | A | 7/1995 | Cordi et al. |
|---|---|---|---|
| 6,344,449 | B1 | 2/2002 | Rudolf et al. |
| 6,953,790 | B2 | 10/2005 | Burgey et al. |
| 7,189,722 | B2 | 3/2007 | Bell et al. |
| 7,192,954 | B2 | 3/2007 | Bell et al. |
| 7,202,251 | B2 | 4/2007 | Bell et al. |
| 7,384,930 | B2 | 6/2008 | Chaturvedula et al. |
| 7,384,931 | B2 | 6/2008 | Chaturvedula et al. |
| 2003/0139417 | A1 | 7/2003 | Eberlein et al. |
| 2004/0204397 | A1 | 10/2004 | Chaturvedula et al. |
| 2005/0234054 | A1* | 10/2005 | Mueller et al. ........... 514/229.8 |
| 2007/0293470 | A1 | 12/2007 | Williams et al. |
| 2008/0004304 | A1 | 1/2008 | Bell et al. |
| 2008/0096878 | A1 | 4/2008 | Bell et al. |

FOREIGN PATENT DOCUMENTS

| WO | 2004/082602 A2 | 9/2004 |
|---|---|---|
| WO | 2004/082678 A2 | 9/2004 |
| WO | WO 2004/087649 A2 | 10/2004 |
| WO | 2006/031513 A2 | 3/2006 |
| WO | 2006/031606 A2 | 3/2006 |
| WO | WO 2006/029153 A2 | 3/2006 |
| WO | WO 2006/031491 A2 | 3/2006 |
| WO | WO 2006/031676 A2 | 3/2006 |
| WO | WO 2006/052378 A1 | 5/2006 |
| WO | WO 2007/061676 A2 | 5/2007 |
| WO | WO 2007/061692 A2 | 5/2007 |
| WO | WO 2007/061694 A2 | 5/2007 |
| WO | WO 2007/061695 A2 | 5/2007 |
| WO | WO 2007/061696 A2 | 5/2007 |

OTHER PUBLICATIONS

Bioorg. Med. Chem. Lett. 19:4742 (2009).*
Bioorg. Med. Chem. Lett. 19:5787 (2009).*
Supplementary Search Report and Opinion for Counterpart European Patent Application No. EP 06 83 7498 (Sep. 24, 2010).

* cited by examiner

*Primary Examiner*—Kamal A Saeed
*Assistant Examiner*—Michael Barker
(74) *Attorney, Agent, or Firm*—Gerard Devlin; Raynard Yuro

(57) ABSTRACT

Compounds of formula I:

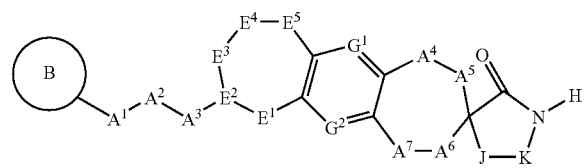

(wherein variables $A^1$, $A^2$, $A^3$, $A^4$, $A^5$, $A^6$, $A^7$, $E^1$, $E^2$, $E^3$, $E^4$, $E^5$, $G^1$, $G^2$, J and K are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

17 Claims, No Drawings

SPIROLACTAM ARYL CGRP RECEPTOR ANTAGONISTS

CROSS-REFERENCE TO RELATED APPLICATIONS

This application claims priority under 35 U.S.C. §119(e) of U.S. provisional application Ser. No. 60/737,976, filed Nov. 18, 2005.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-elated Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, asthma (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of the formula I:

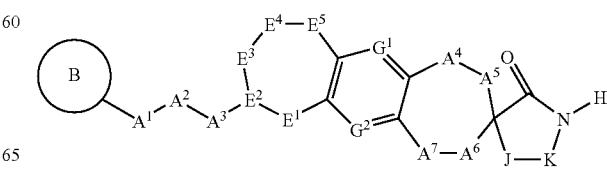

(wherein variables $A^1, A^2, A^3, A^4, A^5, A^6, A^7, E^1, E^2, E^3, E^4, E^5, G^1, G^2$, J and K are as described herein) which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

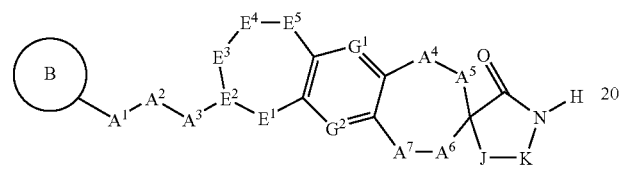

wherein:
B is a selected from:
C$_{3-10}$cycloalkyl, phenyl, naphthyl, tetrahydronaphtliyl, indanyl, biphenyl, phenanthryl, anthryl, azepanyl, azepinyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indazolyl, indolinyl, indolyl, isochromanyl, isoindolinyl, isoquinolinyl, isoxazolyl, isoxazolinyl, isoxazolidinyl, isothiazolidinyl, isothiazolyl, morpholinyl, naphthyridinyl, oxadiazolyl, oxazolyl, oxazolinyl, oxazolidinyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, phthalazinyl, piperidyl, piperazinyl, pyrazinyl, pyrazolidinyl, pyrazolyl, pyridazinyl, pyridinyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, thienyl, triazolyl and triazolinyl,
where B is linked to A$^1$ via a carbon atom in B and
where B is unsubstituted or substituted with 1-5 substituents independently selected from R$^1$,
R$^2$, R$^{3a}$ and R$^{3b}$, wherein
R$^1$, R$^2$, R$^{3a}$ and R$^{3b}$ are each independently selected from:
(1) —C$_{1-6}$alkyl, which is unsubstituted or substituted with 1-7 substituents each independently selected from:
 (a) halo,
 (b) hydroxy,
 (c) —O—C$_{1-6}$alkyl, which is unsubstituted or substituted with 1-5 halo,
 (d) —C$_{3-6}$cycloalkyl,
 (e) phenyl or heterocycle, wherein heterocycle is selected from: azetidinyl, imidazolyl, oxazolyl, pyridinyl, pyrimidinyl, pyrazinyl, pyridazinyl, piperidinyl, azepanyl, azepinyl, piperazinyl, pyrazolyl, pyrrolidinyl, thiazolyl, thienyl, triazolyl, tetrazolyl, tetrahydrofuryl and morpholinyl,
which phenyl or heterocycle is unsubstituted or substituted with 1-5 substituents each independently selected from:
 (i) —C$_{1-6}$alkyl, which is unsubstituted or substituted with 1-5 halo,
 (ii) —O—C$_{1-6}$alkyl, which is unsubstituted or substituted with 1-5 halo,
 (iii) halo,
 (iv) hydroxy,
 (v) trifluoromethyl,
 (vi) —OCF$_3$,
 (vii) oxo,
 (viii) amino,
 (ix) phenyl, and
 (x) benzyl,
(f) —CO$_2$R$^9$, wherein R$^9$ is independently selected from:
 (i) hydrogen,
 (ii) —C$_{1-6}$alkyl, which is unsubstituted or substituted with 1-6 substituents, substituents each independently selected from:
  (I) halo,
  (II) hydroxy,
  (III) —O—C$_{1-6}$alkyl, which is unsubstituted or substituted with 1-5 halo,
  (IV) —C$_{3-6}$cycloalkyl,
  (V) phenyl, which is unsubstituted or substituted with 1-5 substituents each independently selected from:
   (1) —C$_{1-4}$alkyl,
   (2) —O—C$_{1-6}$alkyl,
   (3) halo,
   (4) trifluoromethyl, and
   (5) —OCF$_3$,
 (iii) —C$_{3-6}$cycloalkyl, which is unsubstituted or substituted with 1-6 substituents, substituents each independently selected from:
  (I) halo,
  (II) hydroxy,
  (III) —O—C$_{1-6}$alkyl, which is unsubstituted or substituted with 1-5 halo,
  (IV) —C$_{1-6}$alkyl, which is unsubstituted or substituted with 1-5 halo, and
  (V) phenyl, and
 (iv) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:
  (I) halo,
  (II) —C$_{1-6}$alkyl, which is unsubstituted or substituted with 1-5 halo
  (III) —O—C$_{1-6}$alkyl, which is unsubstituted or substituted with 1-5 halo
  (IV) —C$_{3-6}$cycloalkyl,
  (V) oxo,
  (VI) —CN,
  (VII) hydroxy, and
  (VIII) phenyl, (g) —NR$^{10}$R$^{11}$, wherein R$^{10}$ and R$^{11}$ are each independently selected from:
  (i) hydrogen,
  (ii) —C$_{1-6}$alkyl, which is unsubstituted or substituted with 1-6 substituents each independently selected from:
    (I) —O—C$_{1-6}$alkyl, which is unsubstituted or substituted with 1-5 halo,
    (II) halo,
    (III) hydroxy,
    (IV) —OCF$_3$,
    (V) —C$_{3-6}$cycloalkyl, and
    (VI) phenyl,
  (iii) —C$_{4-6}$cycloalkyl,
  (iv) phenyl, which is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo,
    (IV) hydroxy,
    (V) trifluoromethyl,
    (VI) —OCF$_3$, and
    (VII) CN, and
  (v) benzyl, which is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (II) halo, and
    (IV) trifluoromethyl,
  (vi) —COR$^9$, and
  (vii) —SO$_2$R$^{12}$,
(h) —SO$_2$R$^{12}$, wherein R$^{12}$ is selected from:
  (i) —C$_{1-6}$alkyl, which is unsubstituted or substituted with 1-6 fluoro,
  (ii) —C$_{3-6}$cycloalkyl,
  (iii) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl,
    which phenyl or heterocycle is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo,
    (IV) hydroxy,
    (V) trifluoromethyl,
    (VI) —OCF$_3$, and
    (VII) CN, and
  (iv) benzyl, which is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo, and
    (IV) trifluoromethyl,
(i) —CONR$^{10a}$R$^{11a}$, wherein R$^{10a}$ and R$^{11a}$ are each independently selected from:
  (i) hydrogen,
  (ii) —C$_{1-6}$alkyl, which is unsubstituted or substituted with 1-6 substituents each independently selected from:
    (I) —O—C$_{1-6}$alkyl, which is unsubstituted or substituted with 1-5 halo,
    (II) halo,
    (III) hydroxy,
    (IV) —OCF$_3$,
    (V) —C$_{3-6}$cycloalkyl, and
    (VI) phenyl,
  (iii) —C$_{5-6}$cycloalkyl, which is unsubstituted or substituted with 1-5 halo,
  (iv) phenyl, which is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo,
    (IV) hydroxy,
    (V) trifluoromethyl,
    (VI) —OCF$_3$, and
    (VII) CN, and
  (v) benzyl, which is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo, and
    (IV) trifluoromethyl,
  or where R$^{10a}$ and R$^{11a}$ join to form a ring selected from azetidinyl, pyrrolidinyl, piperidinyl, azepanyl, piperazinyl and morpholinyl, which ring is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo
    (IV) hydroxy
    (V) phenyl, which is unsubstituted or substituted with 1-5 substituents each independently selected from:
      (1) —C$_{1-4}$alkyl, which is unsubstituted or substituted with 1-3 halo,
      (2) —O—C$_{1-4}$alkyl, which is unsubstituted or substituted with 1-3 halo, and
      (3) halo,
    (VI) benzyl, which is unsubstituted or substituted with 1-5 substituents each independently selected from:
      (1) —C$_{1-4}$alkyl, which is unsubstituted or substituted with 1-3 halo,
      (2) —O—C$_{1-4}$alkyl, which is unsubstituted or substituted with 1-3 halo, and
      (3) halo,
    (VII) —COR$^9$, and
    (VIII) —SO$_2$R$^{12}$,
(j) trifluoromethyl,
(k) —OCO$_2$R$^9$,
(l) —(NR$^{10a}$)CO$_2$R$^9$,
(m) —O(CO)NR$^{10a}$R$^{11a}$, (n) —(NR$^9$)(CO)NR$^{10a}$R$^{11a}$,
(o) —SO$_2$NR$^{10a}$R$^{11a}$, and
(p) —O—C$_{3-6}$cycloalkyl,
(2) —C$_{3-6}$cycloalkyl, which is unsubstituted or substituted with 1-7 substituents each independently selected from:
  (a) halo,
  (b) hydroxy,
  (c) —C$_{1-6}$alkyl, which is unsubstituted or substituted with 1-5 halo,
  (d) —O—C$_{1-6}$alkyl, which is unsubstituted or substituted with 1-5 halo,
  (e) phenyl, which is unsubstituted or substituted with 1-5 substituents each independently selected from:
    (i) —C$_{1-6}$alkyl, which is unsubstituted or substituted with 1-5 halo,
    (ii) —O—C$_{1-6}$alkyl, which is unsubstituted or substituted with 1-5 halo,
    (iii) halo,
    (iv) hydroxy, and
    (v) trifluoromethyl,
(3) phenyl or heterocycle, wherein heterocycle is selected from: pyridinyl, pyrimidinyl, pyrazinyl, thienyl, pyridazinyl, pyrrolidinyl, azetidinyl, azepanyl, thiazolyl, isothiazolyl, oxazolyl, isoxazolyl, imidazolyl, triazolyl, tetrazolyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, 1,3-dioxolanyl, oxadiazolyl, piperidinyl, tetrahydropyranyl, tetrahydrothienyl, tetrahydrothiopyranyl, and morpholinyl, which phenyl or heterocycle is unsubstituted or substituted with 1-5 substituents each independently selected from:
  (a) —C$_{1-6}$alkyl, which is unsubstituted or substituted with 1-5 substituents each independently selected from:
    (a) halo,
    (b) hydroxy,
    (c) —O—C$_{1-6}$alkyl, which is unsubstituted or substituted with 1-5 halo,
    (d) —C$_{3-6}$cycloalkyl,
    (e) phenyl,
    (f) —CO$_2$R$^9$, and
    (g) —NR$^{10}$R$^{11}$,
  (b) halo,
  (c) hydroxy,
  (d) —O—C$_{1-6}$alkyl, which is unsubstituted or substituted with 1-6 halo,
  (e) —C$_{3-6}$cycloalkyl,
  (f) phenyl or heterocycle, wherein heterocycle is selected from: pyrrolidinyl, piperidinyl, piperazinyl, pyridinyl, pyrimidinyl, pyrazinyl, thienyl and morpholinyl, which phenyl or heterocycle is unsubstituted or substituted with 1-5 substituents each independently selected from:
    (i) —C$_{1-6}$allyl,
    (ii) —O—C$_{1-6}$alkyl,
    (iii) halo,
    (iv) hydroxy, and
    (v) trifluoromethyl,
  (g) —CO$_2$R$^9$,
  (h) —(CO)R$^9$,
  (i) —NR$^{10}$R$^{11}$,
  (j) —CONR$^{10a}$R$^{11a}$,
  (k) oxo
  (l) —SR$^{12}$,
  (m) —S(O)R$^{12}$,
  (n) —SO$_2$R$^{12}$,
  (o) —SO$_2$NR$^{10a}$R$^{11a}$, and
  (p) —CN,
(4) halo,
(5) oxo,
(6) hydroxy,
(7) —O—C$_{1-6}$alkyl, which is unsubstituted or substituted with 1-5 substituents each independently selected from:
  (a) halo,
  (b) hydroxy,
  (c) —C$_{3-6}$cycloalkyl,
  (d) phenyl,
  (e) —CO$_2$R$^9$, and
  (f) —NR$^{10}$R$^{11}$,
(8) —CN,
(9) —CO$_2$R$^9$,
(10) —NR$^{10}$R$^{11}$,
(11) —SR$^{12}$,
(12) —S(O)R$^{12}$,
(13) —SO$_2$R$^{12}$,
(14) —SO$_2$NR$^{10a}$R$^{11a}$,
(15) —CONR$^{10a}$R$^{11a}$,
(16) —OCO$_2$R$^9$,
(17) —(NR$^{10a}$)CO$_2$R$^9$,
(18) —O(CO)NR$^{10a}$R$^{11a}$,
(19) —(NR$^9$)(CO)NR$^{10a}$R$^{11a}$,
(20) —(CO)—(CO)NR$^{10a}$R$^{11a}$, and
(21) —(CO)—(CO)OR$^9$;
or where R$^{3a}$ and R$^{3b}$ and the atom(s) to which they are attached join to form a ring selected from cyclobutyl, cyclopentyl, cyclohexyl, cyclopentenyl, cyclohexenyl, azetidinyl, pyrrolidinyl, piperidinyl, azepanyl, tetrahydrofuranyl, tetrahydropyranyl, furanyl, dihydrofuranyl, dihydropyranyl, thienyl, dihydrothienyl, tetrahydrothienyl, dihydrothiopyranyl, tetrahydrothiopyranyl, imidazolyl, imidazolinyl, and piperazinyl, which ring is unsubstituted or substituted with 1-5 substituents each independently selected from:
  (a) —C$_{1-6}$alkyl, which is unsubstituted or substituted with 1-3 substituents each independently selected from:
    (i) halo,
    (ii) hydroxy,
    (iii) —O—C$_{1-6}$alkyl, which is unsubstituted or substituted with 1-3 halo,
    (iv) —C$_{3-6}$cycloalkyl,
    (v) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —C$_{1-6}$alkyl,
      (II) —O—C$_{1-6}$alkyl,
      (III) halo,
      (IV) hydroxy,
      (V) trifluoromethyl, and
      (VI) —OCF$_3$,
    (vi) —CO$_2$R$^9$,
    (vii) —NR$^{10}$R$^{11}$,
    (viii) —SO$_2$R$^{12}$,
    (ix) —CONR$^{10a}$R$^{11a}$, and
    (x) —(NR$^{10a}$)CO$_2$R$^9$, (b) phenyl or heterocycle, wherein heterocycle is selected from: pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:
  (i) —$C_{1-6}$alkyl, which is unsubstituted or substituted with 1-6 fluoro,
  (ii) halo,
  (iii) hydroxy,
  (iv) —O—$C_{1-6}$alkyl, which is unsubstituted or substituted with 1-6 fluoro, and
  (v) —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$, and
(n) —$(NR^9)(CO)NR^{10a}R^{11a}$;

$A^1$, $A^2$ and $A^3$ are each independently selected from:
(1) a bond,
(2) —$CR^{13}R^{14}$—, wherein $R^{13}$ and $R^{14}$ are each independently selected from:
  (a) hydrogen,
  (b) $C_{1-6}$ alkyl, which is unsubstituted or substituted with 1-5 substituents each independently selected from:
    (i) —$C_{3-6}$cycloalkyl,
    (ii) —O—$C_{1-6}$alkyl,
    (iii) halo,
    (iv) hydroxy, and
    (v) phenyl,
  (c) hydroxy, and
  (d) halo,
(3) $NR^{10}$—,
(4) —$CR^{13}R^{14}$—$NR^{10}$—,
(5) —$CR^{13}R^{14}$—$CH_2$—,
(6) —$CH_2$—$CR^{13}R^{14}$—,
(7) —O—$CR^{13}R^{14}$—,
(8) —$CR^{13}R^{14}$—O—,
(9) —C≡C—,
(10) —$C(R^{13})$=$C(R^{14})$—, and
(11) —C(=O)—,
or wherein one or two of $A^1$, $A^2$ and $A^3$ are absent, $A^4$, $A^5$, $A^6$ and $A^7$ are each independently selected from:
(1) a bond, and
(2) —$CR^{13}R^{14}$—,
or wherein one of $A^4$, $A^5$, $A^6$ and $A^7$ is independently selected from:
  (i) —O—,
  (ii) —C(=O)—, and
  (iii) —$N(R^{15})$—, wherein $R^{15}$ is selected from:
    (a) hydrogen,
    (b) $C_{1-6}$ alkyl, which is unsubstituted or substituted with 1-5 substituents each independently selected from:
      (I) hydroxy,
      (II) —O—$C_{1-6}$alkyl,
      (III) halo,
      (IV) —$C_{3-6}$cycloalkyl,
      (V) trifluoromethyl, and
      (VI) phenyl,
    or wherein one or both of $A^4$ and $A^7$ are absent;

$E^1$ and $E^5$ are each independently selected from:
(1) =$C(R^4)$—,
(2) —$CR^4R^5$—,
(3) —C(=O)—,
(4) —C(=S)—,
(5) =N—,
(6) =$N^+(O^-)$—,
(7) —$N(R^4)$—,
(8) —O—,
(9) —S—, and
(10) —$SO_2$—;

$E^3$ and $E^4$ are each independently selected from:
(1) a bond,
(2) =$C(R^4)$—,
(3) —$CR^4R^5$—,
(4) —C(=O)—,
(6) =$N^+(O^-)$—,
(7) —$N(R^4)$—, and
(8) —O—,
or wherein one or both of $E^3$ and $E^4$ are absent;

$E^2$ is selected from:

(1)
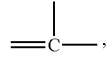

(2)
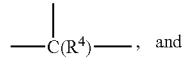, and (3)
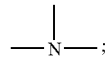;

$G^1$ and $G^2$ are each independently selected from:
(1) =$C(R^4)$—,
(2) =N—, and
(3) =$N^+(O^-)$—;

J is selected from:
(1) =$C(R^{6a})$—,
(2) —$CR^{13}R^{14}$—, and
(3) —C(=O)—;

K is selected from:
(1) =$C(R^{6b})$—,
(2) —$CR^{13}R^{14}$—,
(3) —C(=O)—,
(4) —$SO_2$—,
(5) =N—, and
(6) —$N(R^{6b})$—;

$R^4$ and $R^5$ are each independently selected from:
(1) hydrogen,
(2) —$C_{1-4}$alkyl, which is unsubstituted or substituted with 1-5 substituents each independently selected from:
  (a) halo,
  (b) hydroxy,
  (c) —O—$C_{1-6}$alkyl,
  (d) —$C_{3-6}$cycloalkyl,
  (e) phenyl,
  (f) —$CONR^{10a}R^{11a}$,
  (g) —$CO_2R^9$, and
  (h) —$NR^{10}R^{11}$, (3) —$C_{3-6}$cycloalkyl,
(4) phenyl, which is unsubstituted or substituted with 1-3 substituents each independently selected from:
  (a) —$C_{1-4}$alkyl, which is unsubstituted or substituted with 1-3 fluoro,
  (b) halo,
  (c) hydroxy, and
  (d) —O—$C_{1-6}$alkyl, which is unsubstituted or substituted with 1-6 fluoro,
(5) halo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,
(13) —$OCO_2R^9$, and
(14) —$(NR^{10a})CO_2R^9$;

$R^{6a}$ and $R^{6b}$ are each independently selected from:
(1) hydrogen;
(2) —$C_{1-4}$alkyl, which is unsubstituted or substituted with 1-5 substituents each independently selected from:
  (a) halo,
  (b) —O—$C_{1-6}$alkyl,
  (c) —$C_{3-6}$cycloalkyl,
  (d) phenyl or heterocycle, wherein heterocycle is selected from: imidazolyl, oxazolyl, pyridinyl, pyrimidinyl, pyrazinyl, pyridazinyl, piperidinyl, piperazinyl, pyrrolidinyl, thiazolyl, thienyl, triazolyl and morpholinyl,
    which phenyl or heterocycle is unsubstituted or substituted with 1-3 substituents each independently selected from:
      (i) —$C_{1-6}$alkyl,
      (ii) —O—$C_{1-6}$alkyl,
      (iii) halo,
      (iv) hydroxy,
      (v) trifluoromethyl, and
      (vi) —$OCF_3$,
(4) phenyl or heterocycle, wherein heterocycle is selected from: pyridinyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from:
  (a) —$C_{1-4}$alkyl, which is unsubstituted or substituted with 1-5 fluoro,
  (b) halo,
  (c) hydroxy,
  (d) —O—$C_{1-4}$alkyl, which is unsubstituted or substituted with 1-5 fluoro,
  (e) —$C_{3-6}$cycloalkyl, and
  (f) phenyl,
(5) halo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$, and
(11) —$CONR^{10a}R^{11a}$;
or where $R^{6a}$ and $R^{6b}$ and the atom(s) to which they are attached join to form a ring selected from cyclopentenyl, cyclohexenyl, phenyl, pyridinyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) hydroxy,
    (iii) —O—$C_{1-6}$alkyl,
    (iv) —$C_{3-6}$cycloalkyl,
    (v) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —$C_{1-6}$alkyl,
      (II) —O—$C_{1-6}$alkyl,
      (III) halo,
      (IV) hydroxy,
      (V) trifluoromethyl, and
      (VI) —$OCF_3$,
    (vi) —$CO_2R^9$,
    (vii) —$NR^{10}R^{11}$,
    (viii) —$SO_2R^{12}$,
    (ix) —$CONR^{10a}R^{11a}$, and
    (x) $(NR^{10a})CO_2R^9$,
  (b) phenyl or heterocycle, wherein heterocycle is selected from: pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:
    (i) —$C_{1-6}$alkyl, which is unsubstituted or substituted with 1-6 fluoro,
    (ii) halo,
    (iii) hydroxy,
    (iv) —O—$C_{1-6}$alkyl, which is unsubstituted or substituted with 1-6 fluoro, and
    (v) —$C_{3-6}$cycloalkyl,
  (c) halo,
  (d) —$SO_2R^{12}$,
  (e) hydroxy,
  (f) —O—$C_{1-6}$alkyl, which is unsubstituted or substituted with 1-5 halo,
  (g) —CN,
  (h) —$COR^{12}$,
  (i) —$NR^{10}R^{11}$,
  (j) —$CONR^{10a}R^{11a}$,
  (k) —$CO_2R^9$,
  (l) —$(NR^{10a})CO_2R^9$,
  (m) —$O(CO)NR^{10a}R^{11a}$,
  (n) —$(NR^9)(CO)N$—$R^{10a}R^{11a}$, and
  (o) oxo;

and pharmaceutically acceptable salts thereof and individual enantiomers and diastereomers thereof.

In embodiments of the invention where $A^1$ is $CR^{13}R^{14}$—, $A^2, A^3, A^4$ and $A^7$ are absent, $A^5$ and $A^6$ are —$CH_2$—, $G^1$ and $G^2$ are =$C(R^4)$—, $E^1$ is =N—, $E^2$ is

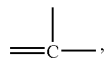

$E^3$ and $E^5$ are =C(H)—, $E^4$ is absent, J is =C($R^{6a}$)—, and K is =C($R^{6b}$)—, where $R^{6a}$ and $R^{6b}$ and the atoms to which they are attached are joined to form a pyridinyl ring, the following structure forms:

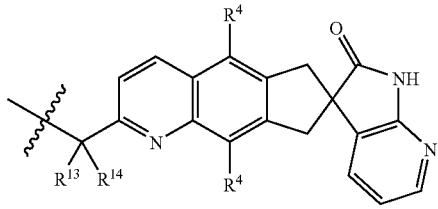

In embodiments of the invention where $A^1$ is $CR^{13}R^{14}$—, $A^2$, $A^3$, $A^4$ and $A^7$ are absent, $A^5$ and $A^6$ are —CH$_2$—, $G^1$ and $G^2$ are =C($R^4$)—, $E^5$ is =N—, $E^2$ is

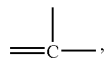

$E^1$ and $E^3$ are =C(H)—, $E^4$ is absent, J is =C($R^{6a}$)—, and K is =C($R^{6b}$)—, where $R^{6a}$ and $R^{6b}$ and the atoms to which they are attached are joined to form a pyridinyl ring, the following structure forms:

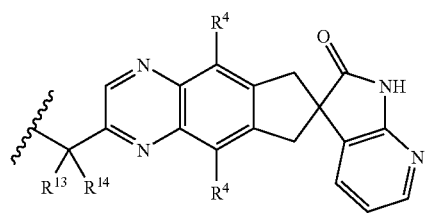

In embodiments of the invention where $A^1$ is C(=O)—, $A^2$, $A^3$, $A^4$ and $A^7$ are absent, $A^5$ and $A^6$ are —CH$_2$—, $G^1$ and $G^2$ are =C($R^4$)—, $E^1$ is =N—, $E^2$ is

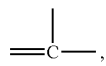

$E^3$ and $E^5$ are =C(H)—, $E^4$ is absent, J is =C($R^{6a}$)—, and K is =C($R^{6b}$)—, where $R^{6a}$ and $R^{6b}$ and the atoms to which they are attached are joined to form a pyridinyl ring, the following structure forms: the following structure forms:

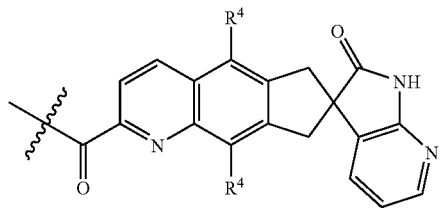

In embodiments of the invention where $A^1$ is —$CR^{13}R^{14}$—, $A^2$, $A^3$, $A^4$ and $A^7$ are absent, $A^5$ and $A^6$ are —CH$_2$—, $G^1$ and $G^2$ are =C($R^4$)—, $E^1$ and $E^5$ are =N—, $E^2$ is

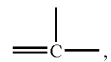

$E^3$ is =C(H)—, $E^4$ is absent, J is =C($R^{6a}$)—, and K is =C($R^{6b}$)—, where $R^{6a}$ and $R^{6b}$ and the atoms to which they are attached are joined to form a pyridinyl ring, the following structure forms:

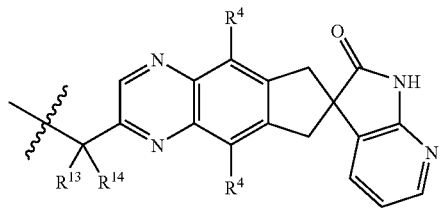

In embodiments of the invention where $A^1$ is $CR^{13}R^{14}$, $A^2$, $A^3$, $A^4$ and $A^7$ are absent, $A^5$ and $A^6$ are —CH$_2$—, $G^1$ and $G^2$ are =C($R^4$)—, $E^1$ is —N($R^4$)—, $E^2$ is

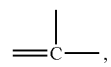

$E^3$ and $E^4$ are absent, $E^5$ is =N—, J is =C($R^{6a}$)—, and K is =C($R^{6b}$)—, where $R^{6a}$ and $R^{6b}$ and the atoms to which they are attached are joined to form a pyridinyl ring, the following structure forms:

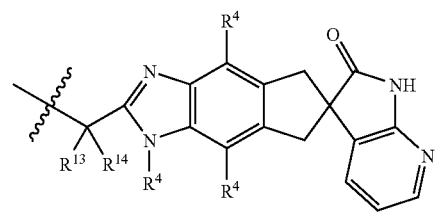

In embodiments of the invention where $A^1$ is $CR^{13}R^{14}$—, $A^2$, $A^3$, $A^4$ and $A^7$ are absent, $A^5$ and $A^6$ are —CH$_2$—, $G^1$ and $G^2$ are =C($R^4$)—, $E^1$ is —N(H)—, $E^2$ is

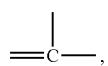

$E^3$ is =N—, $E^4$ and $E^5$; are —$CR^4R^5$—, J is =$C(R^{6a})$—, and K is =$C(R^{6b})$—, where $R^{6a}$ and $R^{6b}$ and the atoms to which they are attached are joined to form a pyridinyl ring, the following structure forms:

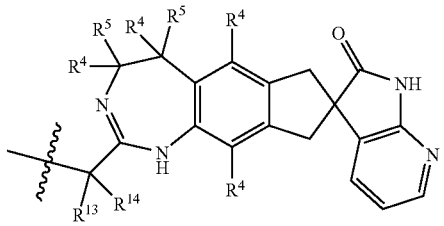

An embodiment of the present invention includes compounds of the formula Ia:

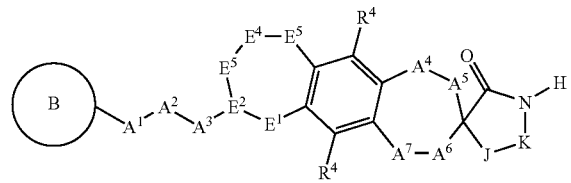

wherein $A^1$, $A^2$, $A^3$, $A^4$, $A^5$, $A^6$, $A^7$, B, $E^1$, $E^2$, $E^3$, $E^4$, $E^5$, J, K, and $R^4$ are defined herein;

and pharmaceutically acceptable salts thereof and individual enantiomers and diastereomers thereof.

Another embodiment of the present invention includes compounds of the formula Ib:

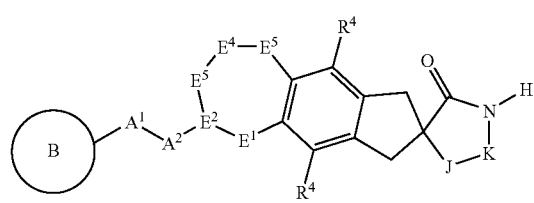

wherein $A^1$, $A^2$, B, $E^1$, $E^2$, $E^3$, $E^4$, $E^5$, J, K and $R^4$ are defined herein;

and pharmaceutically acceptable salts thereof and individual enantiomers and diastereomers thereof.

Another embodiment of the present invention includes compounds of the formula Ic:

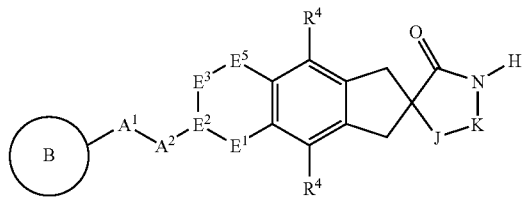

wherein $A^1$, $A^2$, B, $E^1$, $E^2$, $E^3$, $E^5$, J, K and $R^4$ are defined herein;

and pharmaceutically acceptable salts thereof and individual enantiomers and diastereomers thereof.

Another embodiment of the present invention includes compounds of the formula Id:

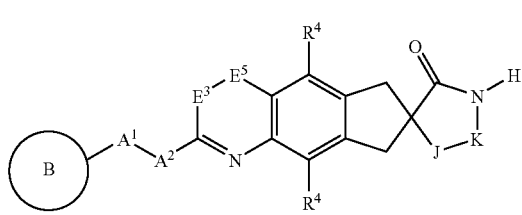

wherein $A^1$, $A^2$, B. $E^3$, $E^5$, J, K and $R^4$ are defined herein;

and pharmaceutically acceptable salts thereof and individual enantiomers and diastereomers thereof.

Another embodiment of the present invention includes compounds of the formula Ie:

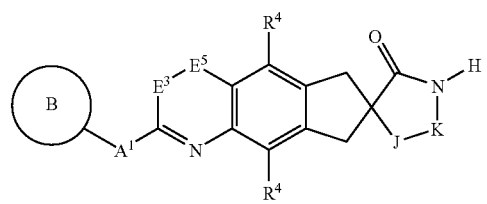

wherein $A^1$, B, $E^3$, $E^5$, J, K and $R^4$ are defined herein;

and pharmaceutically acceptable salts thereof and individual enantiomers and diastereomers thereof.

Another embodiment of the present invention includes compounds of the formula If:

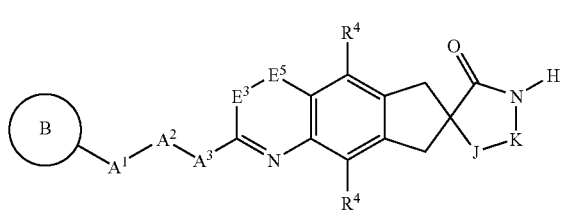

wherein $A^1$, $A^2$, $A^3$, B, $E^3$, $E^5$, J, K and $R^4$ are defined herein;

and pharmaceutically acceptable salts thereof and individual enantiomers and diastereomers thereof.

Another embodiment of the present invention includes compounds of the formula Ig:

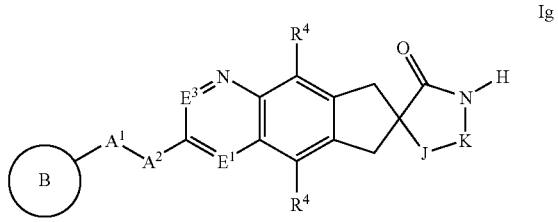

Ig wherein $A^1$, $A^2$, B, $E^1$, $E^3$, J, K and $R^4$ are defined herein;

and pharmaceutically acceptable salts thereof and individual enantiomers and diastereomers thereof.

In an embodiment of the present invention B is selected from the group consisting of: $C_{3-10}$cycloalkyl, phenyl, biphenyl, naphthyl, tetrahydronaphthyl, indanyl, indolyl, indolinyl, indazolyl, isoindolinyl, isoquinolinyl, isoxazolyl, isoxazolinyl, morpholinyl, naphthyridinyl, piperidinyl, piperazinyl, pyrazinyl, pyridazinyl, pyridinyl, pyrimidinyl, pyrimidyl, pyrrolidinyl, quinazolinyl, quinolinyl, quinoxalinyl, tetrahydroquinolinyl, phthalazinyl, pyrazolyl, isoxazolinyl, indazolyl, benzoxazolyl, benzoxazolinyl, benzimidazolyl, benzimidazolinyl, thiazolyl, and thienyl, which is unsubstituted or substituted with 1-5 substituents selected from $R^1$, $R^2$, $R^{3a}$ and $R^{3b}$, wherein $R^1$, $R^2$, $R^{3a}$ and $R^{3b}$ are defined herein.

In an embodiment of the present invention B is phenyl.
In an embodiment of the present invention B is biphenyl.
In an embodiment of the present invention B is naphthyl.
In an embodiment of the present invention B is thienyl.
In an embodiment of the present invention B is piperidinyl.
In an embodiment of the present invention B is morpholinyl.
In an embodiment of the present invention B is pyridinyl.
In an embodiment of the present invention B is quinolinyl.
In an embodiment of the present invention B is tetrahydroquinolinyl.
In an embodiment of the present invention B is quinoxalinyl.
In an embodiment of the present invention B is phthalazinyl.
In an embodiment of the present invention B is pyrrolidinyl.
In an embodiment of the present invention B is pyrazolyl.
In an embodiment of the present invention B is isoxazolinyl.
In an embodiment of the present invention B is isoxazolyl.
In an embodiment of the present invention B is quinazolinyl.
In an embodiment of the present invention B is norbornyl.
In an embodiment of the present invention B is cyclohexyl.
In an embodiment of the present invention B is cyclopentyl.
In an embodiment of the present invention B is cyclopropyl.
In an embodiment of the present invention B is thiazolyl.
In an embodiment of the present invention B is indanyl.
In an embodiment of the present invention B is indolinyl.
In an embodiment of the present invention B is indazolyl.
In an embodiment of the present invention B is indolyl.
In an embodiment of the present invention B is isoindolinyl.
In an embodiment of the present invention B is benzoxazolinyl.
In an embodiment of the present invention B is benzoxazolyl.
In an embodiment of the present invention B is benzimidazolinyl.
In an embodiment of the present invention B is benzimidazolyl.

In an embodiment of the present invention $R^1$, $R^2$, $R^{3a}$ and $R^{3b}$ are independently selected from:
(1) $C_{1-6}$ alkyl, which is unsubstituted or substituted with 1-5 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: pyridinyl, piperidinyl, piperazinyl, pyrrolidinyl, or morpholinyl,
  (f) —(NR$^{10a}$)CO$_2$R$^9$, and
  (g) NR$^{10}$R$^{11}$,
(2) $C_{3-6}$ cycloalkyl,
(3) —OR$^9$,
(4) —OCF$_3$,
(5) trifluoromethyl,
(6) halo,
(7) oxo,
(8) hydroxy,
(9) —CN,
(10) —COR$^{12}$,
(11) —CO$_2$R$^{12}$,
(12) —CONR$^{10a}$R$^{11a}$,
(13) —NR$^{10}$R$^{11}$,
(14) phenyl, which is unsubstituted or substituted with 1-5 substituents selected from:
  (a) $C_{1-6}$alkyl,
  (b) —O—$C_{1-6}$alkyl,
  (c) halo,
  (d) —OH, and
  (e) —CF$_3$, and
(15) heterocycle, wherein heterocycle is selected from: pyridinyl, pyrimidinyl, pyrazinyl, thienyl, pyrrolidinyl, piperazinyl, piperidinyl, tetrazolyl, or morpholinyl, and which is unsubstituted or substituted with 1-5 substituents selected from:
  (a) $C_{1-6}$alkyl,
  (b) —O—$C_{1-6}$alkyl,
  (c) halo,
  (d) —OH, and
  (e) —CF$_3$.

In an embodiment of the present invention, $R^{3a}$ and $R^{3b}$ and the carbon atom(s) to which they are attached are joined together to form a ring selected from piperidinyl, cyclohexyl, cyclopentyl, pyrrolidinyl, tetrahydrofuranyl, tetrahydropyranyl, tetrahydrothienyl, and tetrahydrothiopyranyl, which is unsubstituted or substituted with 1-3 substituents independently selected from:
(a) —$C_{1-6}$alkyl, which is unsubstituted or substituted with 1-3 substituents each independently selected from:
  (i) halo, and
  (ii) phenyl,
(b) phenyl or heterocycle, wherein heterocycle is selected from: pyridinyl, pyrimidinyl and pyrazinyl, (c) —CO$_2$R$^9$,
(d) hydroxy, and
(e) oxo.

In an embodiment of the present invention, R$^{3a}$ and R$^{3b}$ and the carbon atom(s) to which they are attached join to form a ring selected from piperidinyl, cyclohexyl, tetrahydropyranyl, and tetrahydrothiopyranyl, which ring is unsubstituted or substituted with 1-3 substituents independently selected from:
  (a) —C$_{1-6}$alkyl, which is unsubstituted or substituted with 1-3 substituents independently selected from:
    (i) fluoro, and
    (ii) phenyl,
  (b) —CO$_2$—C$_{1-4}$alkyl,
  (c) hydroxyl, and
  (d) oxo.

In an embodiment of the present invention A$^1$ is a bond.
In an embodiment of the present invention A$^1$ is —CR$^{13}$R$^{14}$—.
In an embodiment of the present invention A$^1$ is —CH$_2$—.
In an embodiment of the present invention A$^1$ is —OCH$_2$—.
In an embodiment of the present invention A$^1$ is —C≡C—.
In an embodiment of the present invention A$^1$ is —CH$_2$—CH$_2$—.
In an embodiment of the present invention A$^1$ is —C(H)=C(H)—.
In an embodiment of the present invention A$^1$ is —NH—.
In an embodiment of the present invention A$^1$ is —C(=O)—.
In an embodiment of the present invention A$^2$ is CH$_2$.
In an embodiment of the present invention A$^2$ is —CH$_2$—NH—.
In an embodiment of the present invention A$^2$ is —C(=O)—.
In an embodiment of the present invention A$^2$ is —C≡C—.
In an embodiment of the present invention A$^2$ is —NH—.
In an embodiment of the present invention A$^2$ is —CH$_2$—CH$_2$—.
In an embodiment of the present invention A$^2$ is a bond.
In an embodiment of the present invention A$^3$ is —CH$_2$—.
In an embodiment of the present invention A$^3$ is —C(=O)—.
In an embodiment of the present invention A$^3$ is —CH$_2$—.
In an embodiment of the present invention A$^3$ is —CH$_2$O—.
In an embodiment of the present invention A$^3$ is a bond.
In an embodiment of the present invention A$^4$ is selected from: CH$_2$; and a bond.
In an embodiment of the present invention A$^4$ is a bond.
In an embodiment of the present invention A$^5$ is CH$_2$.
In an embodiment of the present invention A$^6$ is CH$_2$—
In an embodiment of the present invention A$^7$ is selected from: CH$_2$; and a bond.
In an embodiment of the present invention A$^7$ is a bond.
In an embodiment of the present invention E$^1$ is selected from:
=C(R$^4$)—; —CR$^4$R$^5$—; =N—; and —N(R$^4$)—; wherein R$^4$ and R$^5$ are defined herein.
In an embodiment of the present invention E$^1$ is selected from: =N—; and —N(H)—.
In an embodiment of the present invention E$^5$ is selected from:
=C(R$^4$)—; —CR$^4$R$^5$—; =N—; and —N(R$^4$)—; wherein R$^4$ and R$^5$ are defined herein.

In an embodiment of the present invention E$^5$ is selected from:
=C(H)—; —CH$_2$—; =N—; and —N(H)—.
In an embodiment of the present invention E$^3$ is selected from:
a bond; —C(R$^4$)—; —CR$^4$R$^5$—; =N—; and —N(R$^4$)—; wherein R$^4$ and R$^5$ are defined herein.
In an embodiment of the present invention E$^3$ is selected from:
a bond; =C(H)—; =N—; and —N(H)—.
In an embodiment of the present invention E$^4$ is selected from:
a bond; and —CH$_2$—.
In an embodiment of the present invention E$^4$ is a bond.
In an embodiment of the present invention E$^2$ is selected from:

$$=\!\!\overset{|}{C}\!\!-\!\!;\ \text{and}\ -\!\!\overset{|}{N}\!\!-.$$

In an embodiment of the present invention E$^2$ is $$=\!\!\overset{|}{C}\!\!-.$$

In an embodiment of the present invention G$^1$ is =C(R$^4$)—.
In an embodiment of the present invention G$^1$ is =C(H)—.
In an embodiment of the present invention G$^2$ is =C(R$^4$)—.
In an embodiment of the present invention G$^2$ is =C(H)—.
In an embodiment of the present invention J is selected from:
=C(R$^{6a}$)—; and —CH$_2$—; wherein R$^{6a}$ is defined herein.
In an embodiment of the present invention J is —CH$_2$—.
In an embodiment of the present invention J is =C(R$^{6a}$)—; wherein R$^{6a}$ is defined herein.
In an embodiment of the present invention K is selected from:
=C(R$^{6b}$)—; —CH$_2$—; and —C(=O)—; wherein R$^{6b}$ is defined herein.
In an embodiment of the present invention K is —CH$_2$—.
In an embodiment of the present invention K is =C(R$^{6b}$)—; wherein R$^{6b}$ is defined herein.
In an embodiment of the present invention R$^4$ and R$^5$ are independently selected from:
  (1) hydrogen;
  (2) —C$_{1-4}$alkyl, which is unsubstituted or substituted with 1-3 substituents each independently selected from:
    (a) halo,
    (b) hydroxy,
    (c) —O—C$_{1-6}$alkyl,
    (d) —C$_{3-6}$cycloalkyl, and
    (e) phenyl,
  (3) —C$_{3-6}$cycloalkyl,
  (4) phenyl, which is unsubstituted or substituted with 1-3 substituents each independently selected from:
    (a) —C$_{1-4}$alkyl, which is unsubstituted or substituted with 1-3 fluoro, and
    (b) halo,
  (5) halo,
  (6) hydroxy, (7) —O—$C_{1-6}$alkyl, which is unsubstituted or substituted with 1-3 fluoro,
(8) —CN, and
(9) —$NR^{10}R^{11}$;

In an embodiment of the present invention $R^4$ and $R^5$ are independently selected from:
(1) hydrogen,
(2) —$C_{1-4}$alkyl, which is unsubstituted or substituted with 1-3 fluoro,
(3) phenyl,
(5) halo, and
(6) hydroxy;

In an embodiment of the present invention $R^4$ and $R^5$ are independently selected from: hydrogen, halo, and methyl.

In an embodiment of the present invention $R^4$ is hydrogen.

In an embodiment of the present invention $R^5$ is hydrogen.

In an embodiment of the present invention $R^{6a}$ and $R^{6b}$ are independently selected from:
(1) hydrogen;
(2) —$C_{1-4}$alkyl, which is unsubstituted or substituted with 1-3 substituents each independently selected from:
  (a) halo,
  (b) —O—$C_{1-6}$alkyl,
  (c) —$C_{3-6}$cycloalkyl, and
  (d) phenyl,
(3) phenyl or heterocycle, wherein heterocycle is selected from: pyridinyl, pyrimidinyl, pyrazinyl, thiazolyl, oxazolyl, tetrahydrofuryl, piperidinyl, and morpholinyl, which is unsubstituted or substituted with 1-3 substituents each independently selected from:
  (a) —$C_{1-4}$alkyl, which is unsubstituted or substituted with 1-3 fluoro,
  (b) halo,
  (c) hydroxy, and
  (d) —O—$C_{1-4}$alkyl, which is unsubstituted or substituted with 1-3 fluoro,
(4) halo,
(5) —$NR^{10}R^{11}$,
(6) hydroxy,
(7) —O—$C_{1-4}$alkyl, which is unsubstituted or substituted with 1-3 halo.

In an embodiment of the present invention $R^{6a}$ and $R^{6b}$ are independently selected from:
(1) hydrogen;
(2) —$C_{1-4}$alkyl, which is unsubstituted or substituted with 1-3 fluoro, and
(3) phenyl or heterocycle, wherein heterocycle is selected from: pyridinyl, pyrimidinyl, pyrazinyl, thiazolyl, oxazolyl, tetrahydrofuryl, piperidinyl, and morpholinyl.

In an embodiment of the present invention $R^{6a}$ and $R^{6b}$ and the atom(s) to which they are attached join to form a ring selected from phenyl, pyridinyl, pyrimidinyl, pyrazinyl, pyridazinyl, thiazolyl, oxazolyl, imidazolyl, thienyl, which is unsubstituted or substituted with 1-3 substituents each independently selected from:
  (a) —$C_{1-4}$ally, which is unsubstituted or substituted with 1-3 substituents each independently selected from:
    (i) halo,
    (ii) —O—$C_{1-6}$alkyl,
    (iii) —$CO_2R^9$,
    (iv) —$NR^{10}R^{11}$, and
    (v) —$CONR^{10a}R^{11a}$,
  (b) phenyl or heterocycle, wherein heterocycle is selected from: pyridinyl, pyrimidinyl, pyrazinyl, pyrrolidinyl, azetidinyl, piperidinyl and morpholinyl, which is unsubstituted or substituted with 1-3 substituents each independently selected from:
    (i) —$C_{1-4}$alkyl, which is unsubstituted or substituted with 1-5 fluoro,
    (ii) halo,
    (iii) hydroxy, and
    (iv) —O—$C_{1-4}$alkyl, which is unsubstituted or substituted with 1-3 fluoro,
  (c) halo,
  (d) hydroxy,
  (e) —O—$C_{1-6}$alkyl, which is unsubstituted or substituted with 1-5 halo,
  (f) —CN,
  (g) —$NR^{10}R^{11}$,
  (h) —$CONR^{10a}R^{11a}$, and
  (i) oxo.

In an embodiment of the present invention $R^{6a}$ and $R^{6b}$ and the atom(s) to which they are attached join to form a ring selected from phenyl, pyridinyl, and pyrimidinyl, which is unsubstituted or substituted with 1-3 substituents each independently selected from:
  (a) —$C_{1-4}$alkyl, which is unsubstituted or substituted with 1-3 fluoro,
  (b) halo,
  (c) hydroxy, and
  (d) —O—$C_{1-4}$alkyl.

In an embodiment of the present invention $R^{6a}$ and $R^{6b}$ and the atom(s) to which they are attached join to form a ring selected from pyridinyl, and pyrimidinyl.

In an embodiment of the present invention $R^9$ is selected from:
(i) hydrogen,
(ii) —$C_{1-4}$alkyl, which is unsubstituted or substituted with 1-5 substituents, substituents each independently selected from:
  (I) halo,
  (II) hydroxy,
  (III) —O—$C_{1-4}$alkyl, which is unsubstituted or substituted with 1-3 halo,
  (IV) —$C_{3-6}$cycloalkyl,
  (V) phenyl, which is unsubstituted or substituted with 1-3 substituents each independently selected from:
    (1) —$C_{1-4}$alkyl,
    (2) —O—$C_{1-4}$alkyl, and
    (3) halo,
(iii) —$C_{3-6}$cycloalkyl, which is unsubstituted or substituted with 1-4 substituents, substituents each independently selected from:
  (I) halo,
  (II) hydroxyl, and
  (III) —$C_{1-4}$alkyl, which is unsubstituted or substituted with 1-3 halo, and
(iv) phenyl or heterocycle, wherein heterocycle is selected from: pyridinyl, pyrimidinyl, pyrazinyl, thienyl, pyrrolidinyl, imidazolyl, triazolyl, tetrazolyl, indolinyl, indolyl, tetrahydrofuryl, piperidinyl, piperazinyl, and morpholinyl, which phenyl or heterocycle is unsubstituted or substituted with 1-3 substituents each independently selected from:
  (I) halo,
  (II) —$C_{1-4}$alkyl, which is unsubstituted or substituted with 1-4 fluoro
  (III) —O—$C_{1-4}$alkyl, which is unsubstituted or substituted with 1-3 fluoro
  (IV) —$C_{3-6}$cycloalkyl,
  (V) oxo, and
  (VI) phenyl.

In an embodiment of the present invention $R^9$ is selected from:
- (i) hydrogen,
- (ii) —$C_{1-4}$alkyl, which is unsubstituted or substituted with 1-3 substituents, substituents each independently selected from:
  - (I) halo,
  - (II) hydroxy,
  - (III) —O—$C_{1-4}$alkyl,
  - (IV) —$C_{3-6}$cycloalkyl, and
  - (V) phenyl,
- (iii) —$C_{3-6}$cycloalkyl, which is unsubstituted or substituted with 1-3 substituents, substituents each independently selected from:
  - (I) halo, and
  - (II) —$C_{1-4}$alkyl, which is unsubstituted or substituted with 1-3 fluoro, and
- (iv) phenyl.

In an embodiment of the present invention $R^{10}$ and $R^{11}$ are each independently selected from:
- (i) hydrogen,
- (ii) —$C_{1-4}$alkyl, which is unsubstituted or substituted with 1-5 substituents each independently selected from:
  - (I) —O—$C_{1-4}$alkyl,
  - (II) halo,
  - (III) hydroxy,
  - (IV) —$C_{3-6}$cycloalkyl, and
  - (V) phenyl,
- (iii) —$C_{4-6}$cycloalkyl,
- (iv) phenyl, which is unsubstituted or substituted with 1-3 substituents each independently selected from:
  - (I) —$C_{1-4}$alkyl,
  - (II) —O—$C_{1-4}$alkyl,
  - (III) halo, and
  - (IV) trifluoromethyl,
- (v) benzyl, which is unsubstituted or substituted with 1-3 substituents each independently selected from:
  - (I) —$C_{1-4}$alkyl,
  - (II) —O—$C_{1-4}$alkyl,
  - (III) halo, and
  - (IV) trifluoromethyl,
- (vi) —$COR^9$, and
- (vii) —$SO_2R^{12}$.

In an embodiment of the present invention $R^{10}$ and $R^{11}$ are each independently selected from:
- (i) hydrogen,
- (ii) —$C_{1-4}$alkyl, which is unsubstituted or substituted with 1-3 substituents each independently selected from:
  - (I) —O—$C_{1-4}$alkyl,
  - (II) halo,
  - (III) —$C_{3-6}$cycloalkyl, and
  - (IV) phenyl,
- (iii) —$C_{4-6}$cycloalkyl,
- (iv) phenyl, which is unsubstituted or substituted with 1-3 substituents each independently selected from:
  - (I) —$C_{1-4}$alkyl, and
  - (II) halo,
- (v) benzyl, which is unsubstituted or substituted with 1-3 substituents each independently selected from:
  - (I) —$C_{1-4}$alkyl, and
  - (II) halo,
- (vi) —$COR^9$, and
- (vii) —$SO_2R^{12}$.

In an embodiment of the present invention $R^{10a}$ and $R^{11a}$ are each independently selected from:
- (i) hydrogen,
- (ii) —$C_{1-4}$alkyl, which is unsubstituted or substituted with 1-3 substituents each independently selected from:
  - (I) —O—$C_{1-4}$alkyl,
  - (II) halo,
  - (III) hydroxy,
  - (IV) —$C_{3-6}$cycloalkyl, and
  - (V) phenyl,
- (iii) —$C_{5-6}$cycloalkyl,
- (iv) phenyl, which is unsubstituted or substituted with 1-3 substituents each independently selected from:
  - (I) —$C_{1-4}$alkyl,
  - (II) —O—$C_{1-4}$alkyl,
  - (III) halo, and
  - (IV) trifluoromethyl,
- (v) benzyl, which is unsubstituted or substituted with 1-3 substituents each independently selected from:
  - (I) —$C_{1-4}$alkyl,
  - (II) —O—$C_{1-4}$alkyl,
  - (III) halo, and
  - (IV) trifluoromethyl,
- or where $R^{10a}$ and $R^{11a}$ join to form a ring selected from pyrrolidinyl, piperidinyl, piperazinyl, or morpholinyl, which ring is unsubstituted or substituted with 1-4 substituents each independently selected from:
  - (I) —$C_{1-4}$alkyl
  - (II) halo
  - (III) hydroxy
  - (IV) phenyl,
  - (V) benzyl,
  - (VI) —$COR^9$, and
  - (VII) —$SO_2R^{12}$.

In an embodiment of the present invention $R^{10a}$ and $R^{11a}$ are each independently selected from:
- (i) hydrogen,
- (ii) —$C_{1-4}$alkyl, which is unsubstituted or substituted with 1-3 substituents each independently selected from:
  - (I) fluoro,
  - (II) hydroxy, and
  - (III) phenyl,
- (iii) —$C_{5-6}$cycloalkyl,
- (iv) phenyl, which is unsubstituted or substituted with 1-3 substituents each independently selected from:
  - (I) —$C_{1-4}$alkyl, and
  - (II) halo,
- (v) benzyl, which is unsubstituted or substituted with 1-3 substituents each independently selected from:
  - (I) —$C_{1-4}$alkyl, and
  - (II) halo,
- or where $R^{10a}$ and $R^{11a}$ join to form a ring selected from pyrrolidinyl, piperidinyl, piperazinyl, or morpholinyl, which ring is unsubstituted or substituted with 1-3 substituents each independently selected from:
  - (I) —$C_{1-4}$alkyl
  - (II) halo
  - (IV) phenyl,
  - (V) benzyl, and
  - (VI) —$COR^9$.

In an embodiment of the present invention $R^{12}$ is selected from:
- (i) —$C_{1-4}$alkyl, which is unsubstituted or substituted with 1-3 fluoro,
- (ii) —$C_{3-6}$cycloalkyl, (iii) phenyl or heterocycle, wherein heterocycle is selected from: pyridinyl, pyrimidinyl, pyrazinyl, piperidinyl, piperazinyl, pyrrolidinyl, thienyl and morpholinyl, which phenyl or heterocycle is unsubstituted or substituted with 1-3 substituents each independently selected from:
- (I) —$C_{1-4}$alkyl,
- (II) —O—$C_{1-4}$alkyl,
- (III) halo,
- (IV) hydroxy,
- (V) trifluoromethyl, (iv) benzyl, which is unsubstituted or substituted with 1-3 substituents each independently selected from:
- (I) —$C_{1-4}$alkyl,
- (II) —O—$C_{1-4}$alkyl,
- (III) halo, and
- (IV) trifluoromethyl.

In an embodiment of the present invention $R^{12}$ is selected from:
- (i) —$C_{1-4}$alkyl,
- (ii) —$C_{3-6}$cycloalkyl,
- (iii) phenyl, which is unsubstituted or substituted with 1-3 substituents each independently selected from:
  - (I) —$C_{1-4}$alkyl, and
  - (II) halo,
- (iv) benzyl, which is unsubstituted or substituted with 1-3 substituents each independently selected from:
  - (I) —$C_{1-4}$allyl, and
  - (II) halo.

It is to be understood that where one or more of the above recited structures or substructures recite multiple substituents having the same designation each such variable may be the same or different from each similarly designated variable. For example, $R^2$ is recited four times in formula I, and each $R^2$ in formula I may independently be any of the substructures defined under $R^2$. The invention is not limited to structures and substructures wherein each $R^2$ must be the same for a given structure. The same is true with respect to any variable appearing multiple time in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 4- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The terms "bond" and "absent" are in certain instances herein used interchangeably to refer to an atom (or chemical moiety) which is not present in a particular embodiment of the invention. In such embodiments, the atoms adjacent the "bond" or "absent" atom are simply bonded to one another. For example, in certain embodiments of the invention described and claimed herein, where -$A^1$-$A^2$-$A^3$-links $B^4$ to $E^2$, $A^1$ is defined as $CR^{13}R^{14}$ while $A^2$ and $A^3$ are described as "absent". In such a molecule, it is understood that $A^1$ is bonded directly to the moiety adjacent $A^3$, i.e. the moiety $E^2$, resulting in the sub-structure $B^4$-$A^1$-$E^2$. The absence of a specific atom or moiety, particularly an atom or moiety which serves to link or connect other atoms or moieties, does not imply that such other atoms or moieties are not linked.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the examples and herein. Specific compounds within the present invention include a compound which selected from the group consisting of the compounds disclosed in the following examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 ml of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 µl) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 µg/ml streptomycin at 37° C., 95% humidity, and 5% CO$_2$. For cAMP assays, cells were plated at 5×10$^5$ cells/well in 96-well poly-D-lysine-coated plates (Becton-Dickinson) and cultured for ~18 h before assay. Cells were washed with phosphate-buffered saline (PBS, Sigma) then pre-incubated with 300 µM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ0014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm$^2$ flasks CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{Y_{min} + (Y_{max} - Y_{min})(100 - \% \ I_{max}/100)}{1 + ([\text{Drug}]/K_i(1 + [\text{Radiolabel}]/K_d)^{nH}}$$

$$+ \frac{(Y_{max} - Y_{min})(\% \ I_{max} - \% I_{min}/100)}{}$$

Where Y is observed CPM bound, Y$_{max}$ is total bound counts, Y min is non specific bound counts, (Y max−Y min) is specific bound counts, % I max is the maximum percent inhibition, % I min is the minimum percent inhibition, radiolabel is the probe, and the K$_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and IC$_{50}$ values determined from a 4-parameter logistic fit as defined by the equation y=((a−d)/(1+(x/c)$^b$)+d, where y=response, x=dose, a=max response, d=min response, c=inflection point and b=slope.

In particular, the compounds of the following examples had activity as antagonists of the CGRP receptor in the aforementioned assays, generally with a K$_i$ or IC$_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocomine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 10 milligrams to about 1000 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following schemes and examples. Starting materials are made according to procedures known in the art or as illustrated herein.

The compounds of the present invention can be prepared readily according to the following schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following schemes.

The synthesis of aniline intermediates may be conducted as described in schemes 1-5. Aniline intermediates bearing a variety of substituents may be prepared by employing appropriately substituted starting materials or by derivatization of any intermediates and/or final products as desired by methods known in the art.

SCHEME 1

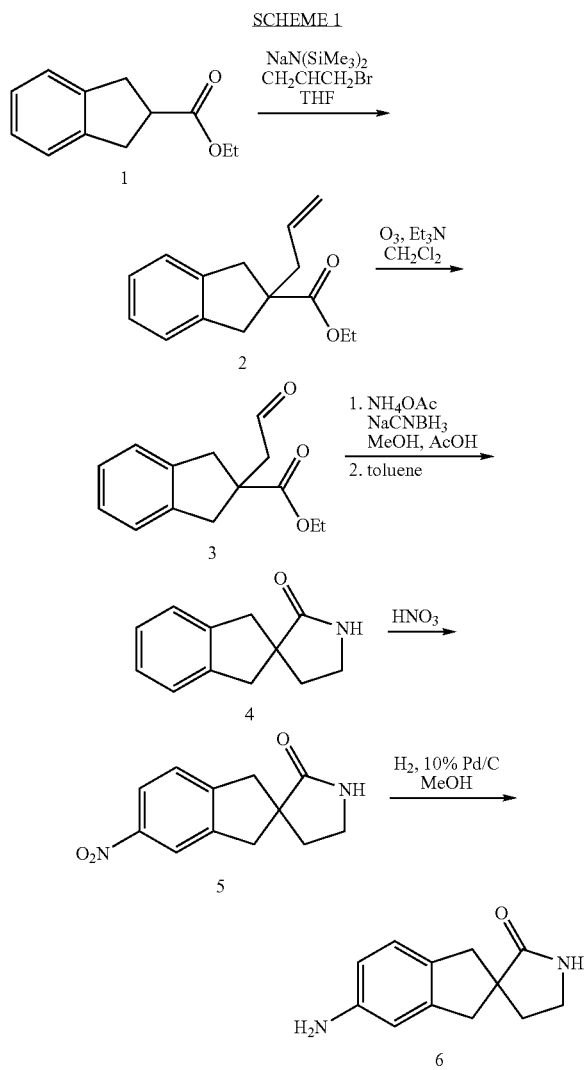

SCHEME 2

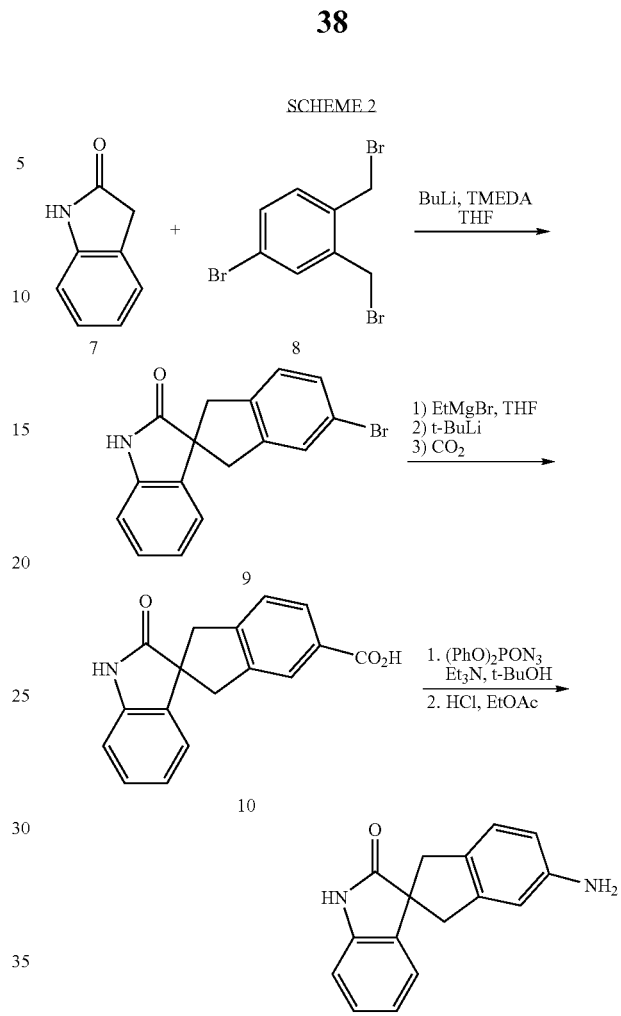

The synthesis of a representative spirolactam aniline (6) is illustrated in scheme 1. The known ethyl indane-2-carboxylate (1, Schaaf et al., *J. Med. Chem.* 1983, 26, 328-334) may be alkylated using allyl bromide and sodium bis(trimethylsilyl)amide to form 2. Oxidation of the allyl group with ozone can produce the aldehyde 3, which cyclizes to the lactam 4 after treatment with ammonium acetate and sodium cyanoborohydride and heating in toluene. The reductive amination of aldehyde 3 with amines other than ammonia may be used to provide a variety of N-protected analogues of lactam 4, which may facilitate subsequent chemical steps prior to removal of the lactam protecting group. The intermediate lactam may be nitrated, for example using 70% nitric acid, and the resulting nitro compound 5 can be reduced to provide the aniline intermediate 6, using a variety of well known methodologies, such as catalytic hydrogenation. Those skilled in the art of organic synthesis will recognize that straightforward modifications of this methodology may be used to access other spirolactam intermediates, such as those with other lactam ring sizes. Additionally, use of an alternative starting material to the indane 1 may be used to provide different products, such as tetralin-based spirolactams.

In scheme 2, an example of the synthesis of a spirooxindole intermediate is shown.

Treatment of oxindole (7) with butyllithium and tetramethylethylenediamine, followed by a dihalide or its equivalent, e.g. 4-bromo-1,2-bis(bromomethyl)benzene [Anderson et al., *J. Org. Chem.* 1979, 44(9), 1519-1533], leads to the spirooxindole 9. The bromide may be converted to a carboxylic acid (10) by treatment with ethylmagnesium bromide and tert-butyllithium, and quenching of the resulting organolithium species with carbon dioxide. A Curtius rearrangement using diphenylphosphoryl azide in tert-butanol, followed by deprotection with hydrochloric acid can provide the aniline 11. Alternative conditions, such as treatment of acid 10 with sodium azide in concentrated sulfuric acid, may also be used to provide aniline 11.

Scheme 3 illustrates a route to spiroimide derivative 16, using methodology that is similar to that shown in scheme 1. Ethyl indane-2-carboxylate (1) may be alkylated with tert-butyl bromoacetate to form the diester 12. Subjection of 12 to basic, then acidic, hydrolysis conditions can provide the diacid 13. Treatment of the diacid 13 with a number of different reagents can provide imide 14 or a derivative thereof. In scheme 3, heating 13 in the presence of acetyl chloride, followed by reaction with ammonia affords spiroimide 14. Reaction with sodium nitrite in trifluoroacetic acid, followed by hydrogenation over palladium can provide the aniline 16.

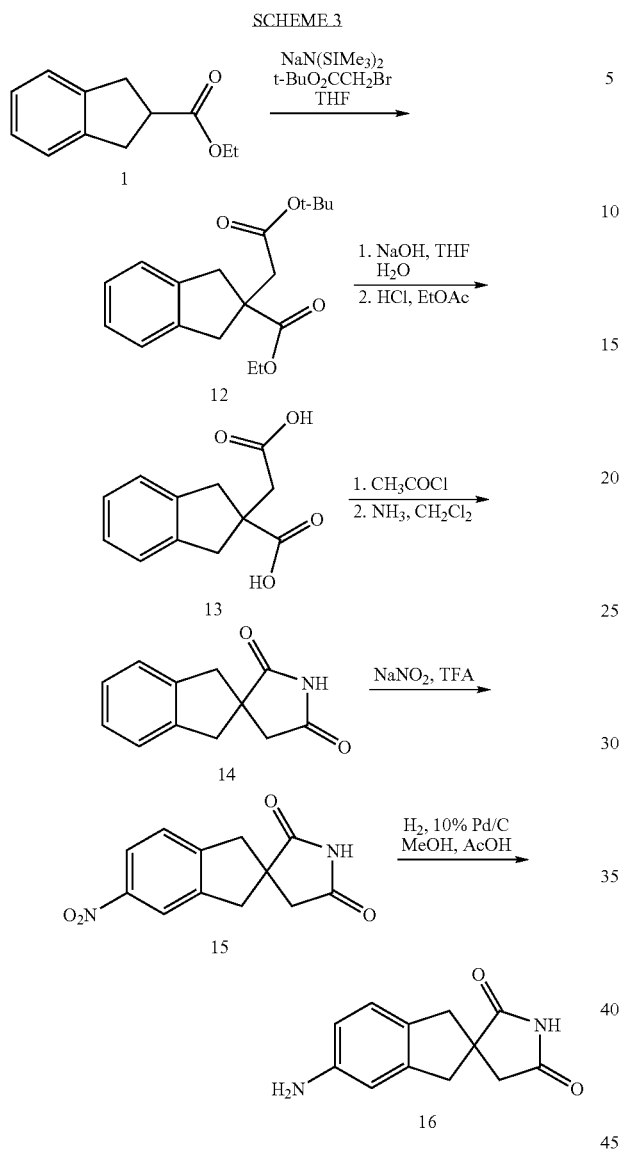

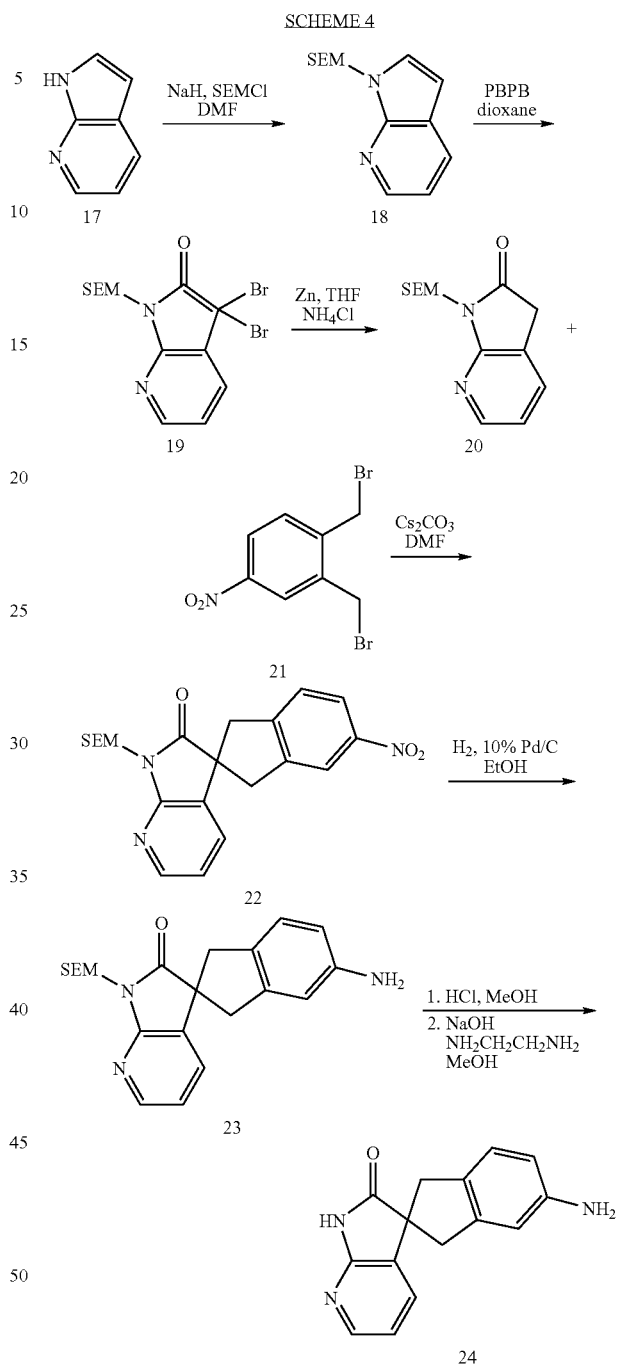

A representative synthesis of a spiroazaoxindole intermediate is shown in scheme 4. 7-Azaindole (17) may be protected with a variety of protecting groups, such as the 2-(trimethylsilyl)ethoxymethyl group shown in scheme 4. Following the method of Marfat and Carter (*Tetrahedron Lett.*, 1987, 28, 4027-4030), treatment of 18 with pyridine hydrobromide perbromide provides the dibromoazaoxindole 19, which may be reduced to the corresponding azaoxindole 20 by reaction with zinc. The key alkylation of 20 with 1,2-bis(bromomethyl)-4-nitrobenzene (21, Cava et al., *J. Org. Chem.* 2000, 65, 5413-5415) is carried out using cesium carbonate in DMF to afford the spiroazaoxindole 22. A variety of other bases and solvents may be employed in this alkylation reaction, and use of a different alkylating agent than the dibromide shown here can lead to other products. Reduction of the nitro compound 22, for example using hydrogenation over palladium, and a two-step deprotection affords the corresponding aniline 24. The methodology shown in scheme 4 is not limited to azaoxindoles such as 20, but may be applied to a variety of suitably protected heterocyclic systems to give the corresponding spiro compounds.

Spiroazaoxindole intermediates, such as those illustrated in scheme 4, may be resolved to give pure enantiomers using techniques familiar to those skilled in the art. For example, chromatography of the protected intermediate 23 on a Chiral-Pak OD column can be used to provide the individual enantiomers (R)-23 and (S)-23, and these enantiomers may be converted to the corresponding anilines [(R)-24 and (S)-24] by the two-step deprotection. The methodology described herein may be applied to such enantiomerically pure aniline intermediates to give the individual enantiomers of the compounds of the present invention. Resolution may be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

As an example of related methodology to that described in scheme 4, using alternative conditions for the alkylation reaction, the synthesis of spirodiazaoxindole compounds is outlined in scheme 5. Published methodology is used to convert 6-chloro-deazapurine into 4-chloro-diazaoxindole 25, the starting material in scheme 5 (Sun et al., *Biorg. Med. Chem. Lett.* 2002, 12, 2153-2157).

SCHEME 5

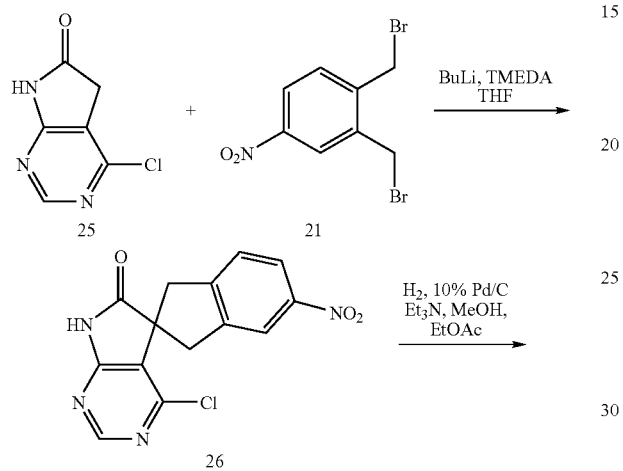

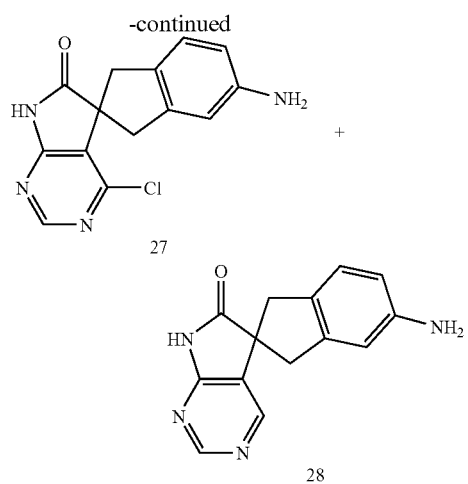

Alkylation with dibromide 21 under similar conditions to that shown in scheme 2 may provide the spirodiazaoxindole 26. Hydrogenation at 30 psi for two hours can provide the aniline 27, while hydrogenation at higher pressure (55 psi) and longer reaction time (180 hours) can provide the deschloro analogue 28.

Aniline intermediates, such as those described in schemes 1-5, may be converted to a variety of other key intermediates that are useful in the synthesis of the compounds of the present invention. For example, scheme 6 illustrates methodology for conversion of a representative aniline into several quinoline intermediates.

SCHEME 6

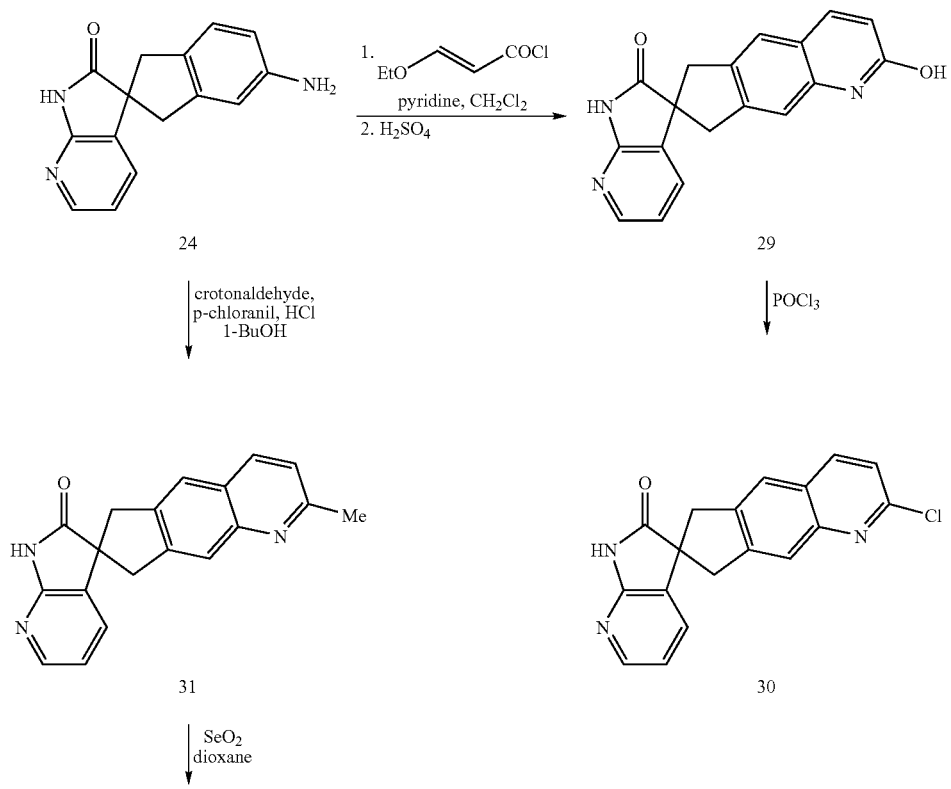

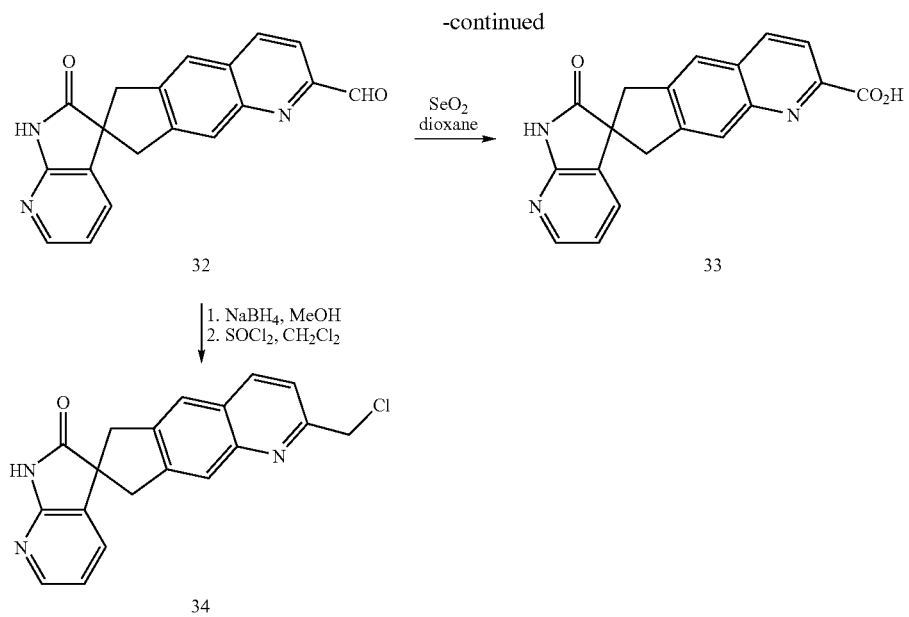

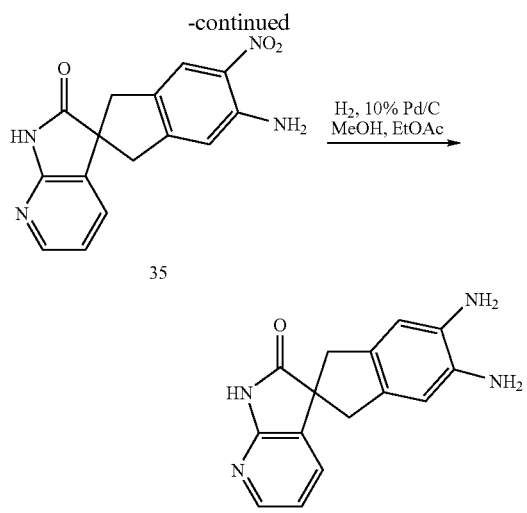

Aniline 24 may be acylated with (E)-3-ethoxyacryloyl chloride and treatment of the resulting amide with sulfuric acid leads to hydroxyquinoline 29, which can be converted to the corresponding chloride 30 by heating in phosphorus oxychloride. Condensation of aniline 24 with crotonaldehyde in the presence of acid and an oxidant affords the 2-methylquinoline 31. The use of other aldehydes under similar conditions can lead to alternatively substituted quinolines. Oxidation of quinoline 31 with selenium dioxide can provide either aldehyde 32 or carboxylic acid 33, depending on the amount of oxidant used and the duration of the reaction. Reduction of aldehyde 32 with sodium borohydride provides the corresponding alcohol, and treatment of this with thionyl chloride may be used to give the chloride 34. Intermediates such as 30, 32, 33 and 34 may be converted to compounds of the present invention using a variety of known methodology. While the methodology shown in scheme 6 is exemplified using aniline 24, it is understood that it may be applied to a variety of aniline substrates, such as those described herein, in order to provide various quinoline intermediates.

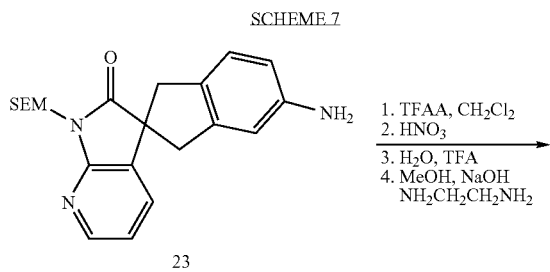

Scheme 7 illustrates the synthesis of a useful diamine intermediate. The aniline 23 is converted to the trifluoroacetanilide, which is subjected to standard nitration conditions, followed by removal of the protecting groups to give nitroaniline 35. Reduction of this nitro compound, for example by catalytic hydrogenation, affords the phenylene diamine 36. The same nitroaniline intermediate (35) may be used to provide other useful diamine intermediates. Another example is shown in scheme 8, in which 35 is elaborated to give the 2-aminophenethylamine 42. Diazotization of the nitroaniline followed by reaction of the diazonium salt with potassium iodide affords 37, which may be protected with a 2-(trimethylsilyl)ethoxymethyl group. The resulting iodide 38 is a versatile intermediate which may be modified through a variety of known methodology. For example, palladium-mediated couplings can be used to give many different products, such as the ester 39, which is obtained when the coupling partner of the iodide is 2-tert-butoxy-2-oxoethylzinc chloride, as shown in scheme 8. Simultaneous removal of the tert-butyl ester and SEM protecting groups provides the acid 40. This acid may be reduced to the alcohol, and subsequent treatment with DPPA converts the alcohol to the corresponding azide 41. Catalytic hydrogenation, or a number of other known methodologies, can be employed to reduce both the nitro and azido moieties to give the corresponding diamine 42.

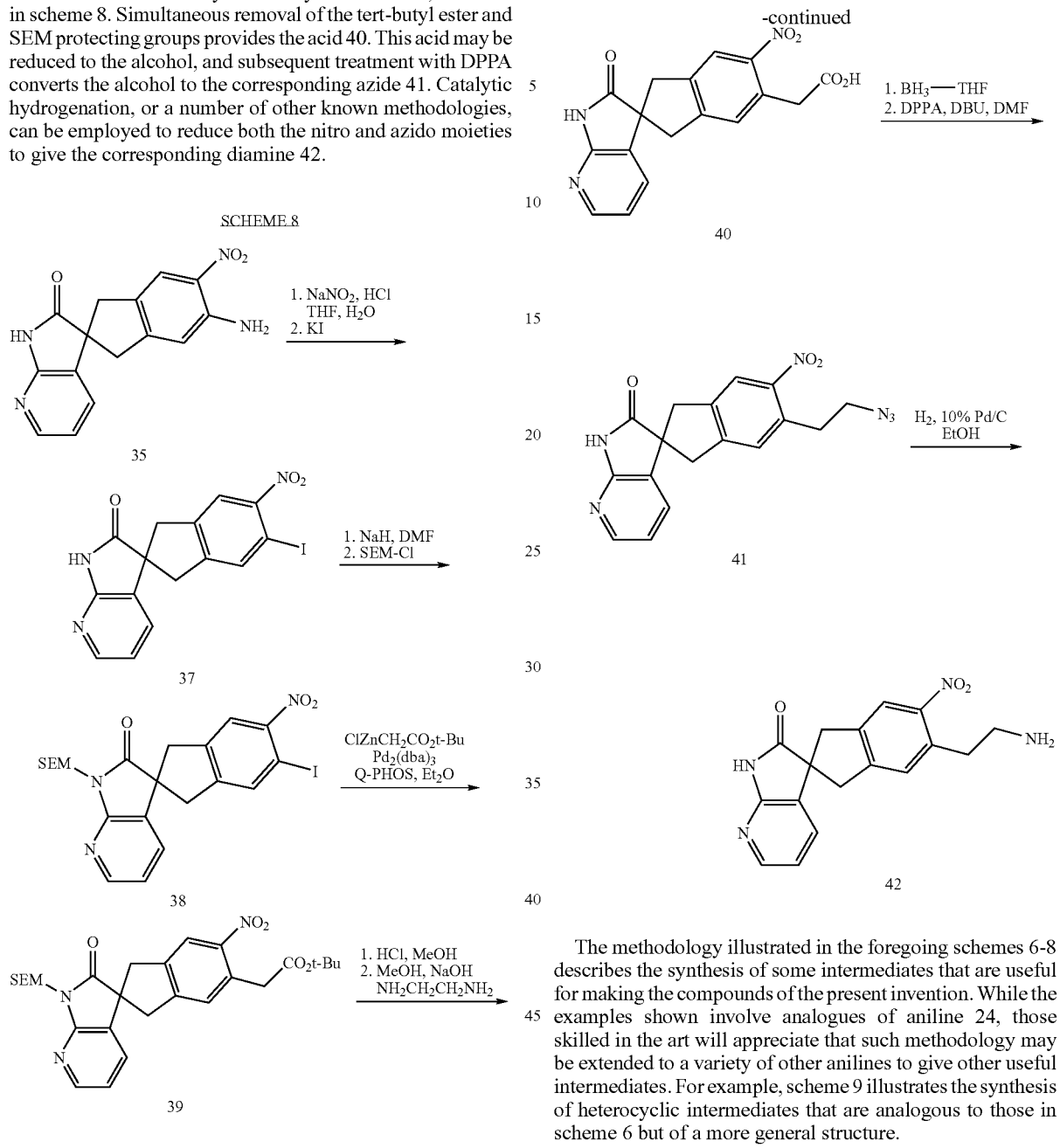

The methodology illustrated in the foregoing schemes 6-8 describes the synthesis of some intermediates that are useful for making the compounds of the present invention. While the examples shown involve analogues of aniline 24, those skilled in the art will appreciate that such methodology may be extended to a variety of other anilines to give other useful intermediates. For example, scheme 9 illustrates the synthesis of heterocyclic intermediates that are analogous to those in scheme 6 but of a more general structure.

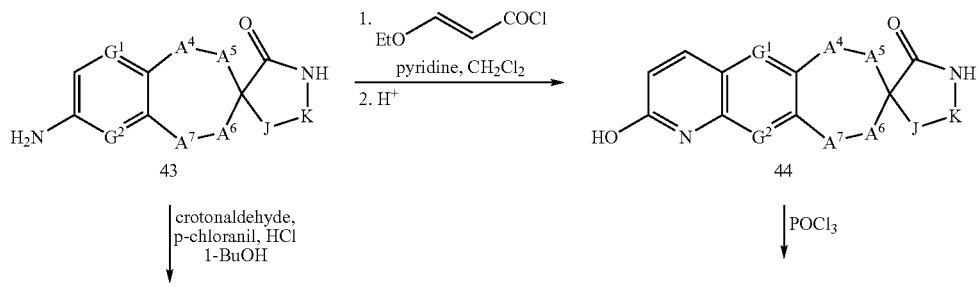

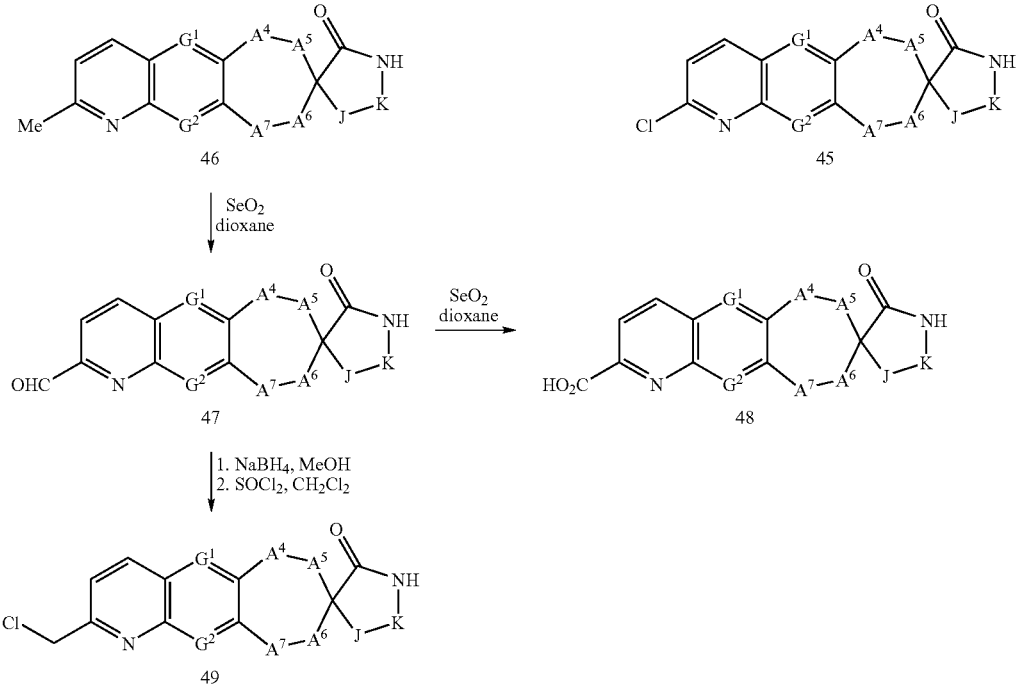

It is understood by those skilled in the art that in some cases alternative reagents or conditions may be used to effect the transformations in scheme 9. In some cases, additional chemical steps may be required to obtain the compounds of interest, or various protecting group strategies may be employed.

The intermediates described in schemes 6-9 may be used to synthesize the compounds of the present invention using a variety of known methodologies. Some of these methodologies are illustrated in scheme 10. Standard reductive amination of an aldehyde like 47 with a suitable amine (RR'NH) may be used to obtain a final product of interest (50). Similarly, a standard coupling reaction may be used to convert carboxylic acid 48 to amide 51, which may be another example of the present invention when R and R' are selected appropriately.

SCHEME 10

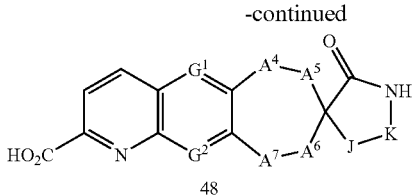

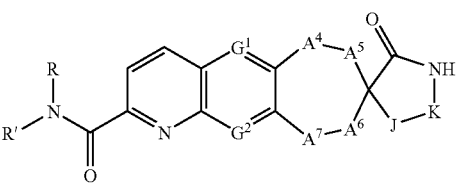

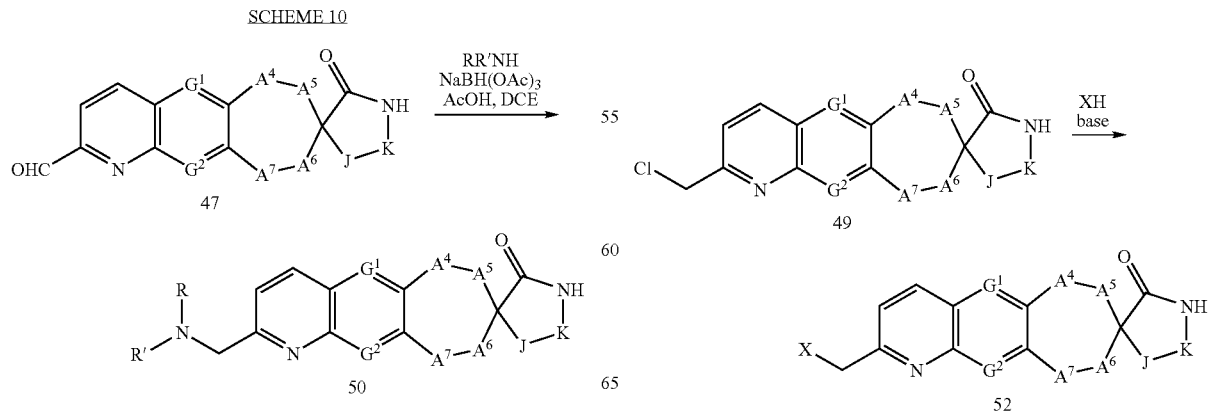

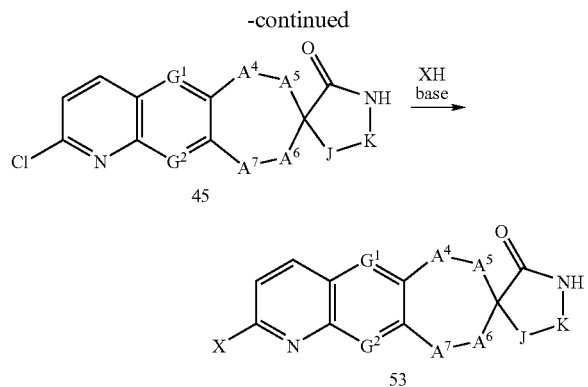

Scheme 10 also illustrates the coupling of chlorides 45 and 49 with a suitable partner (XH), usually under basic conditions, to give other compounds of the present invention (52 and 53). The precise nature of RR'NH or XH not only determines the identity of the final compound of interest, but also influences the choice of conditions under which the reaction is performed. For example, reductive amination of 47 may be performed using alternative conditions to those shown in scheme 10, such as sodium cyanoborohydride in MeOH, depending on the exact natures of 47 and the amine. Similarly, the coupling of RR'NH and acid 48 may be carried out under a variety of known conditions, such as use of an alternative coupling reagent like PyBOP, or activation of the carboxylic acid as an acid anhydride or acid chloride. One skilled in the art will infer from precedent in the chemical literature, and from those examples given herein, suitable conditions for reaction of either 45 or 49 with XH, which is usually an amine, lactam or similar compound.

SCHEME 11

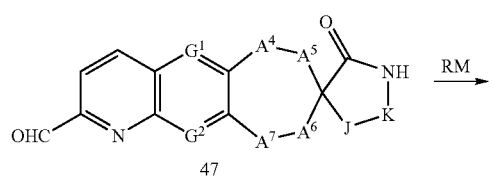

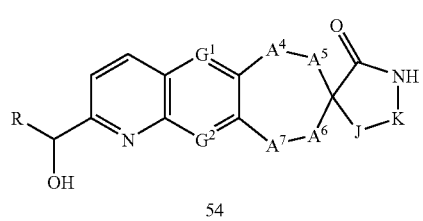

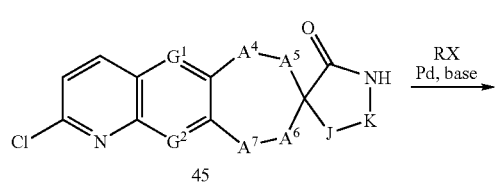

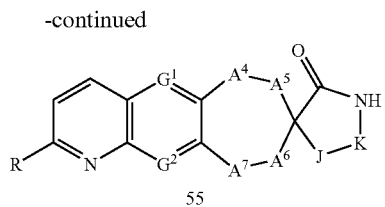

In some cases, compounds of the present invention may be obtained by use of the methodology shown in scheme 11. Reaction of aldehyde 47 with an appropriate organometallic species (RM), such as a Grignard reagent RMgBr, may be used to give alcohol 54. A wide variety of known coupling reactions that employ transition metal catalysts may also be used to couple chloride 45 to a suitable partner RX to give 55. Depending upon the nature of the desired product 55, RX may be chosen from a variety of useful coupling partners, such as boronic acids, halides, or organometallic reagents. In scheme 11, a palladium catalyst is used but alternatives such as nickel catalysts may also provide the compounds of interest. A variety of ligands may be utilized with such metal catalysts, as described in the literature.

Scheme 12 demonstrates how some other heterocyclic structures may be obtained from diamine precursors. The phenylenediamine 56 can be coupled to an acid RCO$_2$H using well known coupling reagents, such as BOP, to give an anilide intermediate which may be cyclized in situ under acidic conditions to give the benzimidazole 57. The same starting material 56 can be condensed with a suitable ketoaldehyde, as shown in scheme 12, to give the quinoxaline product 58. The required ketoaldehyde may be synthesized using known methodology. It may be a derivative of one of the coupling partners described herein, or subsequent functionalization after quinoxaline formation may be required to provide the desired compound of the present invention. Other ring sizes may also be obtained. For example, diamine 59 reacts readily with a variety of imidate esters to afford dihydrobenzodiazepine products of structure 60. The requisite imidate ester intermediate may be obtained using known methodology, such as treatment of the corresponding nitrile with an alcohol under acidic conditions.

SCHEME 12

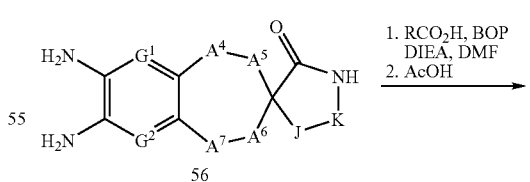

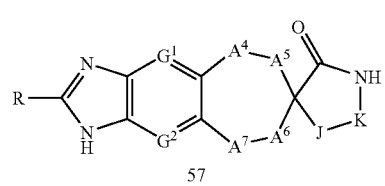

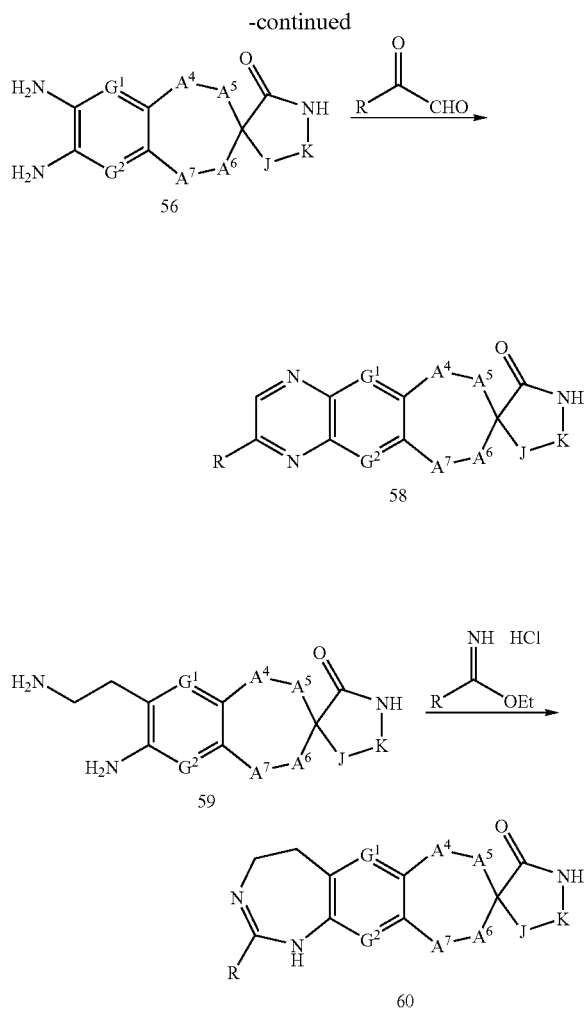

In schemes 10-12, a number of strategies for assembling the compounds of the present invention are illustrated. It is understood that alternative methodologies may also be employed in the synthesis of compounds of interest. The exact choice of reagents, solvents, temperatures, and other reaction conditions, depends upon the nature of the intended product. In some cases, appropriate protecting group strategies may be used. In other cases, further elaboration of the product shown in schemes 10-12 may be required to obtain the compound of the present invention. As previously stated, the identity of the coupling partner (e.g. RR'NH, XH, or RCO$_2$H) in schemes 10-12 must be chosen appropriately to give the compounds of the present invention.

Most of the coupling partners used to make the compounds of the present invention are readily available. They may be obtained from commercial sources or synthesized by methodology familiar to those skilled in the art and as described in the chemical literature.

Aniline intermediates, such as those described in schemes 1-5, may be converted to a variety of other key intermediates that are useful in the synthesis of the compounds of the present invention. For example, scheme 13 illustrates methodology for conversion of a representative aniline into a quinoline intermediate.

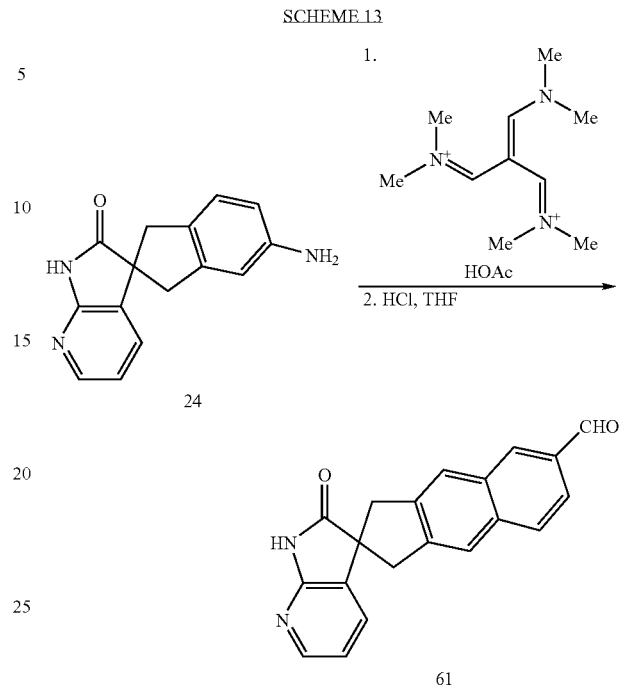

Aniline 24 may be converted to the corresponding aldehyde 61 by treatment with 2-dimethylaminomethylene-1,3-bis(dimethylimmonio)propane bis(tetrafluoroborate) according to the known procedure (Tom et al., *Synthesis*, 2001, 9, 1351). While the methodology shown in scheme 13 is exemplified using aniline 24, it is understood that it may be applied to a variety of aniline substrates, such as those described herein, in order to provide various quinoline intermediates. For example, scheme 14 illustrates the synthesis of heterocyclic intermediates that are analogous to those in scheme 13 but of a more general structure.

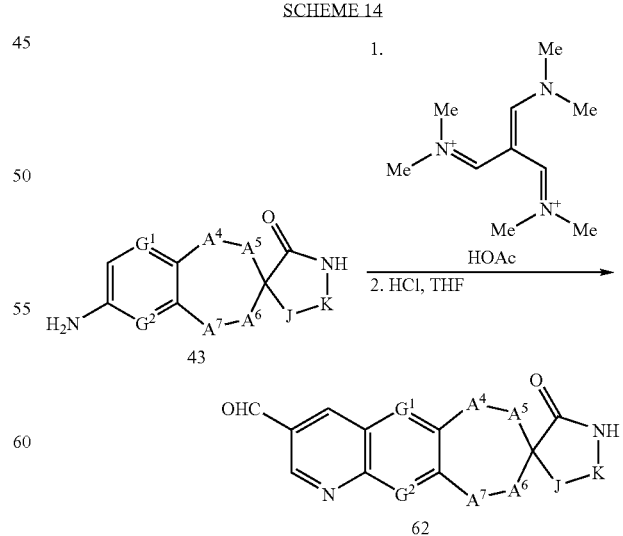

It is understood by those skilled in the art that in some cases alternative reagents or conditions may be used to effect the transformations in scheme 14. In some cases, additional chemical steps may be required to obtain the compounds of interest, or various protecting group strategies may be employed.

The intermediates described in scheme 14 may be used to synthesize the compounds of the present invention using a variety of known methodologies. One of these methodologies is illustrated in scheme 15. Standard reductive amination of an aldehyde like 62 with a suitable amine (RR'NH) may be used to obtain a final product of interest (63).

SCHEME 15

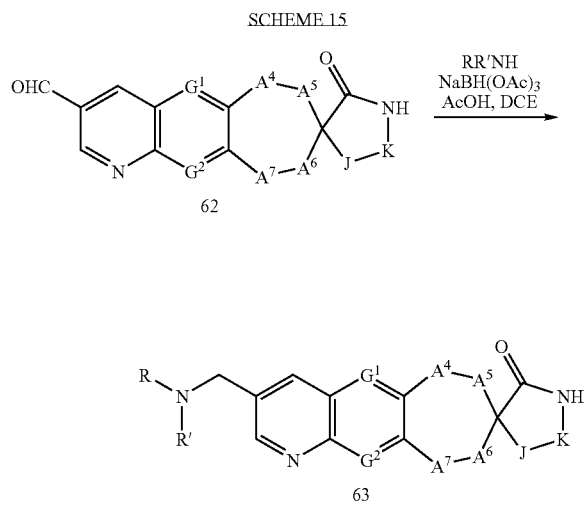

The precise nature of RR'NH not only determines the identity of the final compound of interest, but also influences the choice of conditions under which the reaction is performed. For example, reductive amination of 62 may be performed using alternative conditions to those shown in scheme 15, such as sodium cyanoborohydride in MeOH, depending on the exact natures of 62 and the amine.

In scheme 15, a representative strategy for assembling the compounds of the present invention is illustrated. It is understood that alternative methodologies may also be employed in the synthesis of compounds of interest. The exact choice of reagents, solvents, temperatures, and other reaction conditions, depends upon the nature of the intended product. In some cases, appropriate protecting group strategies may be used. In other cases, further elaboration of the product shown in scheme 15 may be required to obtain the compound of the present invention. As previously stated, the identity of the coupling partner (e.g. RR'NH) in scheme 15 must be chosen appropriately to give the compounds of the present invention.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

Intermediate 1

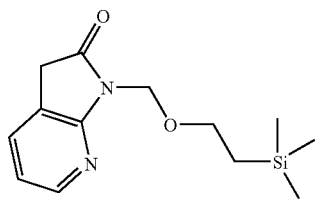

1-{[2-(Trimethylsilyl)ethoxy]methyl}-1,3-dihydro-2H-pyrrolo[2,3-b]pyridin-2-one

Step A. 1-{[2-Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with $H_2O$ (500 mL) and the mixture was extracted with $CH_2Cl_2$ (5×300 mL). The combined organic layers were washed with brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with $H_2O$ (300 mL) and extracted with EtOAc. The aqueous layer was washed with EtOAc (2×300 mL) and the combined organic layers were washed with $H_2O$ (4×300 mL; the final wash was pH 5-6), then brine (300 mL), then dried over $MgSO_4$, filtered and concentrated under reduced pressure. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one from Step B (65 g, 0.154 mol) in THF (880 mL) and saturated aqueous ammonium chloride (220 mL). After 3 h, the reaction was filtered and concentrated in vacuo. The residue was partitioned between EtOAc and H₂O which resulted in the formation of a white precipitate. Both layers were filtered through a Celite pad and the layers were separated. The aqueous layer was washed with EtOAc (2×) and the combined organic layers were washed with H₂O, dried over MgSO₄, filtered, and concentrated. The crude product was filtered through 5a plug of silica gel eluting with EtOAc:CH₂Cl₂—1:9 and the eluant was concentrated under reduced pressure to provide the title compound. MS: m/z=265 (M+1).

Intermediate 2

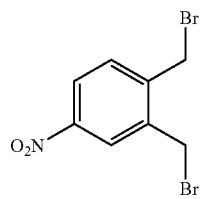

1,2-Bis(bromomethyl)-4-nitrobenzene

Step A. (4-Nitro-1,2-phenylene)dimethanol

4-Nitrophthalic acid (40 g, 189.5 mmol) in tetrahydrofuran (500 mL) was added dropwise over 1.5 h to a solution of borane-THF complex (1 M, 490 mL, 490 mmol), keeping the reaction temperature between 0° C. and 5° C. After the addition, the reaction was allowed to warm slowly to ambient temperature and stirred for 18 h. Methanol (100 mL) was added carefully and the precipitated solid dissolved. The mixture was concentrated in vacuo to about 500 mL, cooled to 0° C., and 10 N sodium hydroxide was added to adjust the pH to 10-11. This mixture was extracted with EtOAc (3×600 mL) and the combined organic layers were washed with brine, dried over Na₂SO₄, filtered, and concentrated in vacuo to give the title compound. MS: m/z=207 (M–OH+CH₃CN).

Step B. 1,2-Bis(bromomethyl)-4-nitrobenzene

Phosphorus tribromide (3.9 mL, 41.1 mmol) in ether (50 mL) was added dropwise over 1.5 h to a solution of (4-nitro-1,2-phenylene)dimethanol from Step A (6.85 g, 37.4 mmol) in ether (150 mL). After 18 h, the reaction mixture was cooled to 0° C. and quenched with H₂O (25 mL). The layers were separated and the organic layer was washed with H₂O, then saturated aqueous NaHCO₃, dried over Na₂SO₄, filtered, and concentrated in vacuo to give the title compound. MS: m/z=309 (M+1).

Intermediate 3

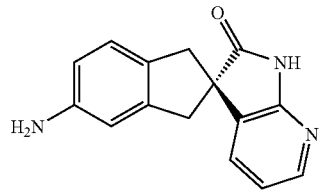

(S)-5-Amino-1,3-dihydrospiro[indene-2,3'-pyrrolo[2,3-b]pyridin]-2'(1'H)-one

Step A. (±)-5-Nitro-1'-{[2-(trimethylsilyl)ethoxy]methyl}-1,3-dihydrospiro[indene-2,3'-pyrrolo[2,3-b]pyridin]-2'(1'H1-one To a solution of 1,2-bis(bromomethyl)-4-nitrobenzene (40.9 g, 132 mmol, described in Intermediate 2) and 1-{[2-(trimethylsilyl)ethoxy]methyl}-1,3-dihydro-2H-pyrrolo[2,3-b]pyridin-2-one (31.5 g, 119 mmol, described in Intermediate 1) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and H₂O (1 L). The organic layer was washed with H₂O (1 L), then brine (500 mL), then dried over Na₂SO₄, filtered, and concentrated in vacuo. The crude product was purified by silica gel chromatography, eluting with a gradient of hexane:EtOAc—100:0 to 0:100, to give the title compound. MS: m/z=412 (M+1).

Step B. (S)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step A (19.1 g, 46.4 mmol) was stirred vigorously in EtOH (400 mL) under an atmosphere of hydrogen (cd. 1 atm). After 18 h, the mixture was filtered through a pad of Celite, washing extensively with MeOH, and the filtrate was concentrated in vacuo to give the crude racemic compound. The enantiomers were resolved by HPLC, utilizing a Chiralcel OD column and eluting with MeOH. The first major peak to elute was (S)-5-amino-1'-{[2-(trimethylsilyl)ethoxy]methyl}-1,3-dihydrospiro[indene-2,3'-pyrrolo[2,3-b]pyridin]-2'(1'H)-one, the title compound, and the second major peak to elute was (R)-5-amino-1'-{[2-(trimethylsilyl)ethoxy]methyl}-1,3-dihydrospiro[indene-2,3'-pyrrolo[2,3-b]pyridin]-2'(1'H)-one. MS: m/z=382 (M+1).

Step C. (S)-5-Amino-1,3-dihydrospiro[indene-2,3'-pyrrolo[2,3-b]pyridin]-2'(1'H)-one A solution of (S)-5-amino-1'-{[2-(trimethylsilyl)ethoxy]methyl}-1,3-dihydrospiro[indene-2,3'-pyrrolo[2,3-b]pyridin]-2'(1'H)-one from Step B (13.7 g, 35.9 mmol) in methanol (300 mL) was saturated with HCl (g). The mixture was resaturated with HCl (g) every 30 min until the starting material was consumed, and then concentrated in vacuo. The residue was dissolved in MeOH (150 mL) and treated with ethylenediamine (2.4 mL, 35.9 mmol) and 10 N sodium hydroxide (7.2 mL, 72 mmol) to adjust the mixture to pH 10. After 30 min, the mixture was diluted with H$_2$O (400 mL) and extracted with CHCl$_3$ (2×1 L). The combined organic layers were dried over Na$_2$SO$_4$, filtered, and concentrated in vacuo. The crude material was triturated with MeOH (50 mL) to give the title compound. MS: m/z=252 (M+1).

Intermediate 4

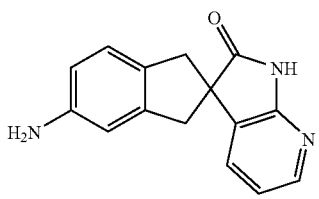

(±)-5-Amino-1,3-dihydrospiro[indene-2,3'-pyrrolo[2,3-b]pyridin]-2'(1'H)-one

Essentially following the procedures described for Intermediate 3, but without the chiral HPLC resolution of (±)-5-amino-1'-{[2-(trimethylsilyl)ethoxy]methyl}-1,3-dihydrospiro[indene-2,3'-pyrrolo[2,3-b]pyridin]-2'(1'H)-one, the title compound was obtained. MS: m/z=252 (M+1).

Intermediate 5

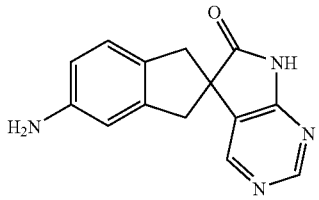

(±)-5-Amino-1,3-dihydrospiro[indene-2,5'-pyrrolo[2,3-d]pyrimidin]-6'(7'H)-one

Step A. 5,5-Dibromo-4-chloro-5,7-dihydro-6H-pyrrolo[2,3-d]pyrimidin-6-one

Pyridine hydrobromide perbromide (15.6 g, 48.8 mmol) was added in three portions to a stirred solution of 6-chloro-7-deazapurine (2.5 g, 16.3 mmol) at 40° C. in tert-butanol (100 mL). After 3 h, an additional amount of pyridine hydrobromide perbromide (5.19 g, 16.3 mmol) was added. After a further 2 h, the reaction mixture was concentrated in vacuo and partitioned between EtOAc and H$_2$O. The aqueous solution was extracted with EtOAc (2×) and the combined organic layers were washed with H$_2$O, dried over Na$_2$SO$_4$, filtered, and concentrated in vacuo to give the title compound. MS: m/z=328 (M+1).

Step B. 4-Chloro-5,7-dihydro-6H-pyrrolo[2,3-d]pyrimidin-6-one

Zinc (6.05 g, 92.56 mmol) was added to a solution of 5,5-dibromo-4-chloro-5,7-dihydro-6H-pyrrolo[2,3-d]pyrimidin-6-one from Step A (3.03 g, 9.26 mmol) in THF (20 mL) and saturated aqueous ammonium chloride (5 mL). After 3 h, the reaction mixture was concentrated in vacuo and purified by HPLC using a reversed phase C18 column and eluting with a gradient of H$_2$O:CH$_3$CN:CF$_3$CO$_2$H—90:10:0.1 to 5:95:0.1. Lyophilization provided the title compound. MS: m/z=170 (M+1).

Step C. (±)-4'-Chloro-5-nitro-1,3-dihydrospiro[indene-2,5'-pyrrolo[2,3-d]pyrimidin]-6'(7'H)-one Butyllithium (2.5 M in hexanes, 0.29 ml, 0.74 mmol) was added to a stirred solution of 4-chloro-5,7-dihydro-6H-pyrrolo[2,3-d]pyrimidin-6-one from Step B (50 mg, 0.295 mmol) at −78° C. in THF (30 mL). After complete addition of butyllithium, N,N,N',N'-tetramethylethane-1,2-diamine (0.31 mL, 0.77 mmol) was added. After 1 h at −78° C., 1,2-bis(bromomethyl)-4-nitrobenzene (91 mg, 0.295 mmol, described in Intermediate 2) was added and the reaction warmed to ambient temperature. After 8 h, the reaction was quenched with H$_2$O and the mixture was partitioned between EtOAc and H$_2$O. The aqueous solution was extracted with EtOAc (3×20 mL). The combined organic extracts were washed with brine (100 mL), dried over Na$_2$SO$_4$, filtered, and concentrated in vacuo to give the title compound.
MS: m/z=317 (M+1).

Step D. (±)-5-Amino-1,3-dihydrospiro[indene-2,5'-pyrrolo[2,3-d]pyrimidin]-6'(7'H)-one To a solution of (±)-4'-chloro-5-nitro-1,3-dihydrospiro[indene-2,5'-pyrrolo[2,3-d]pyrimidin]-6'(7'H)-one from Step C (400 mg, 1.26 mmol) in EtOAc (40 mL) and MeOH (10 mL) was added triethylamine (0.88 mL, 6.315 mmol). The mixture was hydrogenated at 50 psi hydrogen over 10% Pd/C (100 mg). After 24 h and 90 h, an additional amount of palladium on carbon (100 mg) was added to the reaction mixture and hydrogenation was continued for a total of 180 h. The reaction mixture was filtered through a pad of Celite and concentrated in vacuo. The residue was purified by HPLC using a reversed phase C18 column and eluting with a gradient of H$_2$O:CH$_3$CN:CF$_3$CO$_2$H—90:10:0.1 to 5:95:0.1. Lyophilization provided the title compound. MS: m/z=253 (M+1).

Intermediate 6

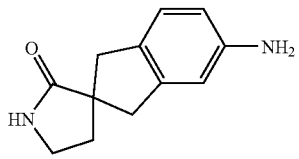

(±)-5-Amino-1,3-dihydro-2'H-spiro[indene-2,3'-pyrrolidin]-2'-one

Step A. Ethyl 2-allylindane-2-carboxylate

To a solution of ethyl indane-2-carboxylate [Schaaf et al., J. Med. Chem. 1983, 26, 328-334] (6.87 g, 36.1 mmol) in THF (100 mL) at −78° C. was added sodium bis(trimethylsilyl) amide (1.0 M in THF, 39.7 mL, 39.7 mmol) dropwise over 20 min. The resulting yellow solution was stirred for 1 h, and then allyl bromide (3.75 mL, 43.3 mmol) was added over 5 min. Stirring was continued for 1.5 h at −78° C., and then the reaction was quenched by the addition of saturated NH$_4$Cl and warmed to ambient temperature. The reaction mixture was partitioned between saturated NH$_4$Cl (100 mL) and EtOAc (100 mL). The aqueous phase was further extracted with EtOAc (2×50 mL), and the combined organic layers were dried over Na$_2$SO$_4$, filtered, and concentrated under reduced pressure. The crude product was purified by silica gel chromatography, eluting with a gradient of hexane:EtOAc— 100:0 to 75:25, to give the title compound. MS: m/z=231 (M+1).

Step B. Ethyl 2-(2-oxoethyl)indane-2-carboxylate

Ethyl 2-allylindane-2-carboxylate from Step A (3.00 g, 13.0 mmol) was dissolved in CH$_2$Cl$_2$ (100 mL) and cooled to −78° C. Ozone was bubbled through the solution for 15 min, at which time a light blue color persisted. Triethylamine (3.63 mL, 26.1 mmol) was added and the reaction mixture was stirred at ambient temperature for 1.5 h. The reaction mixture was partitioned between saturated NaHCO$_3$ (100 mL) and CH$_2$Cl$_2$ (100 mL). The aqueous phase was further extracted with CH$_2$Cl$_2$ (2×50 mL), and the combined organic layers were dried over Na$_2$SO$_4$, filtered, and concentrated under reduced pressure to give the title compound. MS: m/z=233 (M+1).

Step C. 1,3-Dihydro-2'H-spiro[indene-2,3'-pyrrolidin]-2'-one

Ethyl 2-(2-oxoethyl)indane-2-carboxylate from Step B (3.03 g, 13.0 mmol) and ammonium acetate (50.2 g, 651 mmol) were stirred in AcOH (20 mL) and MeOH (20 mL) at ambient temperature for 4 h, then sodium cyanoborohydride (1.29 g, 19.5 mmol) was added and stirring continued for 16 h. The reaction mixture was concentrated in vacuo and partitioned between saturated NaHCO$_3$ (50 mL) and CH$_2$Cl$_2$ (50 mL). The aqueous phase was further extracted with CH$_2$Cl$_2$ (2×25 mL), and the combined organic layers were dried over Na$_2$SO$_4$, filtered, and concentrated under reduced pressure to yield a yellow oil. The crude oil was heated to reflux in toluene (100 mL) for 1.5 h and then concentrated in vacuo. The crude product was purified by silica gel chromatography, eluting with a gradient of CH$_2$Cl$_2$:MeOH—100:0 to 90:10, to give the title compound. MS: m/z=188 (M+1).

Step D. (±)-5-Nitro-1,3-dihydro-2'H-spiro[indene-2, 3'-pyrrolidin]-2'-one

To 1,3-dihydro-2'H-spiro[indene-2,3'-pyrrolidin]-2'-one from Step C (114 mg, 0.609 mmol), cooled in an ice bath, was added 70% HNO$_3$ (5 mL). The reaction mixture was stirred for 45 min, diluted with water (10 mL), and extracted with CH$_2$Cl$_2$ (3×10 mL). The combined organic layers were dried over Na$_2$SO$_4$, filtered, and concentrated under reduced pressure. The crude product was purified by silica gel chromatography, eluting with a gradient of CH$_2$Cl$_2$:EtOAc—100:0 to 50:50, to give the title compound. MS: m/z=233 (M+1).

Step E. (±)-5-Amino-1,3-dihydro-2'H-spiro[indene-2,3'-pyrrolidin]-2'-one

To a solution of (±)-5-nitro-1,3-dihydro-2'H-spiro[indene-2,3'-pyrrolidin]-2'-one from Step D (97.0 mg, 0.418 mmol) in MeOH (5 mL) was added 10% Pd/C (15 mg). The reaction mixture was stirred under a hydrogen atmosphere (ca. 1 atm) for 1.5 h, then filtered through a Celite pad and concentrated under reduced pressure to give the title compound. MS: m/z=203 (M+1).

Intermediate 7

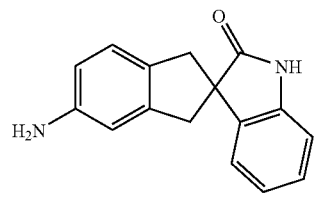

(±)-5-Amino-1,3-dihydrospiro[indene-2,3'-indol]-2' (1'H)-one

Step A. (±)-5-Bromo-1,3-dihydrospiro[indene-2,3'-indol]-2'(1')-one

To a solution of oxindole (363 mg, 2.73 mmol) at −78° C. in THF (15 mL) was added butyllithium (2.5 M in hexanes, 2.29 mL, 5.73 mmol) dropwise, followed by the dropwise addition of tetramethylethylenediamine (0.905 mL, 6.00 mmol). The solution was stirred for 1 h at −78° C., then a solution of 4-bromo-1,2-bis(bromomethyl)benzene [Anderson et al., *J. Org. Chem.* 1979, 44(9), 1519-1533] (1.87 g, 5.45 mmol) in THF (5 mL) was added dropwise. The reaction solution was stirred at −10 to −20° C. for 2 h and at ambient temperature for 16 h. The reaction mixture was partitioned between saturated NH$_4$Cl (50 mL) and EtOAc (50 mL). The aqueous phase was further extracted with EtOAc (2×50 mL), and the combined organic layers were dried over Na$_2$SO$_4$, filtered, and concentrated under reduced pressure. The crude product was purified by silica gel chromatography, eluting with a gradient of hexane:EtOAc—100:0 to 50:50, to give the title compound. MS: m/z=315 (M+1).

Step B. (i)-2'-Oxo-1,1',2',3-tetrahydrospiro[indene-2, 3'-indole]-5-carboxylic acid To a solution of (±)-5-bromo-1,3-dihydrospiro[indene-2, 3'-indol]-2'(1'H)-one from Step A (220 mg, 0.700 mmol) in THF (2 mL) was added ethylmagnesium bromide (3.0 M in ether, 0.467 mL, 1.40 mmol) dropwise, maintaining the reaction temperature<−60° C. Then tert-butyllithium (1.7 M in pentane, 1.65 mL, 2.80 mmol) was added dropwise, maintaining the reaction temperature<−60° C. The reaction solution was stirred for 5 min at −78° C., then CO$_2$(g) was bubbled through the solution for 15 min. Added H$_2$O (5 mL) and warmed to ambient temperature. The reaction mixture was partitioned between EtOAc (20 mL) and saturated NaHCO$_3$ (20 mL). The organic layer was further extracted with saturated NaHCO$_3$ (2×10 mL). The combined aqueous layers were washed with EtOAc (10 mL) and then acidified with 12 M HCl. The combined aqueous layers were extracted with $CH_2Cl_2$ (5×10 mL). A white precipitate formed that was insoluble in either layer, and was collected by filtration. The combined $CH_2Cl_2$ layers were dried over $Na_2SO_4$, filtered, and concentrated under reduced pressure. This crude product was combined with the recovered precipitate to give the title compound. MS: m/z=280 (M+1).

Step C. (±)-tert-Butyl (2'-oxo-1,1',2',3-tetrahydrospiro[indene-2,3'-indol]-5 µl carbamate A solution of (±)-2'-oxo-1,1',2',3-tetrahydrospiro[indene-2,3'-indole]-5-carboxylic acid from Step B (65.0 mg, 0.233 mmol), diphenylphosphoryl azide (0.060 mL, 0.279 mmol), and triethylamine (0.039 mL, 0.279 mmol) in t-BuOH (5 mL) was heated to reflux for 3 h. The reaction mixture was concentrated in vacuo. The crude product was purified by silica gel chromatography, eluting with a gradient of hexane:EtOAc—100:0 to 50:50, to give the title compound. MS: m/z=295 (M-$C_4H_7$).

Step D. (±)-5-Amino-1,3-dihydrospiro[indene-2,3'-indol]-2'(1'H)-one

HCl (g) was bubbled through a solution of (i)-tert-butyl (2'-oxo-1,1',2',3-tetrahydrospiro[indene-2,3'-indol]-5-yl) carbamate from Step C (19.0 mg, 0.054 mmol) in EtOAc (5 mL) for 15 min. The reaction mixture was stirred at ambient temperature for 1 h and then concentrated in vacuo to give the title compound. MS: m/z=251 (M+1).

Intermediate 8

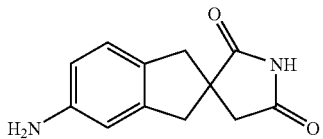

(±)-5-Amino-1,3-dihydro-2'H,5'H-spiro[indene-2,3'-pyrrolidine]-2',5'-dione

Step A. Ethyl 2-(2-tert-butoxy-2-oxoethyl)indane-2-carboxylate

To a solution of ethyl indane-2-carboxylate (Schaaf et al., J. Med. Chem. 1983, 26, 328-334) (2.00 g, 10.5 mmol) in THF at −78° C. was added sodium bis(trimethylsilyl)amide (15.8 mL of a 1.0 M solution in THF, 15.8 mmol) dropwise, over 10 min. The mixture was stirred for 15 min, then tert-butyl bromoacetate (3.08 g, 15.8 mmol) was added dropwise, over 30 min. The resulting mixture was stirred for 30 min at −78° C., then poured into brine (20 mL) and extracted with EtOAc (50 mL). The organic layer was dried over $Na_2SO_4$, filtered, and concentrated in vacuo. The crude product was purified by silica gel chromatography, eluting with a gradient of hexane:EtOAc—100:0 to 90:10, to give the title compound. MS: m/z=368 (M+Na+$CH_3CN$).

Step B. 2-(2-tert-Butoxy-2-oxoethyl)indane-2-carboxylic acid

A mixture of ethyl 2-(2-tert-butoxy-2-oxoethyl)indane-2-carboxylate from Step A (2.48 g, 8.15 mmol) and 1.0 N sodium hydroxide (8.96 mL, 8.96 mmol) in THF (50 mL), $H_2O$ (10 mL), and EtOH (20 mL) was stirred at ambient temperature for 18 h. The mixture was acidified with hydrochloric acid to about pH 3 and extracted with EtOAc (3×50 mL). The combined organic layers were dried over $Na_2SO_4$, filtered, and concentrated in vacuo, to give the title compound. MS: m/z=340 (M+Na+$CH_3CN$).

Step C. 2-(Carboxymethyl)indane-2-carboxylic acid

A solution of 2-(2-tert-butoxy-2-oxoethyl)indane-2-carboxylic acid from Step B (1.50 g, 5.43 mmol) in EtOAc (100 mL) was saturated with HCl (g) and stood at ambient temperature for 1b, then concentrated to dryness in vacuo, to give the title compound. MS: m/z=284 (M+Na+$CH_3CN$).

Step D. 1,3-Dihydro-2H,5'H-spiro[indene-2,3'-pyrrolidine]-2',5'-dione

A solution of 2-(carboxymethyl)indane-2-carboxylic acid from Step C (1.10 g, 4.99 mmol) in acetyl chloride (18 mL) was heated at reflux for 18 h, then concentrated in vacuo. The residue was recrystallized from toluene to give 1',3'-dihydrospiro[furan-3,2'-indene]-2,5(4H)-dione as an ivory solid. This solid was dissolved in $CH_2Cl_2$ (25 mL) and $NH_3$ (g) was bubbled into the mixture for 20 min. After a further 30 min, the solvent was evaporated under reduced pressure. The resulting solid was dried under high vacuum for 1 h, then resuspended in acetyl chloride (20 mL) and heated to reflux for 18 h. The solvent was removed in vacuo and the crude solid was recrystallized from EtOH:$Et_2O$ to afford the title compound. MS: m/z=202 (M+1).

Step E. (±)-5-Amino-1,3-dihydro-2'H,5'H-spiro[indene-2,3'-pyrrolidine]-2',5'-dione To a solution of 1,3-dihydro-2'H,5'H-spiro[indene-2,3'-pyrrolidine]-2',5'-dione from Step D (400 mg, 1.99 mmol) in $CF_3CO_2H$ (10 mL) was added sodium nitrite (411 mg, 5.96 mmol) and the mixture was heated to 55° C. for 2 h. The mixture was cooled and diluted with $H_2O$ (10 mL), then extracted with EtOAc (2×30 mL). The combined organic layers were dried over $Na_2SO_4$, filtered, and concentrated in vacuo, to give (±)-5-nitro-1,3-dihydro-2'H,5'H-spiro[indene-2,3'-pyrrolidine]-2',5'-dione, which contained some of the isomeric (±)-4-nitro-1,3-dihydro-2'H,5'H-spiro[indene-2,3'-pyrrolidine]-2',5'-dione. This solid was dissolved in EtOH (30 mL), then AcOH (0.55 mL) and 10% Pd/C (55 mg) were added. The mixture was stirred vigorously under an atmosphere of hydrogen (ca. 1 atm) for 2 h, then filtered through a pad of Celite, and concentrated in vacuo. The crude product was purified by silica gel chromatography, eluting with a gradient of $CH_2Cl_2$:EtOAc—95:5 to 10:90, to give the title compound. MS: m/z=217 (M+1).

Intermediate 9

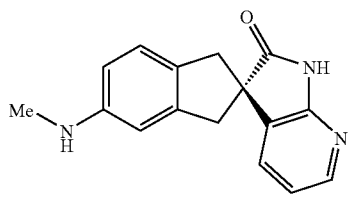

(S)-5-(Methylamino)-1,3-dihydrospiro[indene-2,3'-pyrrolo[2,3-b]pyridin]-2'(1'H)-one A mixture of (S)-5-amino-1,3-dihydrospiro[indene-2,3'-pyrrolo[2,3-b]pyridin]-2'(1'H)-one (154 mg, 0.613 mmol, described in Intermediate 3) and 1-(hydroxymethyl)benzotriazole (93 mg, 0.625 mmol) in EtOH (2 mL) and DMF (0.2 mL) was heated at reflux for 4 h, then concentrated to dryness under reduced pressure. The residue was resuspended in THF (3 mL) and sodium borohydride (40 mg, 1.05 mmol) was added. The resulting mixture was heated to 70° C. for 6 h then quenched with H$_2$O (50 mL) and extracted with EtOAc (50 mL). The organic extract was dried over Na$_2$SO$_4$, filtered, and concentrated in vacuo. The crude product was purified by silica gel chromatography, eluting with a gradient of CH$_2$Cl$_2$:MeOH—100:0 to 80:20, to give the title compound, which was of sufficient purity for use in the next step. MS: m/z=266 (M+1).

Intermediate 10

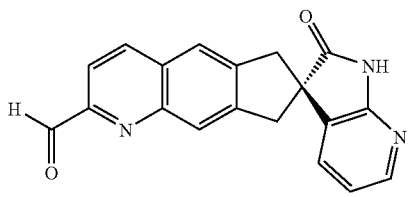

(S)-2'-Oxo-1',2',6,8-tetrahydrospiro[cyclopenta[g]-quinoline-7,3'-pyrrolo[2,3-b]pyridine]-2-carbaldehyde

Step A. (±)-2-Methyl-6,8-dihydrospiro[cyclopenta[g]quinoline-7,3'-pyrrolo[2,3-b]pyridin]-2'H)-one (S)-5-Amino-1,3-dihydrospiro[indene-2,3'-pyrrolo[2,3-b]pyridin]-2'(1'H)-one (6.10 g, 24.3 mmol, described in Intermediate 3) and p-chloranil (5.97 g, 24.3 mmol) were suspended in a mixture of 1-BuOH (6 mL) and conc. hydrochloric acid (6 mL, 73 mmol) and the mixture was heated to reflux. Crotonaldehyde (2.04 g, 29.1 mmol) in 1-BuOH (4 mL) was added dropwise over 20 min. After a further 20 min at reflux, the mixture was allowed to cool to ambient temperature and 10 N NaOH (7.3 mL, 73 mmol) was added and the neutralized mixture was concentrated in vacuo to give a brown residue. The crude product was purified by silica gel chromatography, eluting with a gradient of CH$_2$Cl$_2$:MeOH:NH$_4$OH—100:0:0 to 95:4.5:0.5, to give the title compound. MS: m/z=302 (M+1).

Step B. (S)-2'-Oxo-1',2',6,8-tetrahydrospiro[cyclopenta[g]quinoline-7,3'-pyrrolo[2,3-b]pyridine]-2-carbaldehyde A mixture of (S)-2-methyl-6,8-dihydrospiro[cyclopenta[g]quinoline-7,3'-pyrrolo[2,3-b]pyridin]-2'(1'H)-one from Step A (1.30 g, 4.31 mmol) and selenium dioxide (718 mg, 6.47 mmol) in dioxane (50 mL) and H$_2$O (5 mL) was heated at reflux for 4 h. The reaction mixture was concentrated to dryness under reduced pressure. The residue was purified by silica gel chromatography, eluting with a gradient of CH$_2$Cl$_2$:MeOH-100:0 to 90:10. Product-containing fractions were combined, toluene was added, and the mixture was concentrated in vacuo to give the title compound. MS: m/z=316 (M+1).

Intermediate 11

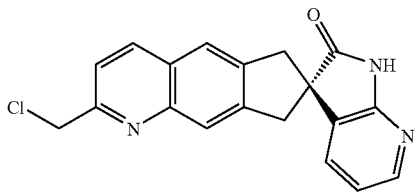

(S)-2-(Chloromethyl)-6,8-dihydrospiro[cyolopenta[g]quinoline-7,3'-pyrrolo[2,3-b]pyridin]-2'(1'H-one

Step 2 A. (S)-2-(Hydroxymethyl)-6,8-dihydrospiro[cyclopenta[g]quinoline-7,3'-pyrrolo[2,3-b]pyridin]-2'(1'H-one To a stirred suspension of (S)-2'-oxo-1',2',6,8-tetrahydrospiro[cyclopenta[g]quinoline-7,3'-pyrrolo[2,3-b]pyridine]-2-carbaldehyde (80 mg, 0.25 mmol, described in Intermediate 10) in a mixture of MeOH (5 mL) and DMSO (1 mL) was added sodium borohydride (19 mg, 0.51 mmol). The resulting mixture was stirred at ambient temperature for 1 h, then the MeOH was removed in vacuo. The residue was partitioned between saturated aqueous NaHCO$_3$ (20 mL) and CH$_2$Cl$_2$ (20 mL). The aqueous layer was extracted further with CH$_2$Cl$_2$ (2×20 mL). The combined organic extracts were dried over Na$_2$SO$_4$, filtered, and concentrated in vacuo to give the title compound in sufficient purity for use in the next step. MS: m/z=318 (M+1).

Step B. (M)-2-(Chloromethyl)-6,8-dihydrospiro[cyclopenta[g]quinoline-7,3'-pyrrolo[2,3-b]pyridin]-2'(1'H)-one To a stirred solution of (S)-2-(hydroxymethyl)-6,8-dihydrospiro[cyclopenta[g]quinoline-7,3'-pyrrolo[2,3-b]pyridin]-2'(1'H)-one from Step A (203 mg, 0.64 mmol) in CH$_2$Cl$_2$ (20 mL) was added thionyl chloride (761 mg, 6.40 mmol) and the resulting mixture was stirred at ambient temperature for 1 h, then concentrated in vacuo. The residue was partitioned between saturated aqueous NaHCO$_3$ (20 mL) and CH$_2$Cl$_2$ (30 mL). The aqueous layer was extracted further with CH$_2$Cl$_2$ (2×30 mL). The combined organic extracts were dried over Na₂SO₄, filtered, and concentrated in vacuo to give the title compound in sufficient purity for use in the next step. MS: m/z=336 (M+1).

Intermediate 12

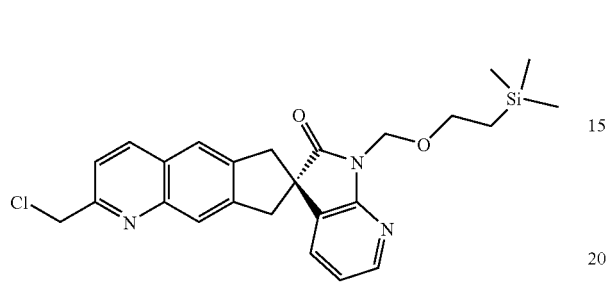

(S)-2-(Chloromethyl)-1'-{[2-(trimethylsilyl)ethoxy]
methyl}-6,8-dihydrospiro[cyclopenta[g]quinoline-7,
3'-pyrrolo[2,3-b]pyridin]-2'(1'H)-one Step A. (S)-2-(Hydroxymethyl)-1'-{[2-(trimethylsi-
lyl)ethoxy]methyl}-6,8-dihydrospiro[cyclopenta[g]
quinoline-7,3'-pyrrolo[2,3-b]pyridin]-2'(1'H)-one To a stirred solution of (S)-2-(hydroxymethyl)-6,8-dihydrospiro[cyclopenta[g]quinoline-7,3'-pyrrolo[2,3-b]pyridin]-2'(1'H)-one (1.67 g, 5.26 mmol, described in Intermediate 11) in DMF (10 mL) at 0° C. was added sodium hydride (60% dispersion in mineral oil; 210 mg, 5.26 mmol) and the mixture was stirred for 30 min. 2-(Trimethylsilyl)ethoxymethyl chloride (0.93 mL, 5.26 mmol) was then added dropwise. After 90 min, the reaction was quenched with saturated aqueous NaHCO₃ (50 mL) and the mixture was extracted with CH₂Cl₂ (3×100 mL). The combined organic layers were washed with brine, dried over Na₂SO₄, filtered, concentrated in vacuo. The crude product was purified by silica gel chromatography, eluting with a gradient of CH₂Cl₂:MeOH:NH₄OH—100:0:0 to 90:9:1, to give the title compound. MS: m/z=448 (M+1).

Step B. (S)-2-(Chloromethyl)-1'-{[2-(trimethylsilyl)
ethoxy]methyl}-6,8-dihydrospiro[cyclopenta[g]
quinoline-7,3'-pyrrolo[2,3-b]pyridin]-2'(1'H)-one To a stirred solution of (s)-2-(hydroxymethyl)-1'-{[2-(trimethylsilyl)ethoxy]methyl}-6,8-dihydrospiro[cyclopenta[g]quinoline-7,3'-pyrrolo[2,3-b]pyridin]-2'(1'H)-one from Step A (1.44 g, 3.22 mmol) in CH₂Cl₂ (10 mL) was added thionyl chloride (7.66 g, 64.3 mmol) and the resulting mixture was stirred at ambient temperature for 30 min, then concentrated in vacuo. The residue was concentrated in vacuo from toluene (2×10 mL) to give the title compound in sufficient purity for use in the next step.

MS: m/z=466 (M+1).

Intermediate 13

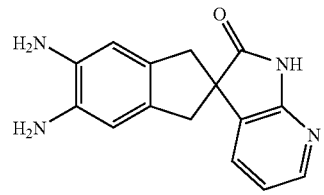

5,6-Diamino-1,3-dihydrospiro[indene-2,3'-pyrrolo[2,
3-b]pyridin]-2'(1')-one

Step A. (S)-5-Amino-6-nitro-1,3-dihydrospiro[in-
dene-2,3'-pyrrolo[2,3-b]pyridin]-2'(1'H)-one To a suspension of (R)-5-amino-1'-{[2-(trimethylsilyl) ethoxy]methyl}-1,3-dihydrospiro[indene-2,3'-pyrrolo[2,3-b]pyridin]-2'(1'H)-one (28.7 g, 75.2 mmol, described in Intermediate 3) in CH₂Cl₂ (100 mL) was added trifluoroacetic anhydride (106 mL, 752 mmol). The mixture was stirred for 10 min, after which time the aniline had been converted to the corresponding trifluoroacetanilide. The resulting mixture was cooled in an ice-salt bath and 15.8 M nitric acid (5.0 mL, 79 mmol) was added dropwise over 15 min, keeping the reaction temperature at 10-12° C. After the addition, the reaction mixture was stirred for 30 min, then H₂O (12 mL) was carefully added, followed by trifluoroacetic acid (100 mL) and CH₂Cl₂ (100 mL). The mixture was allowed to warm to ambient temperature and stirring was continued for 2 h, followed by concentration to dryness in vacuo. The residue was dissolved in MeOH (200 mL) and the solution was adjusted to pH 10 by addition of 10 N NaOH. Ethylene diamine (5 mL, 75 mmol) was added and the mixture was stirred at ambient temperature for 18 h, then diluted with H₂O (200 mL). The resulting solid was isolated by filtration, washed with H₂O, and dried in vacuo to give the title compound. MS: m/z=297 (M+1).

Step B. 5,6-Diamino-1,3-dihydrospiro[indene-2,3'-
pyrrolo[2,3-b]pyridin]-2'(1H)-one A mixture of 10% Pd/C (900 mg) and (S)-5-amino-6-nitro-1,3-dihydrospiro[indene-2,3'-pyrrolo[2,3-b]pyridin]-2' (1'H)-one from Step A (3.00 g, 10.11 mmol) was stirred vigorously in MeOH (500 mL) and EtOAc (700 mL) under an atmosphere of hydrogen (ca. 1 atm). After 18 h, the mixture was filtered through a pad of Celite, washing with MeOH, and the filtrate was concentrated in vacuo to give the title compound. MS: m/z=267 (M+1).

Intermediate 14

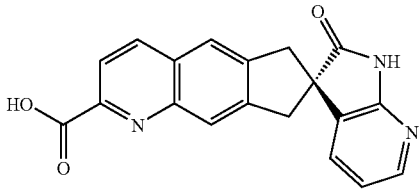

(S)-2'-Oxo-1',2',6,8-tetrahydrospiro[cyclopenta[g]
quinoline-7,3'-pyrrolo[2,3-b]pyridine]-2-carboxylic
acid

Step A. (S)-2'-Oxo-1',2',6,8-tetrahydrospiro[cyclopenta[g]quinoline-7,3'-pyrrolo[2,3-b]pyridine]-2-carboxylic acid A mixture of (S)-2-methyl-6,8-dihydrospiro[cyclopenta[g]quinoline-7,3'-pyrrolo[2,3-b]pyridin]-2'(1'H)-one (500 mg, 1.66 mmol, described in Intermediate 10) and selenium dioxide (552 mg, 4.97 mmol) in dioxane (30 mL) and H$_2$O (3 mL) was heated at reflux for 18 h. The reaction mixture was allowed to cool, then it was filtered through a pad of Celite, and the filtrate was concentrated in vacuo to give the title compound. MS: m/z=332 (M+1).

Intermediate 15

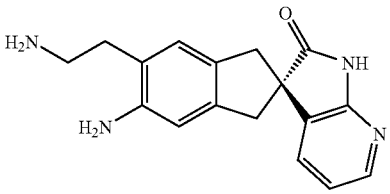

(2S-5-Amino-6-(2-aminoethyl)-1,3-dihydrospiro[indene-2,3'-pyrrolo[2,3-b]pyridin]-2'(1'H)-one

Step A. (2R)-5-Iodo-6-nitro-1,3-dihydrospiro[indene-2,3'-pyrrolo[2,3-b]pyridin]-2'(1'H)-one To a suspension of (S)-5-amino-6-nitro-1,3-dihydrospiro[indene-2,3'-pyrrolo[2,3-b]pyridin]-2'(1'H)-one (6.14 g, 20.7 mmol, described in Intermediate 13) in 3 N hydrochloric acid (50 mL) and THF (20 mL), at −5° C., was added NaNO$_2$ (1.60 g, 23.2 mmol) in H$_2$O (10 mL) dropwise at such a rate that the reaction temperature was maintained below 0° C. After a further 15 min, KI (9.2 g, 55 mmol) in H$_2$O (9 mL) was added dropwise over 30 min, keeping the reaction temperature below 0° C. After a further 15 min, the mixture was extracted with CH$_2$Cl$_2$ (3×300 mL), and the combined organic layers were dried over Na$_2$SO$_4$, decanted, and concentrated in vacuo. The crude product was purified by silica gel chromatography, eluting with a gradient of CH$_2$Cl$_2$:MeOH—100:0 to 90:10, to give the title compound, which was of sufficient purity for use in the next step. MS: m/z=408 (M+1).

Step B. (2R)-5-Iodo-6-nitro-1'-{[2-(trimethylsilyl)ethoxy]methyl}-1,3-dihydrospiro[indene-2,3'-pyrrolo[2,3-b]pyridin]-2'(1'H)-one Sodium hydride (60% dispersion in mineral oil; 525 mg, 13.1 mmol) was added to a solution of (2R)-5-iodo-6-nitro-1,3-dihydrospiro[indene-2,3'-pyrrolo[2,3-b]pyridin]-2'(1')-one from Step A (5.14 g, 12.6 mmol) in DMF (40 mL) at 0° C. and the mixture was stirred for 5 min. 2-(Trimethylsilyl)ethoxymethyl chloride (2.23 mL, 12.6 mmol) was then added dropwise, and the reaction mixture was stirred at 0° C. for 2 h. The reaction was quenched with dilute aqueous NaHCO$_3$ (200 mL) and the mixture was extracted with EtOAc (3×200 mL). The combined organic layers were washed with brine, dried over MgSO$_4$, filtered, and concentrated under reduced pressure. The crude product was purified by silica gel chromatography, eluting with a gradient of hexane:EtOAc—100:0 to 0:100, to give the title compound, which was of sufficient purity for use in the next step. MS: m/z=538 (M+1).

Step C. tert-Butyl ((2S)-6-nitro-2'-oxo-1'-{[2-(trimethylsilyl)ethoxy]methyl}-1,1', 2',3-tetrahydrospiro[indene-2,3'-pyrrolo[2,3-b]pyridin]-5-yl)acetate To a flask containing (2R)-5-iodo-6-nitro-1'-{[2-(trimethylsilyl)ethoxy]methyl}-1,3-dihydrospiro[indene-2,3'-pyrrolo[2,3-b]pyridin]-2'(1'.H)-one from Step B (4.02 g, 7.48 mmol), tris(dibenzylideneacetone)dipalladium (349 mg, 0.38 mmol), and 1,2,3,4,5-pentaphenyl-1'-(di-tert-butylphosphino)ferrocene (532 mg, 0.75 mmol) was added 2-tert-butoxy-2-oxoethylzinc chloride (Rieke, 0.5 M in Et$_2$O; 15.7 mL, 7.85 mmol) and the resulting solution was heated to 40° C. for 1 h. The reaction was quenched with dilute aqueous NaHCO$_3$ (100 mL) and the mixture was extracted with EtOAc (200 mL). The organic layer was washed with brine, dried over Na$_2$SO$_4$, filtered, and concentrated under reduced pressure. The crude product was purified by silica gel chromatography, eluting with a gradient of hexane:EtOAc—100:0 to 0:100, to give the title compound, which was of sufficient purity for use in the next step. MS: m/z=526 (M+1).

Step D. [(2S)-6-Nitro-2'-oxo-1,1',2',3-tetrahydrospiro[indene-2,3'-pyrrolo[2,3-b]pyridin]-5-yl]acetic acid A solution of tert-butyl ((2S)-6-nitro-2'-oxo-1'-{[2-(trimethylsilyl)ethoxy]methyl}-1,1',2',3-tetrahydrospiro[indene-2,3'-pyrrolo[2,3-b]pyridin]-5-yl)acetate from Step C (2.01 g, 3.83 mmol) in MeOH (25 mL) was saturated with HCl (g) and stood at ambient temperature for 18 h. The mixture was concentrated to dryness in vacuo, then redissolved in MeOH (25 mL). This stirred solution was adjusted to pH 10 with 10 N NaOH and ethylene diamine (0.26 mL, 3.83 mmol) was added. The resulting mixture was stirred for 3 h, then concentrated to dryness in vacuo. The residue was dissolved in THF (25 mL) and 1 N NaOH (25 mL, 25 mmol) was added. The mixture was stirred at ambient temperature for 18 h, then the THF was removed under reduced pressure. The residual mixture was partitioned between saturated aqueous NaHCO$_3$ (50 mL) and EtOAc (100 mL). The organic layer was discarded and the aqueous layer was adjusted to pH 2 with aqueous HCl, then extracted with EtOAc (3×200 mL). The combined organic layers were dried over Na$_2$SO$_4$, filtered, and concentrated under reduced pressure to give the title compound. MS: m/z=340 (M+1).

Step E. (2S)-5-(2-Hydroxyethyl)-6-nitro-1,3-dihydrospiro[indene-2,3'-pyrrolo[2,3-b]pyridin]-2'(1'H)-one To a stirred solution of [(2S)-6-nitro-2'-oxo-1,1',2',3-tetrahydrospiro[indene-2,3'-pyrrolo[2,3-b]pyridin]-5-yl]acetic acid from Step D (753 mg, 2.22 mmol) in THF (15 mL), at −78° C., was added borane (1 M in THF; 9.1 mL, 9.1 mmol) dropwise. After 5 min, the mixture was warmed to 0° C. and stirring was continued at this temperature for 3 h. The reaction was quenched carefully with 1 N HCl and stirring was continued at ambient temperature. The mixture was adjusted to pH 8 with saturated aqueous NaHCO₃ and extracted with EtOAc (2×100 mL). The combined organic layers were dried over Na₂SO₄, filtered, and concentrated under reduced pressure. The crude product was purified by silica gel chromatography, eluting with a gradient of CH₂Cl₂:MeOH—100:0 to 80:20, to give the title compound.

MS: m/z=326 (M+1).

Step F. (2S)-5-(2-Azidoethyl)-6-nitro-1,3-dihydrospiro[indene-2,3'-pyrrolo[2,3-b]pyridin]-2'(1'H)-one To a stirred solution of (2S)-5-(2-hydroxyethyl)-6-nitro-1,3-dihydrospiro[indene-2,3'-pyrrolo[2,3-b]pyridin]-2'(1'-one from Step E (174 mg, 0.54 mmol) in DMF (4 mL) were added diphenyl phosphoryl azide (177 mg, 0.64 mmol) and DBU (0.096 mL, 0.64 mmol). The mixture was heated at 100° C. for 6 h, then quenched with H₂O (20 mL) and extracted with EtOAc (50 mL). The organic layer was dried over Na₂SO₄, filtered, and concentrated under reduced pressure. The crude product was purified by silica gel chromatography, eluting with a gradient of CH₂Cl₂:MeOH—100:0 to 80:20, to give the title compound. MS: m/z=351 (M−1).

Step G. (2S)-5-Amino-6-(2-aminoethyl)-1,3-dihydrospiro[indene-2,3'-pyrrolo[2,3-b]pyridin]-2'(1'H)-one To a solution of (2S)-5-(2-azidoethyl)-6-nitro-1,3-dihydrospiro[indene-2,3'-pyrrolo[2,3-b]pyridin]-2'(1'H)-one from Step F (236 mg, 0.67 mmol) in EtOH (15 mL) was added 10% Pd/C (172 mg). The reaction mixture was stirred under a hydrogen atmosphere (ca. 1 atm) for 5 h, then filtered through a Celite pad, washing with MeOH, and the filtrate was concentrated under reduced pressure to give the title compound. MS: m/z/z 295 (M+1).

Intermediate 18

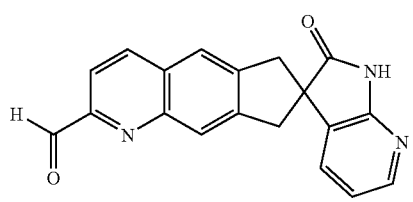

(±)-2'-Oxo-1',2',6,8-tetrahydrospiro[cyclopenta[g]quinoline-7,3'-pyrrolo[2,3-h]pyridine]-2-carbaldehyde Essentially following the procedures described for Intermediate 10, but using (±)-5-amino-1,3-dihydrospiro[indene-2,3'-pyrrolo[2,3-b]pyridin]-2'(1'H)-one (described in Intermediate 4) in place of (S)-5-amino-1,3-dihydrospiro[indene-2,3'-pyrrolo[2,3-b]pyridin]-2'(1'H)-one, the title compound was obtained. MS: m/z=316 (M+1).

Intermediate 19

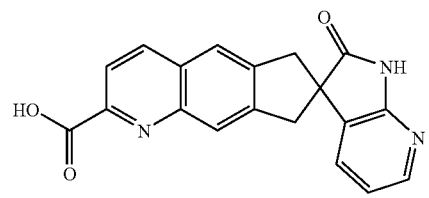

(±)-2'-Oxo-1',2',6,8-tetrahydrospiro[cyclopenta[g]quinoline-7,3'-pyrrolo[2,3-b]pyridine]-2-carboxylic acid Essentially following the procedures described for Intermediate 14, but using (±)-2-methyl-6,8-dihydrospiro[cyclopenta[g]quinoline-7,3'-pyrrolo[2,3-b]pyridin]-2'(1'H)-one (described in Intermediate 18) in place of (S)-2-methyl-6,8-dihydrospiro[cyclopenta[g]quinoline-7,3'-pyrrolo[2,3-b]pyridin]-2'(1'H)-one, the title compound was obtained. MS: m/z=332 (M+1).

Intermediate 20

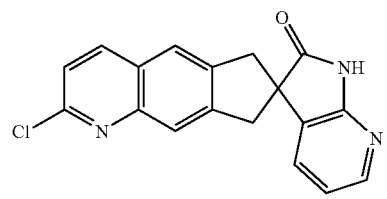

(±)-2-Chloro-6,8-dihydrospiro[cyclopenta[g]quinoline-7,3'-pyrrolo[2,3-b]pyridin]-2'(1'H)-one

Step A. (±)-(2E)-3-Ethoxy-N-(2'-oxo-1,1',2',3-tetrahydrospiro[indene-2,3'-pyrrolo[2,3-b]pyridin]-5-yl)acrylamide To a stirred suspension of (±)-5-amino-1,3-dihydrospiro[indene-2,3'-pyrrolo[2,3-b]pyridin]-2'(1'H)-one (3.06 g, 12.2 mmol, described in Intermediate 4) in CH₂Cl₂ (100 mL) and pyridine (40 mL) was added a solution of (E)-3-ethoxyacryloyl chloride [Tietze et al., *Synthesis*, 1993, 1079-1080] (1.64 g, 12.2 mmol) in CH₂Cl₂ (100 mL). The resulting mixture was stirred at ambient temperature for 1 h, then concentrated to dryness in vacuo. The residue was suspended in H₂O (350 mL) with sonication and the solid was isolated by filtration and dried to give the title compound. MS: m/z=350 (M+1).

Step B. (±)-2-Hydroxy-6,8-dihydrospiro[cyclopenta[g]quinoline-7,3'-pyrrolo[2,3-b]pyridin]-2(1'H)-one To stirred concentrated sulfuric acid (25 mL) at 0° C. was added (±)-(2E)-3-ethoxy-N-(2'-oxo-1,1',2',3-tetrahydrospiro[indene-2,3-pyrrolo[2,3-b]pyridin-5-yl)acrylamide from Step A (2.20 g, 6.30 mmol) portionwise. The resulting mixture was stirred at 0° C. for 10 min then poured onto ice and adjusted to pH=9 by careful addition of 10 N aqueous NaOH. The precipitate was isolated by filtration, washed with H$_2$O, and dried to give the title compound. MS: m/z=304 (M+1).

Step C. (±)-2-Chloro-6,8-dihydrospiro[cyclopenta[g]quinoline-7,3'-pyrrolo[2,3-b]pyridin]-2'(1'H)-one A solution of (±)-2-hydroxy-6,8-dihydrospiro[cyclopenta[g]quinoline-7,3'-pyrrolo[2,3-b]pyridin]-2'(1'H)-one from Step B (3.00 g, 9.89 mmol) in POCl$_3$ (30 mL) was stirred at 80° C. for 2 h, then concentrated to dryness under reduced pressure. The residue was partitioned between saturated aqueous NaHCO$_3$ (200 mL) and CH$_2$Cl$_2$ (500 mL). The aqueous layer was extracted further with CH$_2$Cl$_2$ (200 mL). The combined organic layers were dried over Na$_2$SO$_4$, filtered, and concentrated under reduced pressure to give the title compound. MS: m/z=322 (M+1).

Intermediate 21

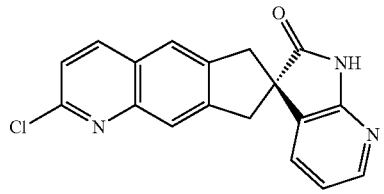

(7S)-2-Chloro-6,8-dihydrospiro[cyclopenta[g]quinoline-7,3'-pyrrolo[2,3-b]pyridin]-2'(1'H)-one Essentially following the procedures described for Intermediate 20, but using (s)-5-amino-1,3-dihydrospiro[indene-2,3'-pyrrolo[2,3-b]pyridin]-2'(1'H)-one (described in Intermediate 3) in place of (±)-5-amino-1,3-dihydrospiro[indene-2,3'-pyrrolo[2,3-b]pyridin]-2'(1'H)-one, the title compound was obtained. MS: m/z=322 (M+1).

Intermediate 22

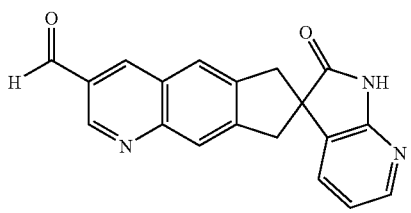

(±)-2'-Oxo-1',2',6,8-tetrahydrospiro[cyclopenta[g]quinoline-7,3'-pyrrolo[2,3-b]pyridine]-3-carbaldehyde (±)-5-Amino-1,3-dihydrospiro[indene-2,3'-pyrrolo[2,3-b]pyridin]-2'(1'H)-one (125 mg, 0.500 mmol, described in Intermediate 4) and 2-dimethylaminomethylene-1,3-bis(dimethylimmonio)propane bis(tetrafluoroborate) (266 mg, 0.750 mmol) were suspended in glacial acetic acid and the mixture was heated to reflux for 22 h. The mixture was allowed to cool to ambient temperature before the bulk of the acetic acid was removed in vacuo. THF (3 mL) and 1 N HCl (3 mL, 3 mmol) were added and the mixture was stirred at ambient temperature for 2 h. The mixture was then poured into a separatory funnel containing CHCl$_3$ (50 mL) and saturated aqueous NaHCO$_3$ (10 mL). The aqueous layer was extracted twice with CHCl$_3$ (2×250 mL) and the combined organic layers were dried over Na$_2$SO$_4$. Filtration to remove drying agent gave a solution which was concentrated in vacuo to give a yellow residue. The impure product was purified by silica gel chromatography, eluting with a gradient of CH$_2$Cl$_2$:MeOH—100:1 to 92:8, to give the title compound. MS: m/z=316 (M+1).

Intermediate 23

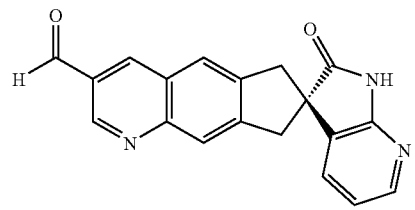

(7S)-2'-Oxo-1',2',6,8-tetrahydrospiro[cyclopenta[g]quinoline-7,3'-pyrrolo[2,3-b]pyridine]-3-carbaldehyde Essentially following the procedures described for Intermediate 22, but using (S)-5-amino-1,3-dihydrospiro[indene-2,3'-pyrrolo[2,3-b]pyridin]-2'(1'H)-one (described in Intermediate 3) in place of (±)-5-amino-1,3-dihydrospiro[indene-2,3-]pyridin]-2'(1'H)-one, the title compound was obtained. MS: m/z=316 (M+1).

Example 1

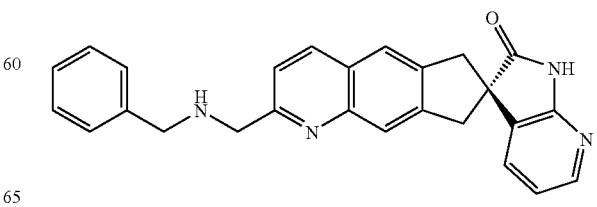

(7S)-2-[(Benzylaminomethyl)methyl]-6,8-dihydrospiro[cyclopenta[g]quinoline-7,3'-pyrrolo[2,3-b]pyridin]-2'(1'H)-one To a stirred solution of (S)-2-oxo-1',2',6,8-tetrahydrospiro[cyclopenta[g]quinoline-7,3'-pyrrolo[2,3-b]pyridine]-2-carbaldehyde (20 mg, 0.063 mmol, described in Intermediate 10), benzylamine (10 mg, 0.095 mmol), and AcOH (0.018 mL, 0.315 mmol) in 1,2-dichloroethane (1 mL) was added sodium triacetoxyborohydride (20 mg, 0.095 mmol). After 3 h, the mixture was concentrated to dryness in vacuo and the residue was purified by HPLC using a reversed phase C18 column and eluting with a gradient of $H_2O:CH_3CN:CF_3CO_2H$-90:10:0.1 to 5:95:0.1. The pure, product-containing fractions were combined and concentrated to give the title compound as the trifluoroacetate salt. MS: m/z=407 (M+1). HRMS: m/z=407.1875; calculated m/z=407.1867 for $C_{26}H_{23}N_4O$.

Example 2

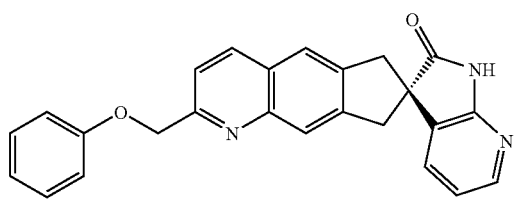

(7S)-2-(Phenoxymethyl)-6,8-dihydrospiro[cyclopenta[g]quinoline-7,3'-pyrrolo[2,3-b]pyridin]-2'(1'H)-one To a solution of phenol (11 mg, 0.12 mmol) in DMF (0.3 mL), at ambient temperature, was added potassium carbonate (21 mg, 0.15 mmol). The resulting mixture was stirred for 30 min, then (S)-2-(chloromethyl)-6,8-dihydrospiro[cyclopenta[g]quinoline-7,3'-pyrrolo[2,3-b]pyridin]-2'(1'H)-one (20 mg, 0.060 mmol, described in Intermediate 11) was added and the resulting mixture was stirred at ambient temperature for 18 h. The reaction mixture was purified directly by HPLC using a reversed phase C18 column and eluting with a gradient of $H_2O:CH_3CN:CF_3CO_2H$-90:10:0.1 to 5:95:0.1. The pure, product-containing fractions were combined and concentrated to give the title compound as the trifluoroacetate salt. MS: m/z=394 (M+1). HRMS: m/z=394.1549; calculated m/z=394.1550 for $C_{25}H_{20}N_3O_2$.

Example 3

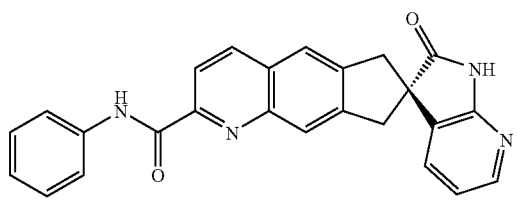

(7S)-2'-Oxo-N-phenyl-1',2',6,8-tetrahydrospiro[cyclopenta[g]quinoline-7,3'-pyrrolo[2,3-b]pyridine]-2-carboxamide A mixture of (S)-2'-oxo-1',2',6,8-tetrahydrospiro[cyclopenta[g]quinoline-7,3'-pyrrolo[2,3-b]pyridine]-2-carboxylic acid (15 mg, 0.045 mmol, described in Intermediate 14), aniline (4 mg, 0.045 mmol), EDC (26 mg, 0.136 mmol), HOBT (21 mg, 0.136 mmol), and N,N-diisopropylethylamine (0.039 mL, 0.226 mmol) was stirred in DMF (1 mL) at ambient temperature for 18 h. The reaction mixture was purified directly by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound. MS: m/z=407 (M+1). MS: m/z=407.1500; calculated m/z=407.1503 for $C_{25}H_{19}N_4O_2$.

Example 4

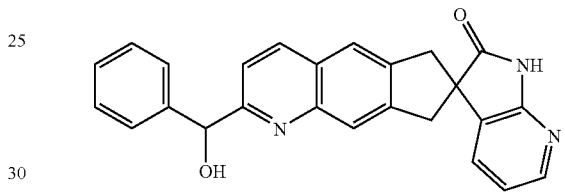

(±)-2-[Hydroxy(phenyl)methyl]-6,8-dihydrospiro[cyclopenta[g]quinoline-7,3'-pyrrolo[2,3-b]pyridin]-2'(1'H)-one, diastereomers A & B To a stirred solution of (±)-2'-oxo-1',2',6,8-tetrahydrospiro[cyclopenta[g]quinoline-7,3'-pyrrolo[2,3-b]pyridine]-2-carbaldehyde (15 mg, 0.048 mmol, described in Intermediate 18) in $CH_2Cl_2$ (0.5 mL) at −78° C. was added phenylmagnesium bromide (1.0 M in THF, 0.33 mL, 0.33 mmol) dropwise. The reaction mixture was stirred at −78° C. for 2 h and was then allowed to warm to ambient temperature. The reaction was quenched with $H_2O$ and concentrated under reduced pressure. The residue was purified by HPLC using a reversed phase C18 column and eluting with a gradient of $H_2O:CH_3CN:CF_3CO_2H$—90:10:0.1 to 5:95:0.1. The pure, product-containing fractions were combined and concentrated to give the title compound as the trifluoroacetate salt. MS: m/z=394 (M+1). HRMS: m/z=394.1565; calculated m/z=394.1550 for $C_{25}H_{20}N_3O_2$.

Example 5

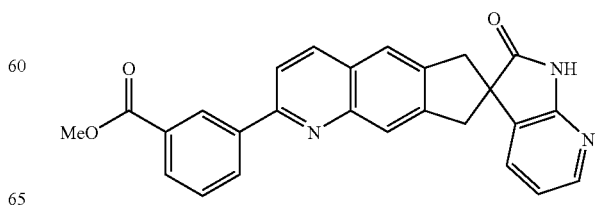

(±)-Methyl 3-(2'-oxo-1',2',6,8-tetrahydrospiro[cyclopenta[g]quinoline-7,3'-pyrrolo[2,3-b]pyridin]-2-yl)benzoate A stirred mixture of (±)-2-chloro-6,8-dihydrospiro[cyclopenta[g]quinoline-7,3'-pyrrolo[2,3-b]pyridin]-2'(1'H)-one (204 mg, 0.634 mmol, described in Intermediate 20), 3-methoxycarbonylphenylboronic acid (229 mg, 1.27 mmol), PdCl$_2$(PPh$_3$)$_2$ (44 mg, 0.063 mmol), and potassium carbonate (290 mg, 2.10 mmol), in 1,2-dimethoxyethane (3 mL) and H$_2$O (1 mL) was heated at 80° C. for 18 h. The cooled mixture was partitioned between H$_2$O (40 mL) and EtOAc (40 mL). The organic layer was removed and the aqueous phase was extracted further with EtOAc (40 mL). The combined organic extracts were washed with brine, dried over Na$_2$SO$_4$, filtered, and concentrated under reduced pressure. The residue was purified by HPLC using a reversed phase C18 column and eluting with a gradient of H$_2$O:CH$_3$CN:CF$_3$CO$_2$H—90:10:0.1 to 5:95:0.1. The product-containing fractions were combined and concentrated to give the title compound. MS: m/z=422 (M+1). HRMS: m/z=422.1504; calculated m/z=422.1499 for C$_{26}$H$_{20}$N$_3$O$_3$.

Example 6

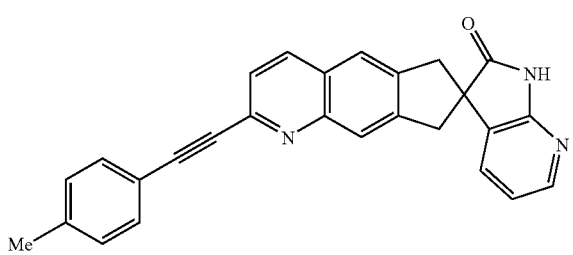

(±)-2-[(4-Methylphenyl)ethynyl]-6,8-dihydrospiro[cyclopenta[g]quinoline-7,3'-pyrrolo[2,3-b]pyridin]-2'(1'H)-one A stirred mixture of (±)-2-chloro-6,8-dihydrospiro[cyclopenta[g]quinoline-7,3'-pyrrolo[2,3-b]pyridin]-2'(1'H)-one (15 mg, 0.047 mmol, described in Intermediate 20), 4-ethynyltoluene (7 mg, 0.061 mmol), PdCl$_2$(PPh$_3$)$_2$ (4 mg, 0.006 mmol), and diethylamine (0.073 mL, 0.70 mmol) in DMF (0.5 mL) was heated at 120° C. in a microwave reactor for 5 min. The cooled mixture was partitioned between saturated aqueous NaHCO$_3$ (3 mL) and EtOAc (5 mL). The organic layer was dried over Na$_2$SO$_4$, filtered, and concentrated under reduced pressure. The residue was purified by HPLC using a reversed phase C18 column and eluting with a gradient of H$_2$O:CH$_3$CN:CF$_3$CO$_2$H—90:10:0.1 to 5:95:0.1. The product-containing fractions were combined and concentrated to give a crude product. This was further purified by silica gel chromatography, eluting with a gradient of CH$_2$Cl$_2$:MeOH—100:0 to 90:10, to give the title compound. MS: m/z=402 (M+1). HRMS: m/z=402.1609; calculated m/z=402.1601 for C$_{27}$H$_{20}$N$_3$O.

Example 7

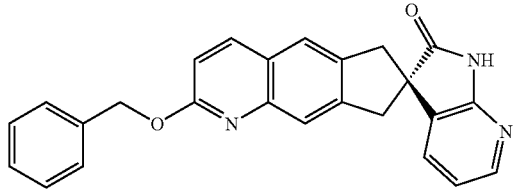

(7S-2-Benzyloxy-6 8-dihydrospiro[cyclopenta[g]quinoline-7,3'-pyrrolo[2,3-b]pyridin]-2'(1')-one To a solution of benzyl alcohol (25 mg, 0.23 mmol) in DMF (1.8 mL), at ambient temperature, was added sodium hydride (60% dispersion in mineral oil; 9 mg, 0.23 mmol). The resulting mixture was stirred for 10 min, then (7S)-2-chloro-6,8-dihydrospiro[cyclopenta[g]quinoline-7,3'-pyrrolo[2,3-b]pyridin]-2'(1'H)-one (30 mg, 0.093 mmol, described in Intermediate 21) was added and the resulting mixture was stirred at ambient temperature for 1 h at ambient temperature, then at 65° C. for 1 h. The reaction mixture was cooled, filtered, and purified by HPLC using a reversed phase C18 column and eluting with a gradient of H$_2$O:CH$_3$CN:CF$_3$CO$_2$H—90:10:0.1 to 5:95:0.1. The pure, product-containing fractions were combined and concentrated to give the title compound. MS: m/z=394 (M+1). HRMS: m/z=394.1511; calculated m/z=394.1550 for C$_{25}$H$_{20}$N$_3$O$_2$.

Example 8

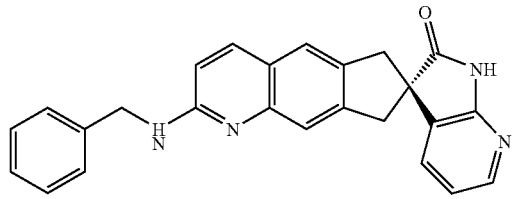

(7S)-2-Benzylamino-6,8-dihydrospiro[cyclopenta[g]quinoline-7,3'-pyrrolo[2,3-b]pyridin]-2'(1'H)-one A mixture of benzylamine (133 mg, 1.24 mmol), potassium carbonate (172 mg, 1.24 mmol), and (7S)-2-chloro-6,8-dihydrospiro[cyclopenta[g]quinoline-7,3'-pyrrolo[2,3-b]pyridin]-2'(1'H)-one (200 mg, 0.62 mmol, described in Intermediate 21) in 1-methyl-2-pyrrolidinone (2 mL) was heated at 220° C. in a microwave reactor for 30 min. The cooled reaction mixture was poured into H$_2$O (20 mL) and extracted with EtOAc (2×30 mL). The combined organic layers were dried over MgSO$_4$, filtered, and concentrated under reduced pressure. The residue was purified by HPLC using a reversed phase C18 column and eluting with a gradient of H$_2$O:CH$_3$CN:CF$_3$CO$_2$H-90:10:0.1 to 5:95:0.1. The pure, product-containing fractions were combined and concentrated to give the title compound as the trifluoroacetate salt. MS: m/z=393 (M+1). HRMS: m/z=393.1715; calculated m/z=393.1710 for $C_{25}H_{21}N_4O$.

Example 9

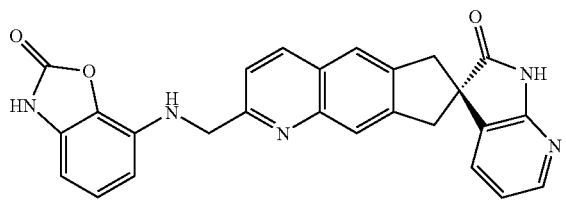

(7S)-2-{[(2-Oxo-2,3-dihydro-1,3-benzoxazol-7-yl)amino]methyl}-6,8-dihydrospiro[cyclopenta[g]quinoline-7,3'-pyrrolo[2,3-b]pyridin]-2'(1'H)-one Step A. 5-Chloro-7-nitro-1,3-benzoxazol-2(3H)-one To a stirred solution of 2-amino-4-chloro-6-nitrophenol (2.00 g, 10.6 mmol) in THF (50 mL) was added 1,1'-carbonyldiimidazole (2.06 g, 12.7 mmol) and the resulting mixture was stirred at ambient temperature for 1 h. The mixture was poured into 1 N hydrochloric acid and the precipitate was isolated by filtration, washed with $H_2O$, then hexanes, and dried in vacuo to give the title compound.

Step B. 7-Amino-1,3-benzoxazol-2(3H)-one

To a solution of 5-chloro-7-nitro-1,3-benzoxazol-2(3H)-one from Step A (1.10 g, 5.13 mmol) in EtOH (50 mL) was added 10% Pd/C (300 mg). The reaction mixture was shaken in a Parr apparatus under a hydrogen atmosphere (40 p.s.i.) for 18 h, then filtered through a Celite pad, washing with EtOH, and the filtrate was concentrated under reduced pressure to give the title compound. MS: m/z=151 (M+1).

Step C. (7S)-2-{[(2-Oxo-2,3-dihydro-1,3-benzoxazol-7-yl)amino]methyl}-6,8-dihydrospiro[cyclopenta[g]quinoline-7,3'-pyrrolo[2,3-b]pyridin]-2'(1'H)-one Essentially following the procedures described for example 1, but using 7-amino-1,3-benzoxazol-2(3B)-one from Step B in place of benzylamine, the title compound was obtained. MS: m/z=450 (M+1). HRMS: m/z=450.1563; calculated m/z=450.1561 for $C_{26}H_{20}N_5O_3$.

Example 10

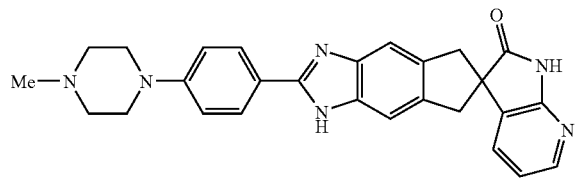

2-[4-(4-methylpiperazin-1-yl)phenyl]-5,7-dihydro-1H-spiro[indeno[5,6-d]imidazole-6,3'-pyrrolo[2,3-b]pyridin]-2'(1')-one A mixture of 5,6-diamino-1,3-dihydrospiro[indene-2,3'-pyrrolo[2,3-b]pyridin]-2'(1'H)-one (30 mg, 0.11 mmol, described in Intermediate 13), 4-(4-methylpiperazin-1-yl)benzoic acid [Mitskyavichyus & Sapiyanskaite, *Chem. Heterocycl. Compd.*, 1985, 21, 1251-1254] (21 mg, 0.10 mmol), BOP (50 mg, 0.11 mmol), and N,N-diisopropylethylamine (0.019 mL, 0.11 mmol) was stirred in, DMF (0.4 mL) at ambient temperature for 1 h, then AcOH (0.4 mL) was added and the resulting mixture was heated to 60° C. for 6 h. The reaction mixture was purified directly by HPLC using a reversed phase C18 column and eluting with a gradient of $H_2O:CH_3CN:CF_3CO_2H$-90:10:0.1 to 5:95:0.1. The pure, product-containing fractions were combined and concentrated to give the title compound as the trifluoroacetate salt. MS: m/z=451 (M+1). HRMS: m/z=451.2247; calculated m/z=451.2241 for $C_{27}H_{27}N_6O$.

Examples 11-17

Essentially following the procedures outlined for example 1 the compounds listed in Table 1 were prepared. The requisite amines were commercially available, described in the literature, synthesized according to methodology described herein (vide supra), or readily synthesized by one skilled in the art of organic synthesis. In some cases, straightforward protecting group strategies were applied. Relevant literature references are provided in the table.

TABLE 1

| Example | $R^b$ | MS (M + 1) | Literature Reference |
|---|---|---|---|
| 11 | | 449 | Mewshaw et al., Bioorg. Med. Chem. Lett., 1998, 8, 2675-2680. |
| 12 | | 462 | Tamura et al., Chem. Ind. (London), 1975, 922-923. |

TABLE 1-continued

| Example | R^b | MS (M + 1) | Literature Reference |
|---|---|---|---|
| 13 | (5-chloro-benzoxazol-2(3H)-one-7-yl-NH) | 484 | |
| 14 | (phthalimide-4-yl-NH) | 462 | |
| 15 | (benzoxazol-2(3H)-one-7-yl-NH) | 450 | Zinner & Wigert, Chem. Ber., 1960, 93, 1331-1339. |

TABLE 1-continued

| Example | R^b | MS (M + 1) | Literature Reference |
|---|---|---|---|
| 16 | (3-methyl-2-oxo-indolin-3-yl-NH) | 462 | Becker, J. Am. Chem. Soc., 1955, 77, 6608-6610. |
| 17 | (phenyl-NH) | 393 | |

Examples 18-26

Essentially following the procedures outlined for example 1, but using (±)-2'-oxo-1',2',6,8-tetrahydrospiro[cyclopenta[g]quinoline-7,3'-pyrrolo[2,3-b]pyridine]-2-carbaldehyde in place of (S)-2'-oxo-1',2',6,8-tetrahydrospiro[cyclopenta[g]quinoline-7,3'-pyrrolo[2,3-b]pyridine]-2-carbaldehyde, the compounds listed in Table 2 were prepared. The requisite amines were commercially available, described in the literature, synthesized according to methodology described herein (vide supra), or readily synthesized by one skilled in the art of organic synthesis. In some cases, straightforward protecting group strategies were applied. Relevant literature references are provided in the table.

TABLE 2

| Example | R^b | MS (M + 1) | Literature Reference |
|---|---|---|---|
| 18 | (2,2-difluoro-1-phenylethyl-NH) | 457 | |

TABLE 2-continued

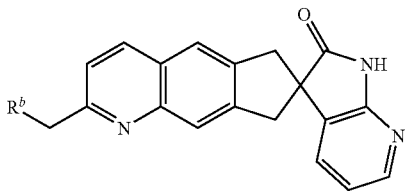

| Example | R$^b$ | MS (M + 1) | Literature Reference |
|---|---|---|---|
| 19 | (2-aminomethyl-quinazolin-4(3H)-one) | 475 | PCT Int. Appl. WO 2002048117 (2002) |
| 20 | (4-hydroxyphenethylamine) | 437 | |
| 21 | (3-hydroxybenzylamine) | 423 | |
| 22 | (7-amino-1H-indazole) | 433 | |
| 23 | (5-amino-1H-indazole) | 433 | |
| 24 | (4-amino-1H-indazole) | 433 | |
| 25 | (tryptamine) | 460 | |
| 26 | (4-aminomethyl-N-Boc-piperidine) | 514 | |

Examples 27-37

Essentially following the procedures outlined for example 3, but using (±)-2'-oxo-1',2,6,8-tetrahydrospiro[cyclopenta[g]quinoline-7,3'-pyrrolo[2,3-b]pyridine]-2-carboxylic acid in place of (S)-2'-oxo-1,2',6,8-tetrahydrospiro[cyclopenta[g]quinoline-7,3'-pyrrolo[2,3-b]pyridine]-2-carboxylic acid, the compounds listed in Table 3 were prepared. The requisite amines were commercially available, described in the literature, synthesized according to methodology described herein (vide supra), or readily synthesized by one skilled in the art of organic synthesis. In some cases, straightforward protecting group strategies were applied.

TABLE 3

| Example | R^b | MS (M + 1) |
|---|---|---|
| 27 | trans-2-phenylcyclopropylamine | 447 |
| 28 | 4-phenylcyclohexylamine | 489 |
| 29 | 3-phenylpropylamine | 449 |
| 30 | 2-phenylethylamine | 435 |
| 31 | indan-1-ylamine | 447 |
| 32 | (4-benzylmorpholin-2-yl)methylamine | 520 |
| 33 | (4-hydroxyphthalazin-1-yl)methylamine | 489 |
| 34 | 2-aminocyclohexanecarboxamide | 456 |

TABLE 3-continued

| Example | R^b | MS (M + 1) |
|---|---|---|
| 35 | 2-hydroxy-1-phenylethylamine | 451 |
| 36 | 4-amino-3,4-dihydroquinolin-2(1H)-one | 476 |
| 37 | 1-benzylpiperidin-4-ylamine | 504 |

Examples 38-41

Essentially following the procedures outlined for example 4, the compounds listed in Table 4 were prepared. The requisite Grignard reagents were commercially available, described in the literature, synthesized according to methodology described herein (vide supra), or readily synthesized by one skilled in the art of organic synthesis. In some cases, straightforward protecting group strategies were applied.

TABLE 4

| Example | R^c | MS (M + 1) |
|---|---|---|
| 38 | benzyl (CHMe) | 408 |
| 39 | cyclopentyl (CHMe) | 386 |

TABLE 4-continued

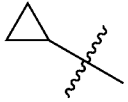

| Example | R$^c$ | MS (M + 1) |
|---|---|---|
| 40 | 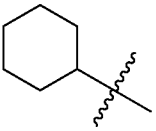 | 358 |
| 41 | 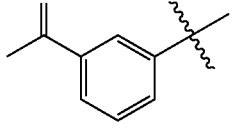 | 400 |

Examples 42-48

Essentially following the procedures outlined for example 5, the compounds listed in Table 5 were prepared. The requisite boronic acids were commercially available, described in the literature, synthesized according to methodology described herein (vide supra), or readily synthesized by one skilled in the art of organic synthesis. In some cases, straightforward protecting group strategies were applied.

TABLE 5

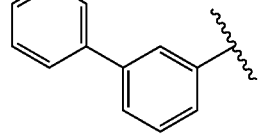

| Example | R$^a$ | MS (M + 1) |
|---|---|---|
| 42 | 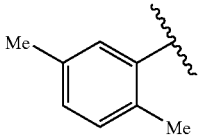 | 406 |
| 43 | 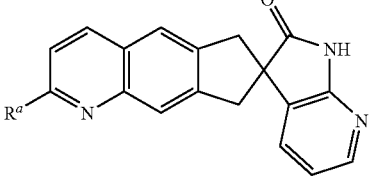 | 440 |
| 44 | 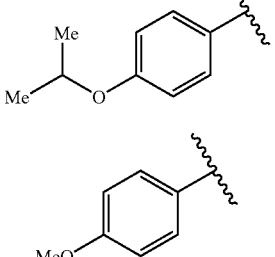 | 392 |

TABLE 5-continued

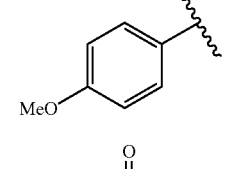

| Example | R$^a$ | MS (M + 1) |
|---|---|---|
| 45 | 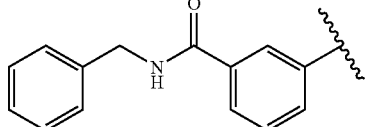 | 422 |
| 46 | 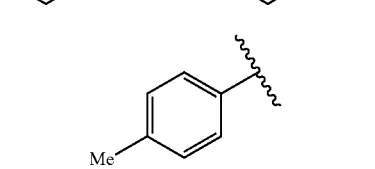 | 394 |
| 47 | 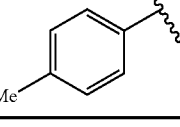 | 497 |
| 48 | 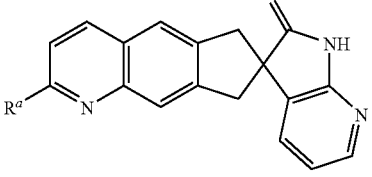 | 378 |

Examples 49-52

Essentially following the procedures outlined for example 6, the compounds listed in Table 6 were prepared. The requisite alkynes were commercially available, described in the literature, synthesized according to methodology described herein (vide supra), or readily synthesized by one skilled in the art of organic synthesis. In some cases, straightforward protecting group strategies were applied.

TABLE 6

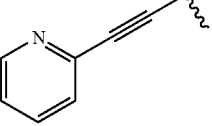

| Example | R$^a$ | MS (M + 1) |
|---|---|---|
| 49 | 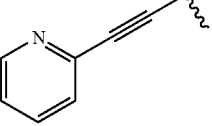 | 389 |

TABLE 6-continued

| Example | R$^a$ | MS (M + 1) |
|---------|-------|------------|
| 50 | 4-pyridyl-C≡C- | 389 |
| 51 | PhO-CH$_2$-C≡C- | 418 |
| 52 | 1-amino-cyclohexyl-C≡C- | 409 |

Examples 53-78

Essentially following the procedures outlined for example 10, the compounds listed in Table 7 were prepared. The requisite acids were commercially available, described in the literature, synthesized according to methodology described herein (vide supra), or readily synthesized by one skilled in the art of organic synthesis. In some cases, straightforward protecting group strategies were applied.

TABLE 7

| Example | R$^d$ | MS (M + 1) |
|---------|-------|------------|
| 53 | 4-HO-C$_6$H$_4$-CH$_2$- | 369 |
| 54 | PhCH$_2$- | 367 |
| 55 | 1-naphthyl-CH$_2$- | 417 |
| 56 | 3-PhO-C$_6$H$_4$-CH$_2$- | 459 |
| 57 | trans-3-benzoyl-cyclopentyl- | 449 |
| 58 | 2'-F-biphenyl-3-yl-CH$_2$- | 447 |
| 59 | (E)-PhCH=CH-CH$_2$- | 379 |
| 60 | 1-benzyl-5-methyl-pyrazol-3-yl- | 447 |
| 61 | N-Boc-spiro-isoxazoline-pyrrolidinyl- | 501 |

TABLE 7-continued
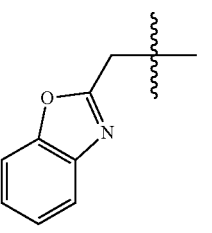
| Example | R<sup>d</sup> | MS (M + 1) |
|---|---|---|
| 62 | 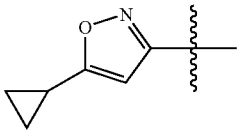 | 408 |
| 63 | 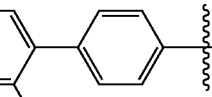 | 384 |
| 64 | 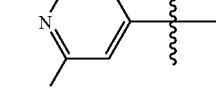 | 558 |
| 65 | 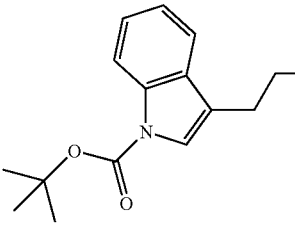 | 422 |
| 66 | 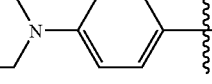 | 520 |
| 67 | 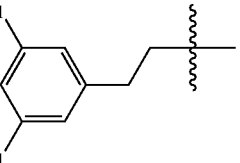 | 436 |
TABLE 7-continued
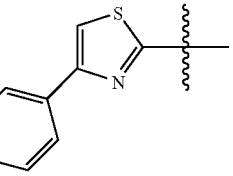
| Example | R<sup>d</sup> | MS (M + 1) |
|---|---|---|
| 68 | 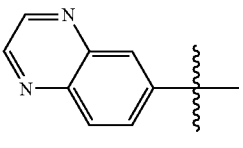 | 449 |
| 69 | 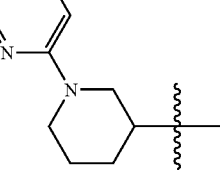 | 436 |
| 70 | 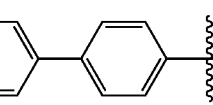 | 405 |
| 71 | 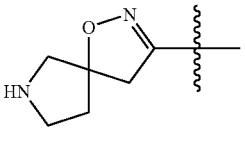 | 437 |
| 72 | 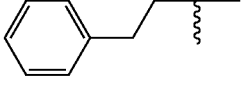 | 429 |
| 73 | 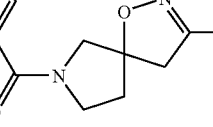 | 401 |
| 74 | | 406 |
| 75 | | 505 |

TABLE 7-continued

| Example | R^d | MS (M + 1) |
|---|---|---|
| 76 | | 450 |
| 77 | | 436 |
| 78 | | 393 |

Example 79

(±)-N-(3,5-Difluorobenzyl)-2,2-dimethyl-N-[(2'-oxo-1',2',6,8-tetrahydrospiro[cyclopenta[g]quinoline-7,3'-pyrrolo[2,3-b]pyridin]-3-yl)methyl]propanamide Step A. (±)-3-{[(3,5-Difluorobenzyl)amino]methyl}-6,8-dihydrospiro[cyclopenta[g]quinoline-7,3'-pyrrolo[2,3-b]pyridin]-2'(1'H)-one To a stirred suspension of (±)-2'-oxo-1',2',6,8-tetrahydrospiro[cyclopenta[g]quinoline-7,3'-pyrrolo[2,3-b]pyridine]-3-carbaldehyde (70.9 mg, 0.225 mmol, described in Intermediate 22) and 3,5-difluorobenzyl amine (48.3 mg, 0.340 mmol) in chloroform (2.3 mL) was added sodium triacetoxyborohydride (76.3 mg, 0.36 mmol). After 22 hours (50% conversion as judged by LCMS), the reaction mixture was diluted with chloroform (50 mL) and saturated sodium bicarbonate (20 mL). The aqueous layer was extracted twice with chloroform (50 mL×2). The combined organics were dried over sodium sulfate. Filtration to remove drying agent gave a solution which was concentrated in vacuo to give a yellow residue. The impure product was purified by silica gel chromatography, eluting with a gradient of $CH_2Cl_2$:MeOH- 100:1 to 90:10, to give individually starting aldehyde and the title compound. MS: m/z=443 (M+1).

Step B. (±)-N-(3,5-Difluorobenzyl)-2,2-dimethyl-N-[(2'-oxo-1',2',6,8-tetrahydrospiro[cyclopenta[g]quinoline-7,3'-pyrrolo[2,3-b]pyridin]-3-yl)methyl]propanamide To a suspension of (±)-3-{[(3,5-difluorobenzyl)amino]methyl}-6,8-dihydrospiro[cyclopenta[g]quinoline-7,3'-pyrrolo[2,3-b]pyridin]-2'(1'H)-one from Step A (47.0 mg, 0.106 mmol) in DCM (1.5 mL) was added 4-methylmorpholine (32.2 mg, 0.320 mmol). This mixture was sonicated to provided a finely powdered suspension. After cooling to 0° C., trimethylacetyl chloride (23.0 mg, 0.190 mmol) was added and the cooling bath was removed. After 23 hours, additional 4methylmorpholine (2 drops) and trimethylacetyl chloride (23.0 mg, 0.190 mmol) were added. After 7 hours, the reaction was quenched by the addition of one drop of methanol. This reaction mixture was applied to a silica gel column for purification, eluting with a gradient of $CH_2Cl_2$:MeOH— 100:1 to 94:6, to give the title compound as a white solid. MS: m/z=527 (M+1). HRMS: m/z=527.2253; calculated m/z=527.2253 for $C_{31}H_{29}F_2N_4O_2$.

Examples 80-87

Essentially following the procedures outlined for example 79, but using Intermediate 23 in place of Intermediate 22, the compounds listed in Table 8 were prepared. The requisite amines and carboxylic acid derivatives were commercially available, described in the literature, synthesized according to methodology described herein (vide supra), or readily synthesized by one skilled in the art of organic synthesis.

TABLE 8

| Example | R^b | MS (M + 1) |
|---|---|---|
| 80 | 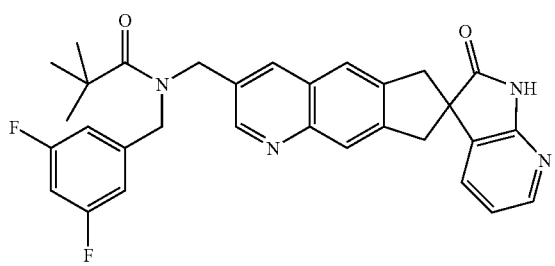 | 505 |

TABLE 8-continued

| Example | R^b | MS (M + 1) |
|---------|-----|------------|
| 81 | | 541 |
| 82 | | 593 |
| 83 | | 579 |
| 84 | | 523 |
| 85 | | 519 |
| 86 | | 535 |
| 87 | | 477 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

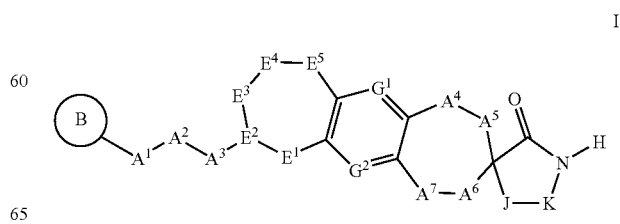

wherein:

B is a selected from:

$C_{3-10}$cycloalkyl, phenyl, naphthyl, tetrahydronaphthyl, indanyl, biphenyl, phenanthryl, anthryl, azepanyl, azepinyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indazolyl, indolinyl, indolyl, isochromanyl, isoindolinyl, isoquinolinyl, isoxazolyl, isoxazolinyl, isoxazolidinyl, isothiazolidinyl, isothiazolyl, morpholinyl, naphthyridinyl, oxadiazolyl, oxazolyl, oxazolinyl, oxazolidinyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, phthalazinyl, piperidyl, piperazinyl, pyrazinyl, pyrazolidinyl, pyrazolyl, pyridazinyl, pyridinyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, thienyl, triazolyl and triazolinyl, where B is linked to $A^1$ via a carbon atom in B and where B is unsubstituted or substituted with 1-5 substituents independently selected from $R^1$, $R^2$, $R^{3a}$ and $R^{3b}$, wherein $R^1$, $R^2$, $R^{3a}$ and $R^{3b}$ are each independently selected from:

(1) —$C_{1-6}$alkyl, which is unsubstituted or substituted with 1-7 substituents each independently selected from:

(a) halo, (b) hydroxy, (c) —O—$C_{1-6}$alkyl, which is unsubstituted or substituted with 1-5 halo, (d) —$C_{3-6}$cycloalkyl, (e) phenyl or heterocycle, wherein heterocycle is selected from: azetidinyl, imidazolyl, oxazolyl, pyridinyl, pyrimidinyl, pyrazinyl, pyridazinyl, piperidinyl, azepanyl, azepinyl, piperazinyl, pyrazolyl, pyrrolidinyl, thiazolyl, thienyl, triazolyl, tetrazolyl, tetrahydrofuryl and morpholinyl, which phenyl or heterocycle is unsubstituted or substituted with 1-5 substituents each independently selected from:

(i) —$C_{1-6}$alkyl, which is unsubstituted or substituted with 1-5 halo, (ii) —O—$C_{1-6}$alkyl, which is unsubstituted or substituted with 1-5 halo, (iii) halo, (iv) hydroxy, (v) trifluoromethyl, (vi) —$OCF_3$, (vii) oxo, (viii) amino, (ix) phenyl, and (x) benzyl, (f) —$CO_2R^9$, wherein $R^9$ is independently selected from:

(i) hydrogen, (ii) —$C_{1-6}$alkyl, which is unsubstituted or substituted with 1-6 substituents, substituents each independently selected from:

(I) halo, (II) hydroxy, (III) —O—$C_{1-6}$alkyl, which is unsubstituted or substituted with 1-5 halo, (IV) —$C_{3-6}$cycloalkyl, (V) phenyl, which is unsubstituted or substituted with 1-5 substituents each independently selected from:

(1) —$C_{1-4}$alkyl, (2) —O—$C_{1-6}$alkyl, (3) halo, (4) trifluoromethyl, and (5) —$OCF_3$, (iii) —$C_{3-6}$cycloalkyl, which is unsubstituted or substituted with 1-6 substituents, substituents each independently selected from:

(I) halo, (II) hydroxy, (III) —O—$C_{1-6}$alkyl, which is unsubstituted or substituted with 1-5 halo, (IV) —$C_{1-6}$alkyl, which is unsubstituted or substituted with 1-5 halo, and (V) phenyl, and (iv) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:

(I) halo, (II) —$C_{1-6}$alkyl, which is unsubstituted or substituted with 1-5 halo (III) —O—$C_{1-6}$alkyl, which is unsubstituted or substituted with 1-5 halo (IV) —$C_{3-6}$cycloalkyl, (V) oxo, (VI) —CN, (VII) hydroxy, and (VIII) phenyl, (g) —$NR^{10}R^{11}$, wherein $R^{10}$ and $R^{11}$ are each independently selected from:

(i) hydrogen, (ii) —$C_{1-6}$alkyl, which is unsubstituted or substituted with 1-6 substituents each independently selected from:

(I) —O—$C_{1-6}$alkyl, which is unsubstituted or substituted with 1-5 halo, (II) halo, (III) hydroxy, (IV) —$OCF_3$, (V) —$C_{3-6}$cycloalkyl, and (VI) phenyl, (iii) —C$_{4-6}$cycloalkyl,
(iv) phenyl, which is unsubstituted or substituted with 1-5 substituents each independently selected from:
  (I) —C$_{1-6}$alkyl, which is unsubstituted or substituted with 1-5 halo,
  (II) —O—C$_{1-6}$alkyl, which is unsubstituted or substituted with 1-5 halo,
  (III) halo,
  (IV) hydroxy,
  (V) trifluoromethyl,
  (VI) —OCF$_3$, and
  (VII) CN, and
(v) benzyl, which is unsubstituted or substituted with 1-5 substituents each independently selected from:
  (I) —C$_{1-6}$alkyl, which is unsubstituted or substituted with 1-5 halo,
  (II) —O—C$_{1-6}$alkyl, which is unsubstituted or substituted with 1-5 halo,
  (III) halo, and
  (IV) trifluoromethyl,
(vi) —COR$^9$, and
(vii) —SO$_2$R$^{12}$,
(h) —SO$_2$R$^{12}$, wherein R$^{12}$ is selected from:
  (i) —C$_{1-6}$alkyl, which is unsubstituted or substituted with 1-6 fluoro,
  (ii) —C$_{3-6}$cycloalkyl,
  (iii) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo,
    (IV) hydroxy,
    (V) trifluoromethyl,
    (VI) —OCF$_3$, and
    (VII) CN, and
  (iv) benzyl, which is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo, and
    (IV) trifluoromethyl,
(i) —CONR$^{10a}$R$^{11a}$, wherein R$^{10a}$ and R$^{11a}$ are each independently selected from:
  (i) hydrogen,
  (ii) —C$_{1-6}$alkyl, which is unsubstituted or substituted with 1-6 substituents each independently selected from:
    (I) —O—C$_{1-6}$alkyl, which is unsubstituted or substituted with 1-5 halo,
    (II) halo,
    (III) hydroxy,
    (IV) —OCF$_3$,
    (V) —C$_{3-6}$cycloalkyl, and
    (VI) phenyl,
  (iii) —C$_{5-6}$cycloalkyl, which is unsubstituted or substituted with 1-5 halo,
  (iv) phenyl, which is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo,
    (IV) hydroxy,
    (V) trifluoromethyl,
    (VI) —OCF$_3$, and
    (VII) CN, and
  (v) benzyl, which is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo, and
    (IV) trifluoromethyl,
  or where R$^{10a}$ and R$^{11a}$ join to form a ring selected from azetidinyl, pyrrolidinyl, piperidinyl, azepanyl, piperazinyl and morpholinyl, which ring is unsubstituted or substituted with 1-5 substituents each independently selected from:
    (I) —C$_{1-6}$alkyl, which is unsubstituted or substituted with 1-5 halo,
    (II) —O—C$_{1-6}$alkyl, which is unsubstituted or substituted with 1-5 halo,
    (III) halo
    (IV) hydroxy
    (V) phenyl, which is unsubstituted or substituted with 1-5 substituents each independently selected from:
      (1) —C$_{1-4}$alkyl, which is unsubstituted or substituted with 1-3 halo,
      (2) —O—C$_{1-4}$alkyl, which is unsubstituted or substituted with 1-3 halo, and
      (3) halo,
    (VI) benzyl, which is unsubstituted or substituted with 1-5 substituents each independently selected from:
      (1) —C$_{1-4}$alkyl, which is unsubstituted or substituted with 1-3 halo,
      (2) —O—C$_{1-4}$alkyl, which is unsubstituted or substituted with 1-3 halo, and
      (3) halo,
    (VII) —COR$^9$, and
    (VIII) —SO$_2$R$^{12}$,
(j) trifluoromethyl,
(k) —OCO$_2$R$^9$,
(l) —(NR$^{10a}$)CO$_2$R$^9$,
(m) —O(CO)NR$^{10a}$R$^{11a}$,
(n) —(NR$^9$)(CO)NR$^{10a}$R$^{11a}$,
(o) —SO$_2$NR$^{10a}$R$^{11a}$, and
(p) —O—C$_{3-6}$cycloalkyl,
(2) —C$_{3-6}$cycloalkyl, which is unsubstituted or substituted with 1-7 substituents each independently selected from:
  (a) halo,
  (b) hydroxy,
  (c) —C$_{1-6}$alkyl, which is unsubstituted or substituted with 1-5 halo, (d) —O—$C_{1-6}$alkyl, which is unsubstituted or substituted with 1-5 halo,
(e) phenyl, which is unsubstituted or substituted with 1-5 substituents each independently selected from:
  (i) —$C_{1-6}$alkyl, which is unsubstituted or substituted with 1-5 halo,
  (ii) —O—$C_{1-6}$alkyl, which is unsubstituted or substituted with 1-5 halo,
  (iii) halo,
  (iv) hydroxy, and
  (v) trifluoromethyl,
(3) phenyl or heterocycle, wherein heterocycle is selected from: pyridinyl, pyrimidinyl, pyrazinyl, thienyl, pyridazinyl, pyrrolidinyl, azetidinyl, azepanyl, thiazolyl, isothiazolyl, oxazolyl, isoxazolyl, imidazolyl, triazolyl, tetrazolyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, 1,3-dioxolanyl, oxadiazolyl, piperidinyl, tetrahydropyranyl, tetrahydrothienyl, tetrahydrothiopyranyl, and morpholinyl, which phenyl or heterocycle is unsubstituted or substituted with 1-5 substituents each independently selected from:
  (a) —$C_{1-6}$alkyl, which is unsubstituted or substituted with 1-5 substituents each independently selected from:
    (i) halo,
    (ii) hydroxy,
    (iii) —O—$C_{1-6}$alkyl, which is unsubstituted or substituted with 1-5 halo,
    (iv) —$C_{3-6}$cycloalkyl,
    (v) phenyl,
    (vi) —$CO_2R^9$, and
    (vii) —$NR^{10}R^{11}$,
  (b) halo,
  (c) hydroxy,
  (d) —O—$C_{1-6}$alkyl, which is unsubstituted or substituted with 1-6 halo,
  (e) —$C_{3-6}$cycloalkyl,
  (f) phenyl or heterocycle, wherein heterocycle is selected from: pyrrolidinyl, piperidinyl, piperazinyl, pyridinyl, pyrimidinyl, pyrazinyl, thienyl and morpholinyl, which phenyl or heterocycle is unsubstituted or substituted with 1-5 substituents each independently selected from:
    (i) —$C_{1-6}$alkyl,
    (ii) —O—$C_{1-6}$alkyl,
    (iii) halo,
    (iv) hydroxy, and
    (v) trifluoromethyl,
  (g) —$CO_2R^9$,
  (h) —(CO)$R^9$,
  (i) —$NR^{10}R^{11}$,
  (j) —$CONR^{10a}R^{11a}$,
  (k) oxo
  (l) —$SR^{12}$,
  (m) —$S(O)R^{12}$,
  (n) —$SO_2R^{12}$,
  (o) —$SO_2NR^{10a}R^{11a}$, and
  (p) —CN,
(4) halo,
(5) oxo,
(6) hydroxy,
(7) —O—$C_{1-6}$alkyl, which is unsubstituted or substituted with 1-5 substituents each independently selected from:
  (a) halo,
  (b) hydroxy,
  (c) —$C_{3-6}$cycloalkyl,
  (d) phenyl,
  (e) —$CO_2R^9$, and
  (f) —$NR^{10}R^{11}$,
(8) —CN,
(9) —$CO_2R^9$,
(10) —$NR^{10}R^{11}$,
(11) —$SR^{12}$,
(12) —$S(O)R^{12}$,
(13) —$SO_2R^{12}$,
(14) —$SO_2NR^{10a}R^{11a}$,
(15) —$CONR^{10a}R^{11a}$,
(16) —$OCO_2R^9$,
(17) —$(NR^{10a})CO_2R^9$,
(18) —$O(CO)NR^{10a}R^{11a}$,
(19) —$(NR^9)(CO)NR^{10a}R^{11a}$,
(20) —(CO)—(CO)$NR^{10a}R^{11a}$, and
(21) —(CO)—(CO)$OR^9$;
or where $R^{3a}$ and $R^{3b}$ and the atom(s) to which they are attached join to form a ring selected from cyclobutyl, cyclopentyl, cyclohexyl, cyclopentenyl, cyclohexenyl, azetidinyl, pyrrolidinyl, piperidinyl, azepanyl, tetrahydrofuranyl, tetrahydropyranyl, furanyl, dihydrofuranyl, dihydropyranyl, thienyl, dihydrothienyl, tetrahydrothienyl, dihydrothiopyranyl, tetrahydrothiopyranyl, imidazolyl, imidazolinyl, and piperazinyl, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) hydroxy,
    (iii) —O—$C_{1-6}$alkyl, which is unsubstituted or substituted with 1-3 halo,
    (iv) —$C_{3-6}$cycloalkyl,
    (v) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —$C_{1-6}$alkyl,
      (II) —O—$C_{1-6}$alkyl,
      (III) halo,
      (IV) hydroxy,
      (V) trifluoromethyl, and
      (VI) —$OCF_3$,
    (vi) —$CO_2R^9$,
    (vii) —$NR^{10}R^{11}$,
    (viii) —$SO_2R^{12}$,
    (ix) —$CONR^{10a}R^{11a}$, and
    (x) —$(NR^{10a})CO_2R^9$,
  (b) phenyl or heterocycle, wherein heterocycle is selected from: pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:

(i) —C$_{1-6}$alkyl, which is unsubstituted or substituted with 1-6 fluoro,
(ii) halo,
(iii) hydroxy,
(iv) —O—C$_{1-6}$alkyl, which is unsubstituted or substituted with 1-6 fluoro, and
(v) —C$_{3-6}$cycloalkyl,
(c) halo,
(d) —SO$_2$R$^{12}$,
(e) hydroxy,
(f) —O—C$_{1-6}$alkyl, which is unsubstituted or substituted with 1-5 halo,
(g) —CN,
(h) —COR$^{12}$,
(i) —NR$^{10}$R$^{11}$,
(j) —CONR$^{10a}$R$^{11a}$,
(k) —CO$_2$R$^9$,
(l) —(NR$^{10a}$)CO$_2$R$^9$,
(m) —O(CO)NR$^{10a}$R$^{11a}$, and
(n) —(NR$^9$)(CO)NR$^{10a}$R$^{11a}$;

A$^1$, A$^2$ and A$^3$ are each independently selected from:
(1) a bond,
(2) —CR$^{13}$R$^{14}$—, wherein R$^{13}$ and R$^{14}$ are each independently selected from:
(a) hydrogen,
(b) C$_{1-6}$ alkyl, which is unsubstituted or substituted with 1-5 substituents each independently selected from:
(i) —C$_{3-6}$cycloalkyl,
(ii) —O—C$_{1-6}$alkyl,
(iii) halo,
(iv) hydroxy, and
(v) phenyl,
(c) hydroxy, and
(d) halo,
(3) —NR$^{10}$—,
(4) —CR$^{13}$R$^{14}$—NR$^{10}$—,
(5) —CR$^{13}$R$^{14}$—CH$_2$—,
(6) —CH$_2$—CR$^{13}$R$^{14}$—,
(7) —O—CR$^{13}$R$^{14}$—,
(8) —CR$^{13}$R$^{14}$—O—,
(9) —C≡C—,
(10) —C(R$^{13}$)=C(R$^{14}$)—, and
(11) —C(=O)—,
or wherein one or two of A$^1$, A$^2$ and A$^3$ are absent;
A$^5$ and A$^6$
—CR$^{13}$R$^{14}$—;
A$^4$ and A$^7$ are absent;
E$^1$ is —N(R$^4$)—, E$^2$ is

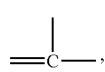

E$^3$ and E$^4$ are absent, and E$^5$ is =N— to form:

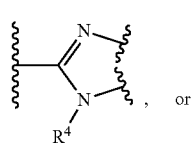

E$^1$ is =N—, E$^2$ is

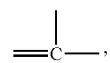

E$^3$ and E$^5$ are =C(R$^4$)— and E$^4$ is absent, form:

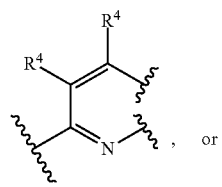

E$^5$ is =N—, E$^2$ is

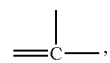

E$^1$ and E$^3$ are =C(R$^4$)— and E$^4$ is absent, form:

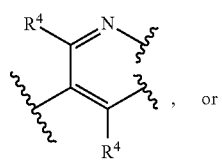

E$^1$ and E$^5$ are =N—, E$^2$ is

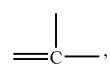

E$^3$ is =C(H)— and E$^4$ is absent, form:

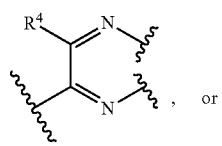

E$^1$ is —N(R$^4$)—, E$^2$ is

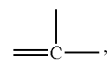

$E^3$ is =N— and $E^4$ and $E^5$ are —$CR^4R^5$— to form:

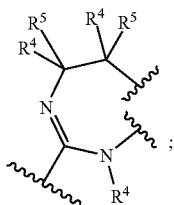

$G^1$ $G^2$ are
=C($R^4$)—
J is
=C($R^{6a}$)—
K is
=C($R^{6b}$)—;
$R^4$ and $R^5$ are each independently selected from:
(1) hydrogen,
(2) —$C_{1-4}$alkyl, which is unsubstituted or substituted with 1-5 substituents each independently selected from:
 (a) halo,
 (b) hydroxy,
 (c) —O—$C_{1-6}$alkyl,
 (d) —$C_{3-6}$cycloalkyl,
 (e) phenyl,
 (f) —$CONR^{10a}R^{11a}$,
 (g) —$CO_2R^9$, and
 (h) —$NR^{10}R^{11}$,
(3) —$C_{3-6}$cycloalkyl,
(4) phenyl, which is unsubstituted or substituted with 1-3 substituents each independently selected from:
 (a) —$C_{1-4}$alkyl, which is unsubstituted or substituted with 1-3 fluoro,
 (b) halo,
 (c) hydroxy, and
 (d) —O—$C_{1-6}$alkyl, which is unsubstituted or substituted with 1-6 fluoro,
(5) halo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,
(13) —$OCO_2R^9$, and
(14) —$(NR^{10a})CO_2R^9$;
$R^{6a}$ and $R^{6b}$ and the atom(s) to which they are attached join to form pyridinyl, fused between atoms 2 and 3 as follows:

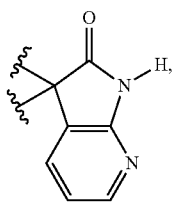

said pyridinyl unsubstituted or substituted with 1-5 substituents each independently selected from:

(a) —$C_{1-6}$alkyl, which is unsubstituted or substituted with 1-3 substituents each independently selected from:
 (i) halo,
 (ii) hydroxy,
 (iii) —O—$C_{1-6}$alkyl,
 (iv) —$C_{3-6}$cycloalkyl,
 (v) phenyl or heterocycle, wherein heterocycle is selected from: pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
  (I) —$C_{1-6}$alkyl,
  (II) —O—$C_{1-6}$alkyl,
  (III) halo,
  (IV) hydroxy,
  (V) trifluoromethyl, and
  (VI) —$OCF_3$,
 (vi) —$CO_2R^9$,
 (vii) —$NR^{10}R^{11}$,
 (viii) —$SO_2R^{12}$,
 (ix) —$CONR^{10a}R^{11a}$, and
 (x) —$(NR^{10a})CO_2R^9$,
(b) phenyl or heterocycle, wherein heterocycle is selected from: pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:
 (i) —$C_{1-6}$alkyl, which is unsubstituted or substituted with 1-6 fluoro,
 (ii) halo,
 (iii) hydroxy,
 (iv) —O—$C_{1-6}$alkyl, which is unsubstituted or substituted with 1-6 fluoro, and
 (v) —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo;
or a pharmaceutically acceptable salt thereof and individual enantiomers and diastereomers thereof.

2. The compound of claim 1 having the formula Ib:

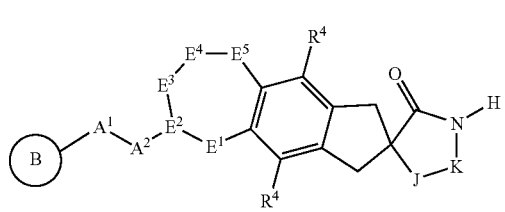

or a pharmaceutically acceptable salt thereof and individual enantiomers and diastereomers thereof.

3. The compound of claim 1, wherein B is selected from the group consisting of: $C_{3-10}$cycloalkyl, phenyl, biphenyl, naphthyl, tetrahydronaphthyl, indanyl, indolyl, indolinyl, indazolyl, isoindolinyl, isoquinolinyl, isoxazolyl, isoxazolinyl, morpholinyl, naphthyridinyl, piperidinyl, piperazinyl, pyrazinyl, pyridazinyl, pyridinyl, pyrimidinyl, pyrimidyl, pyrrolidinyl, quinazolinyl, quinolinyl, quinoxalinyl, tetrahydroquinolinyl, phthalazinyl, pyrazolyl, isoxazolinyl, indazolyl, benzoxazolyl, benzoxazolinyl, benzimidazolyl, benzimidazolinyl, thiazolyl, and thienyl, which is unsubstituted or substituted with 1-5 substituents selected from $R^1$, $R^2$, $R^{3a}$ and $R^{3b}$.

4. The compound of claim 3, wherein $R^1$, $R^2$, $R^{3a}$ and $R^{3b}$ are each independently selected from:
  (1) $C_{1-6}$ alkyl, which is unsubstituted or substituted with 1-5 substituents each independently selected from:
    (a) halo,
    (b) hydroxy,
    (c) —O—$C_{1-6}$alkyl,
    (d) —$C_{3-6}$cycloalkyl,
    (e) phenyl or heterocycle, wherein heterocycle is selected from: pyridinyl, piperidinyl, piperazinyl, pyrrolidinyl and morpholinyl,
    (f) —(NR$^{10a}$)CO$_2$R$^9$, and
    (l) NR$^{10}$R$^{11}$,
  (2) $C_{3-6}$ cycloalkyl,
  (3) —OR$^9$,
  (4) —OCF$_3$,
  (5) trifluoromethyl,
  (6) halo,
  (7) oxo,
  (8) hydroxy,
  (9) —CN,
  (10) —COR$^{12}$,
  (11) —CO$_2$R$^{12}$,
  (12) —CONR$^{10a}$R$^{11a}$,
  (13) —NR$^{10}$R$^{11}$,
  (14) phenyl, which is unsubstituted or substituted with 1-5 substituents selected from:
    (a) $C_{1-6}$alkyl,
    (b) —O—$C_{1-6}$alkyl,
    (c) halo,
    (d) —OH, and
    (e) —CF$_3$, and
  (15) heterocycle, wherein heterocycle is selected from: pyridinyl, pyrimidinyl, pyrazinyl, thienyl, pyrrolidinyl, piperazinyl, piperidinyl, tetrazolyl, or morpholinyl, and which is unsubstituted or substituted with 1-5 substituents selected from:
    (a) $C_{1-6}$alkyl,
    (b) —O—$C_{1-6}$alkyl,
    (c) halo,
    (d) —OH, and
    (e) —CF$_3$.

5. The compound of claim 1, wherein $R^{3a}$ and $R^{3b}$ and the carbon atom(s) to which they are attached join to form a ring selected from piperidinyl, cyclohexyl, cyclopentyl, pyrrolidinyl, tetrahydrofuranyl, tetrahydropyranyl, tetrahydrothienyl, and tetrahydrothiopyranyl, which ring is unsubstituted or substituted with 1-3 substituents independently selected from:
  (a) —$C_{1-6}$alkyl, which is unsubstituted or substituted with 1-3 substituents each independently selected from:
    (i) halo, and
    (ii) phenyl,
  (b) phenyl or heterocycle, wherein heterocycle is selected from: pyridinyl, pyrimidinyl and pyrazinyl,
  (c) —CO$_2$R$^9$,
  (d) hydroxy, and
  (e) oxo.

6. The compound of claim 1, wherein $R^{3a}$ and $R^{3b}$ and the carbon atom(s) to which they are attached are joined together to form a ring selected from piperidinyl, cyclohexyl, tetrahydropyranyl, and tetrahydrothiopyranyl, which ring is unsubstituted or substituted with 1-3 substituents independently selected from:
  (a) —$C_{1-6}$alkyl, which is unsubstituted or substituted with 1-3 substituents independently selected from:
    (i) fluoro, and
    (ii) phenyl,
  (b) —CO$_2$—$C_{1-4}$alkyl,
  (c) hydroxyl, and
  (d) oxo.

7. The compound of claim 1, wherein $A^1$ is selected from a bond, —CR$^{13}$R$^{14}$—, —OCH$_2$—, —C≡C—, —CH$_2$—CH$_2$—, —C(H)=C(H)—, —NH— and —C(=O)—; $A^2$ is selected from a bond, CH$_2$, —CH$_2$—NH—, —C(=O)—, —C≡C—, —NH— and —CH$_2$—CH$_2$—; and $A^3$ is selected from a bond, —CH$_2$—, —C(=O)— and —CH$_2$O—.

8. The compound of claim 1, wherein $G^1$ is =C(H)— and $G^2$ is =C(H)—.

9. A compound selected from:

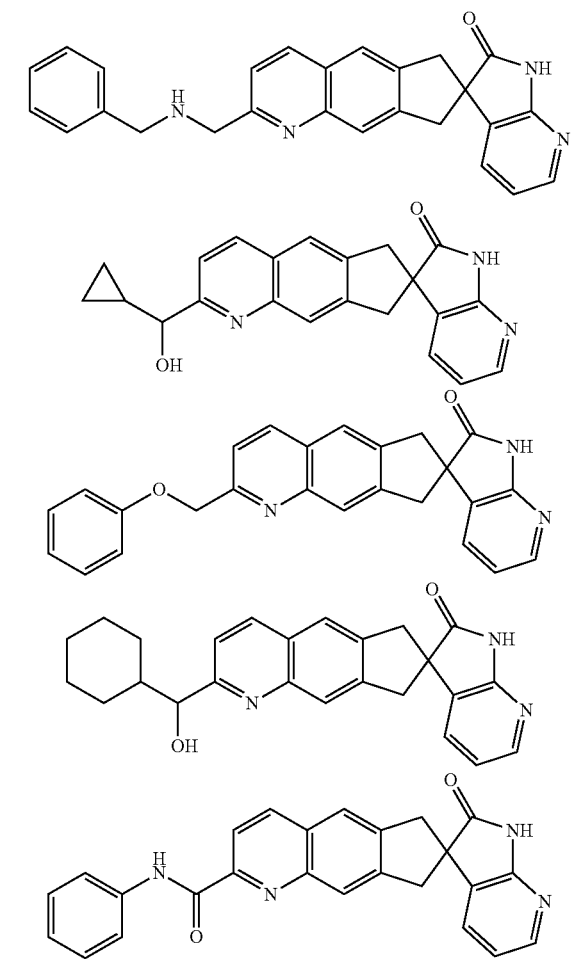

107
-continued
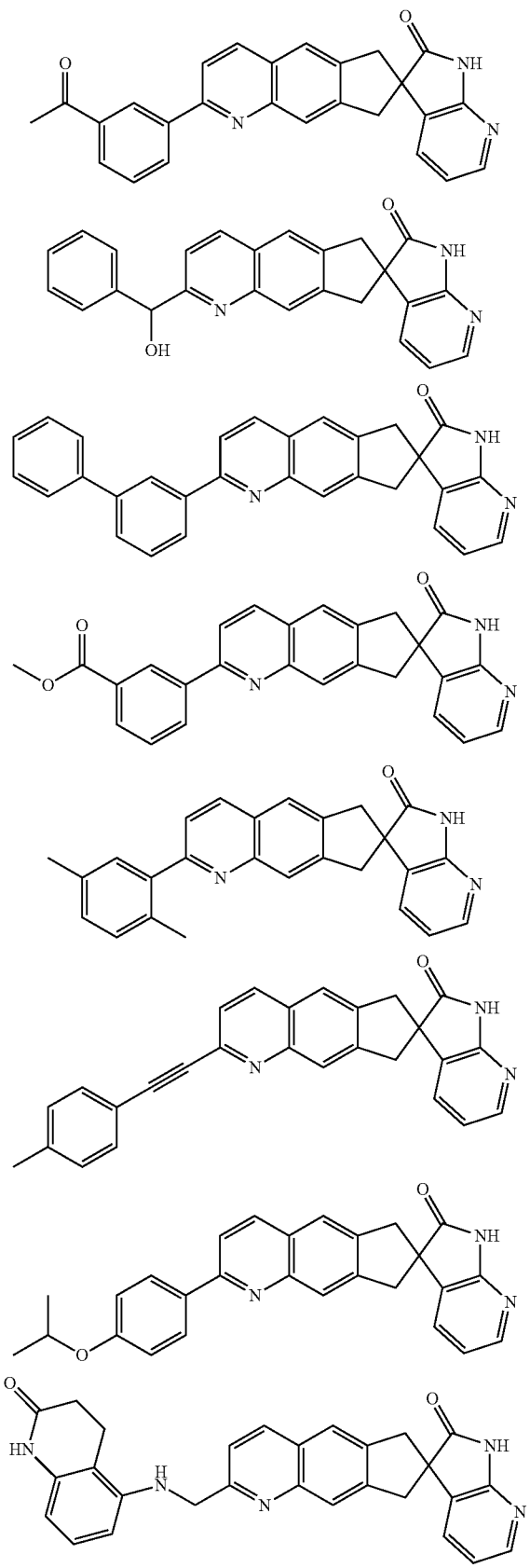
108
-continued
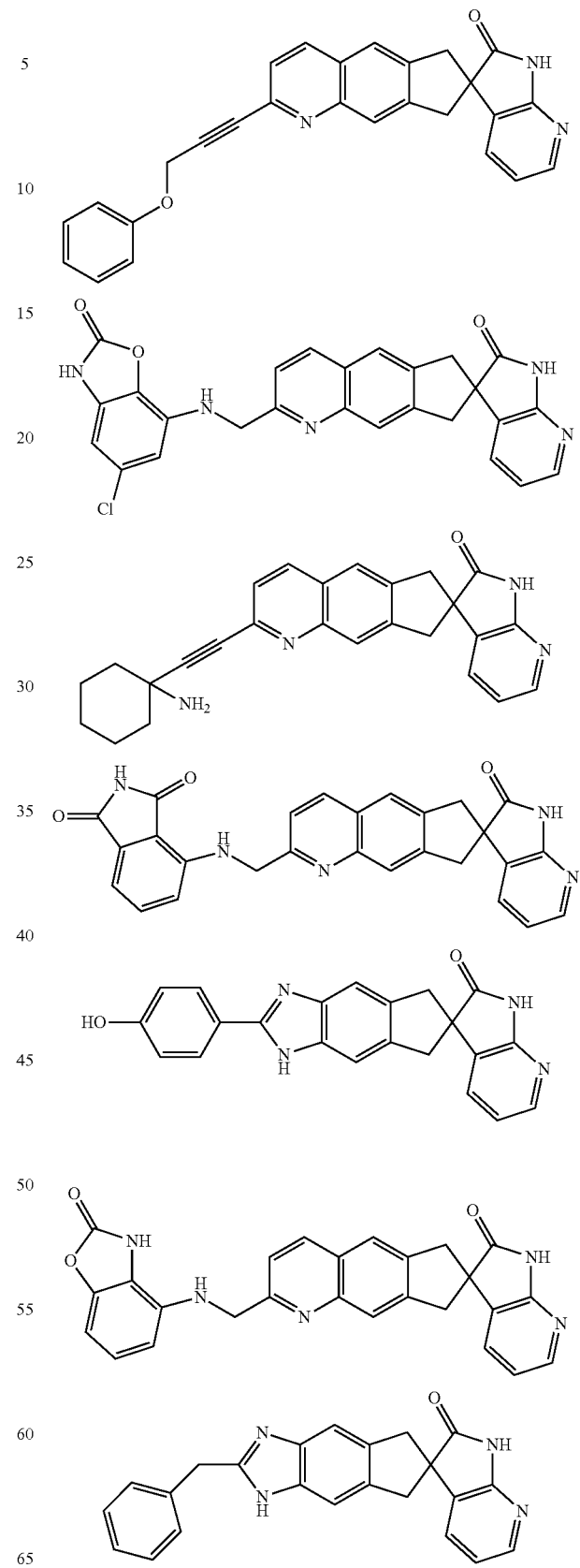

109
-continued
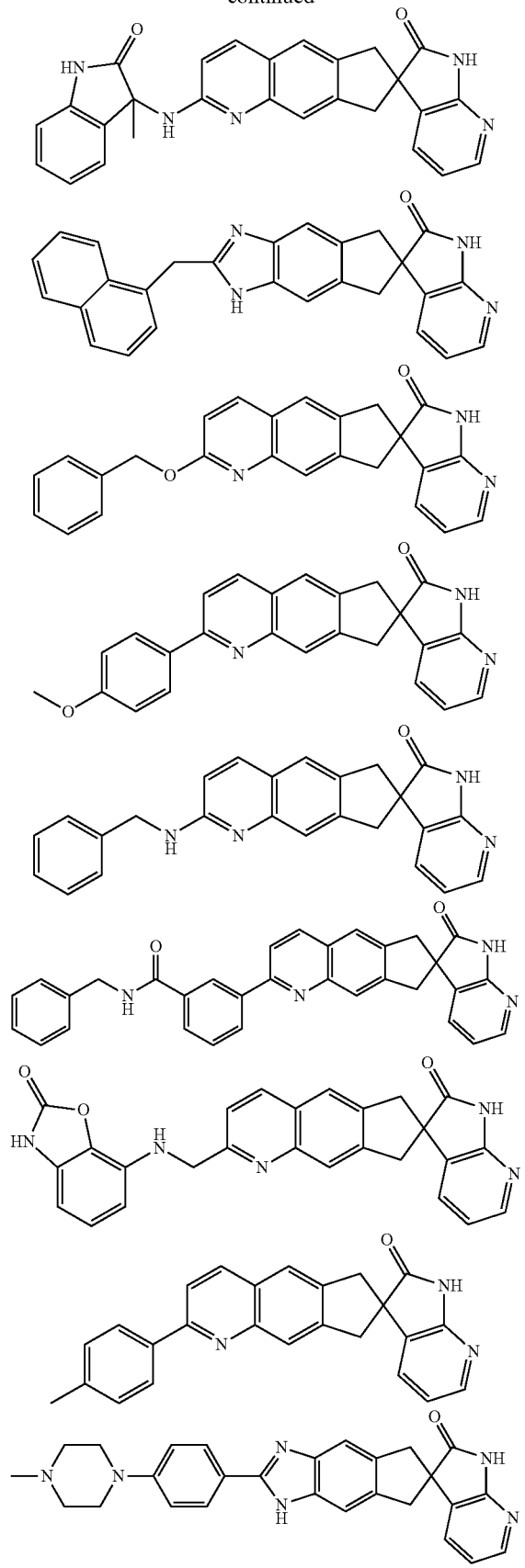
110
-continued
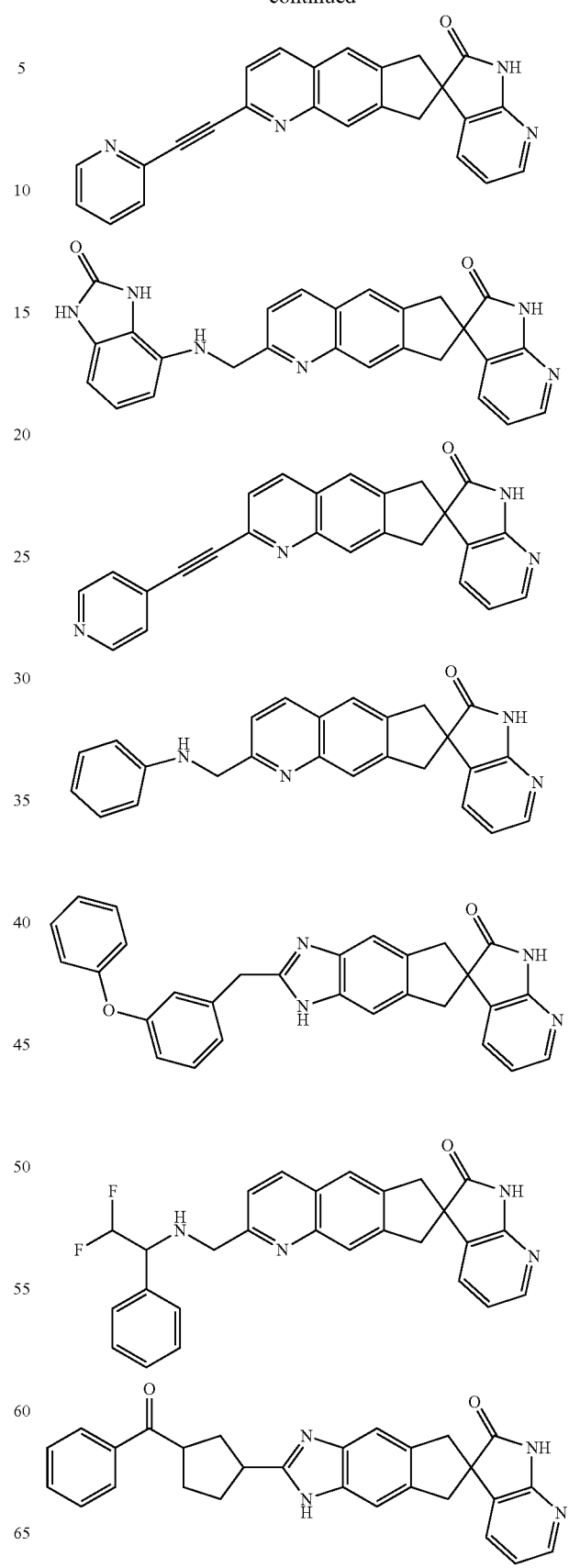

-continued
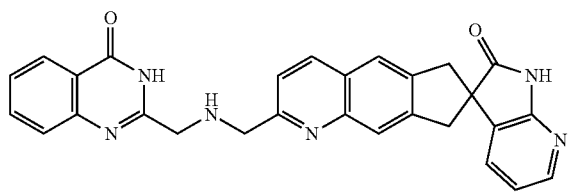
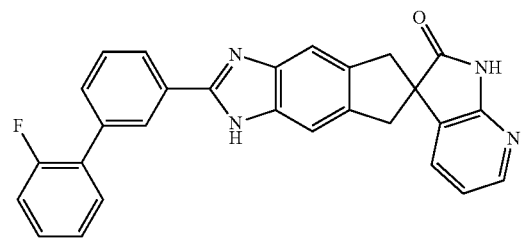
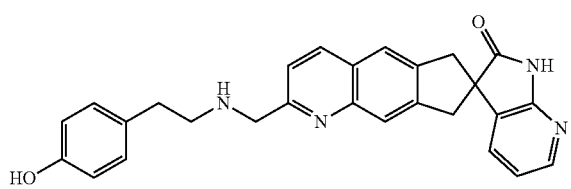
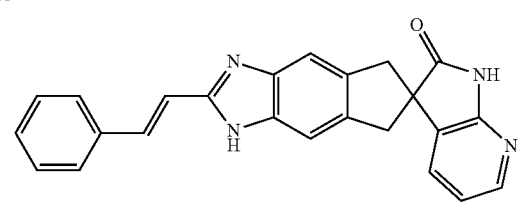
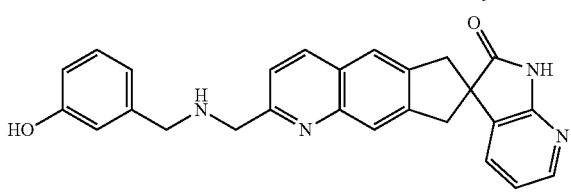
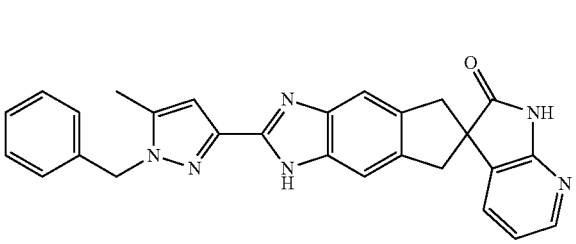
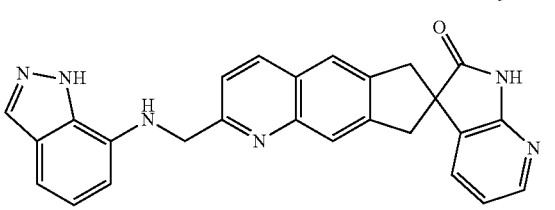
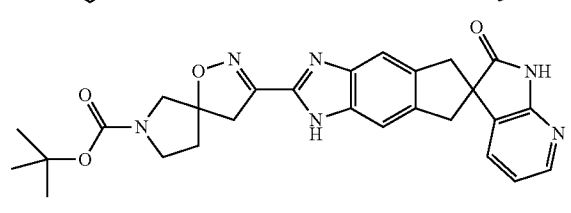
-continued
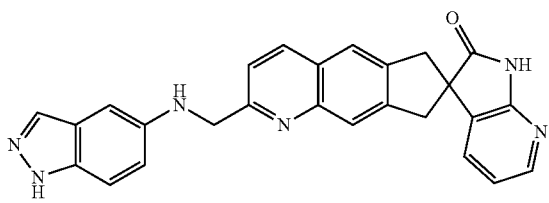
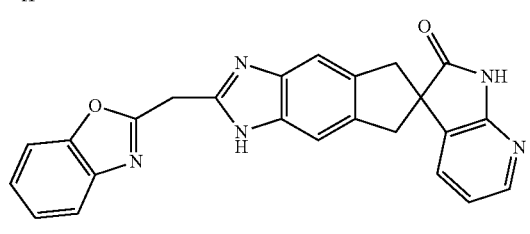
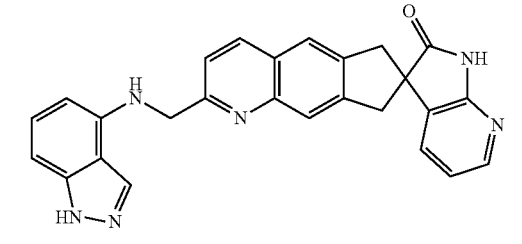
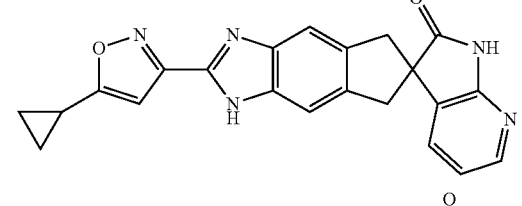
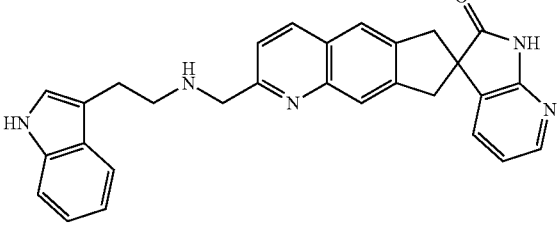
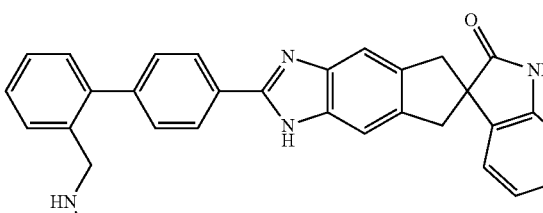
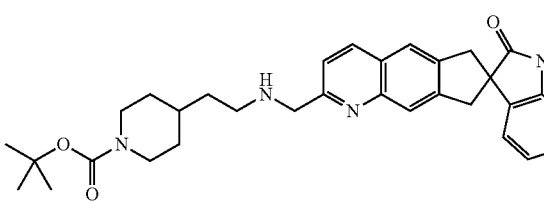

113
-continued
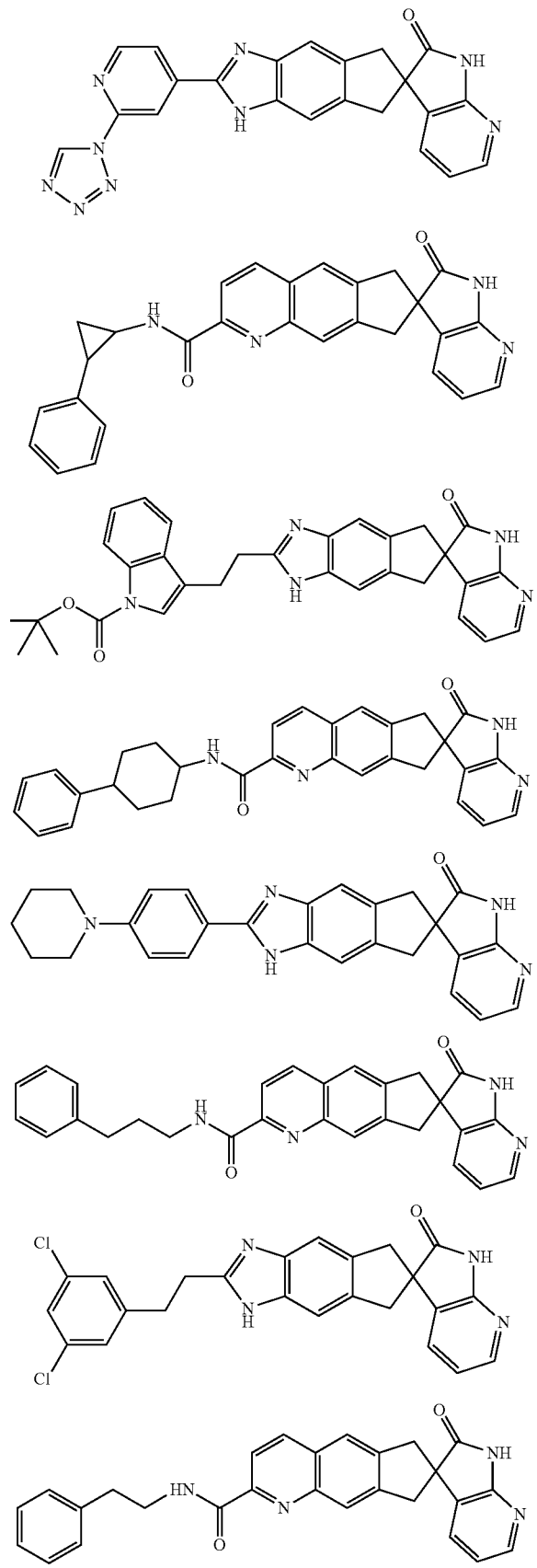
114
-continued
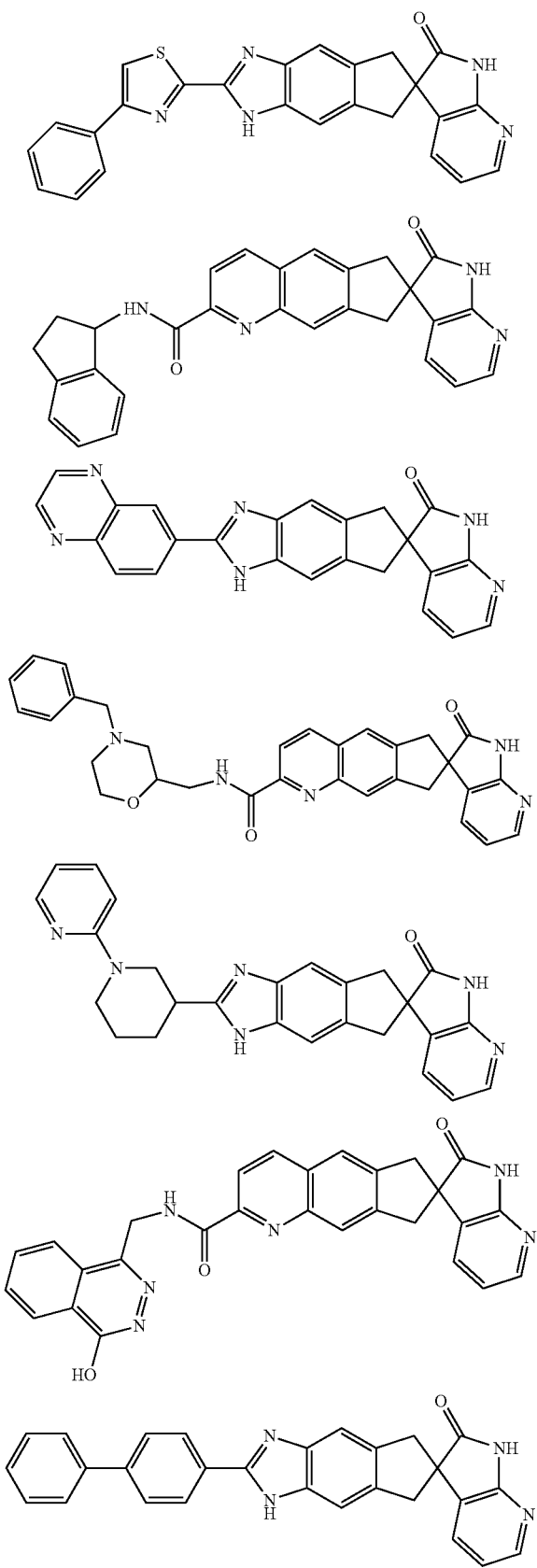

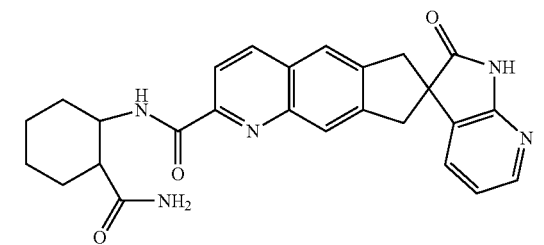
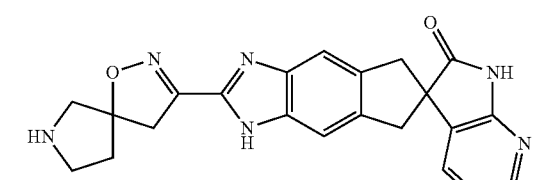
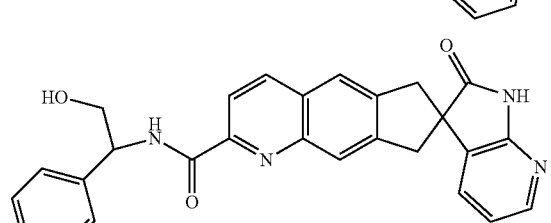
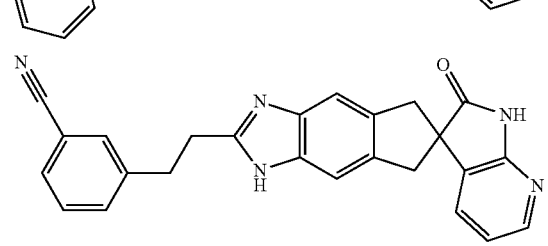
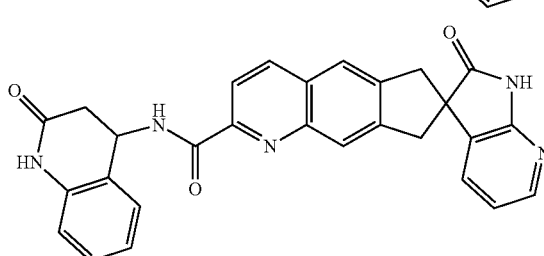
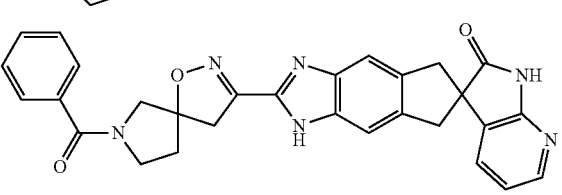
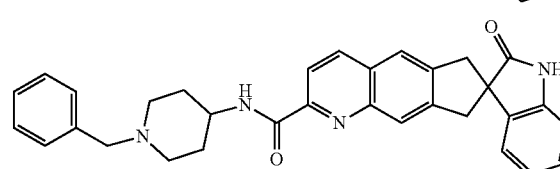
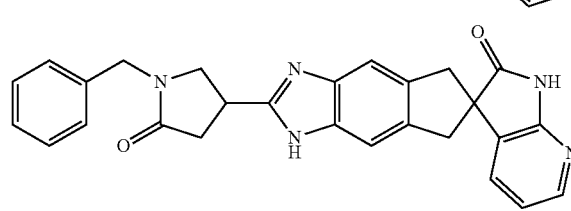
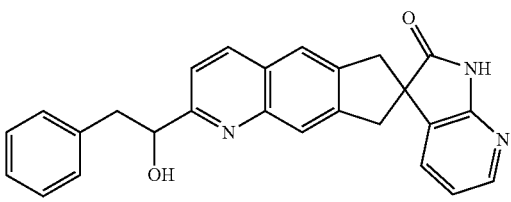
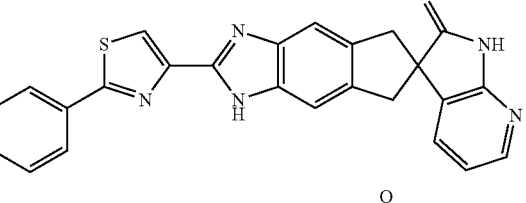
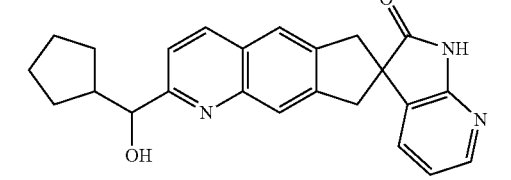
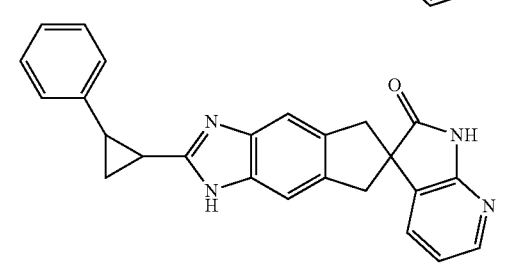
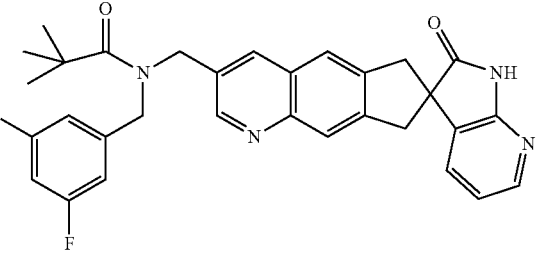
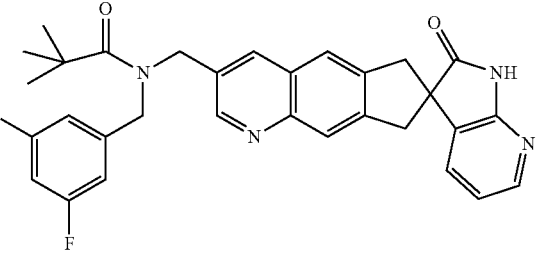
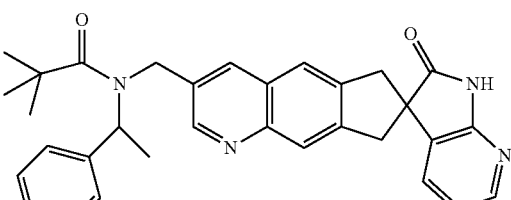
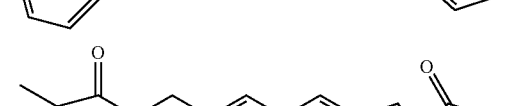
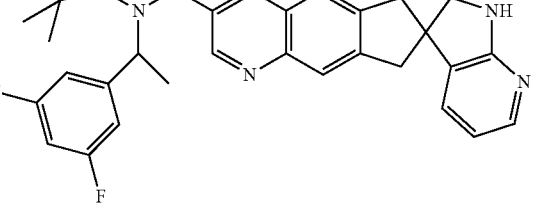

-continued

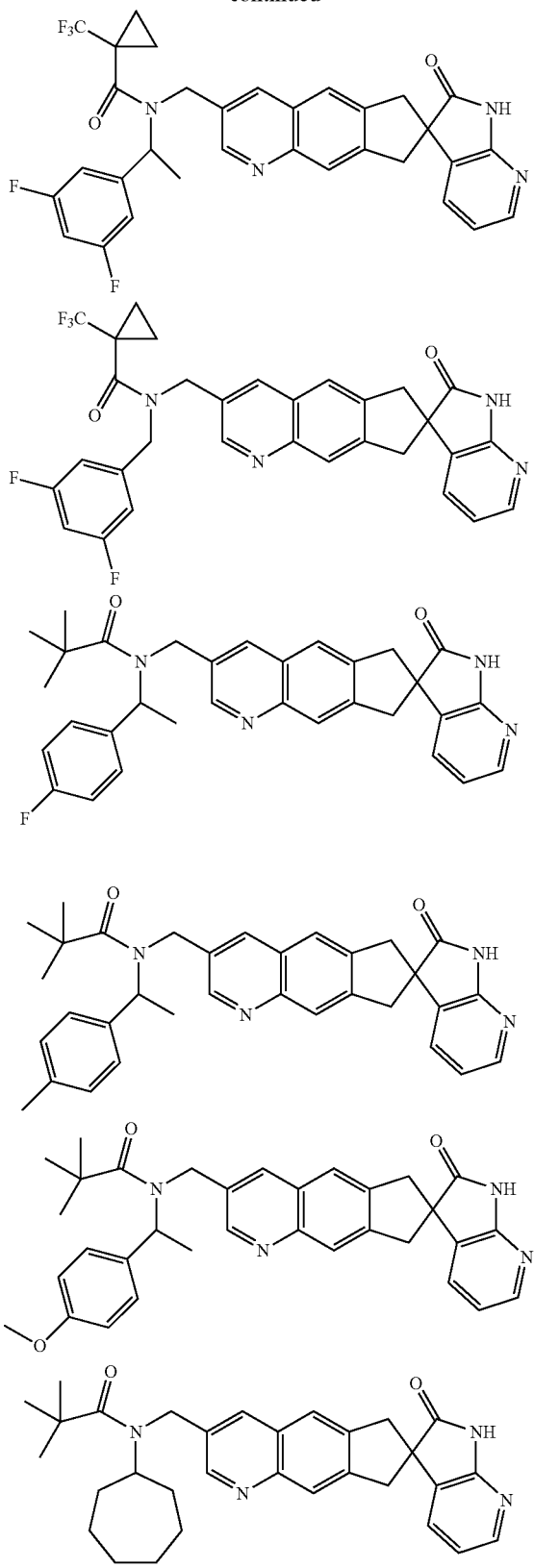

or a pharmaceutically acceptable salt and individual stereoisomers thereof.

10. A pharmaceutical composition which comprises an inert carrier and the compound of claim 1, or a pharmaceutically acceptable salt thereof and individual enantiomers and diastereomers thereof.

11. A method for treating headache in a mammalian patient in need of such which comprises administering to the patient a therapeutically effective amount of the compound of claim 1, or a pharmaceutically acceptable salt thereof and individual enantiomers and diastereomers thereof.

12. The compound according to claim 1 wherein $A^1$ is —$CR^{13}R^{14}$—, $A^2$, $A^3$, $A^4$ and $A^7$ are absent, $A^5$ and $A^6$ are —$CH_2$—, $G^1$ and $G^2$ are =$C(R^4)$—, $E^1$ is =N—, $E^2$ is

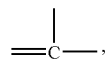

$E^3$ and $E^5$ are =C(H)—, $E^4$ is absent, J is =$C(R^{6a})$—, and K is =$C(R^{6b})$—, where $R^{6a}$ and $R^{6b}$ and the atoms to which they are attached are joined to form a pyridinyl ring, forming the following structure:

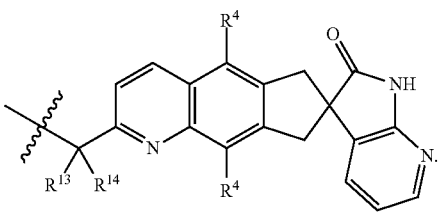

13. The compound according to claim 1 wherein $A^1$ is —$CR^{13}R^{14}$—, $A^2$, $A^3$, $A^4$ and $A^7$ are absent, $A^5$ and $A^6$ are —$CH_2$—, $G^1$ and $G^2$ are =$C(R^4)$—, $E^5$ is =N—, $E^2$ is

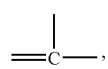

$E^1$ and $E^3$ are =C(H)—, $E^4$ is absent, J is =$C(R^{6a})$—, and K is =$C(R^{6b})$—, where $R^{6a}$ and $R^{6b}$ and the atoms to which they are attached are joined to form a pyridinyl ring, forming the following structure:

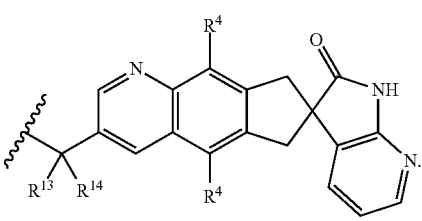

14. The compound according to claim 1 wherein $A^1$ is C(=O)—, $A^2$, $A^3$, $A^4$ and $A^7$ are absent, $A^5$ and $A^6$ are —$CH_2$—, $G^1$ and $G^2$ are =$C(R^4)$—, $E^1$ is =N—, $E^2$ is

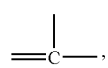

$E^3$ and $E^5$ are =C(H)—, $E^4$ is absent, J is =C($R^{6a}$)—, and K is =C($R^{6b}$)—, where $R^{6a}$ and $R^{6b}$ and the atoms to which they are attached are joined to form a pyridinyl ring, forming the following structure:

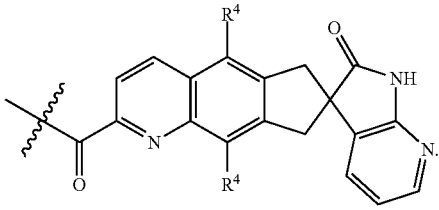

15. The compound according to claim 1 wherein $A^1$ is —$CR^{13}R^{14}$—, $A^2$, $A^3$, $A^4$ and $A^7$ are absent, $A^5$ and $A^6$ are —$CH_2$—, $G^1$ and $G^2$ are =C($R^4$)—, $E^1$ and $e^5$ are =N—, $E^2$ is

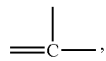

$E^3$ is =C(H)— and $E^4$ is absent, J is =C($R^{6a}$)—, and K is =C($R^{6b}$)—, where $R^{6a}$ and $R^{6b}$ and the atoms to which are attached are joined to form a pyridinyl ring, forming the following structure:

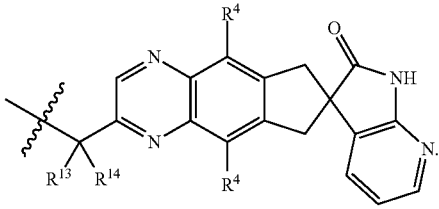

16. The compound according to claim 1 wherein $A^1$ is —$CR^{13}R^{14}$—, $A^2$, $A^3$, $A^4$ and $A^7$ are absent, $A^5$ and $A^6$ are —$CH_2$—, $G^1$ and $G^2$ are =C($R^4$)—, $E^1$ is —N($R^4$)—, $E^2$ is

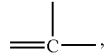

$E^3$ and $E^4$ are absent, $E^5$ is =N—, J is =C($R^{6a}$)—, and K is =C($R^{6b}$)—, where $R^{6a}$ and $R^{6b}$ and the atoms to which they are attached are joined to form a pyridinyl ring, forming the following structure:

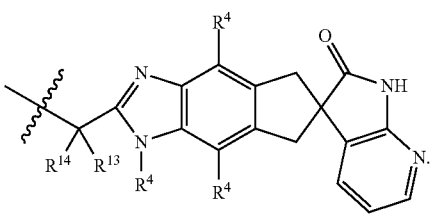

17. The compound according to claim 1 wherein $A^1$ is —$CR^{13}R^{14}$—, $A^2$, $A^3$, $A^4$ and $A^7$ are absent, $A^5$ and $A^6$ are —$CH_2$—, $G^1$ and $G^2$ are =C($R^4$)—, $E^1$ is —N(H)—, $E^2$ is

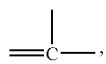

$E^3$ is =N—, $E^4$ and $E^5$ are —$CR^4R^5$—, J is =C($R^{6a}$)—, and K is =C($R^{6b}$)—, where $R^{6a}$ and $R^{6b}$ and the atoms to which they are attached are joined to form a pyridinyl ring, forming the following structure:

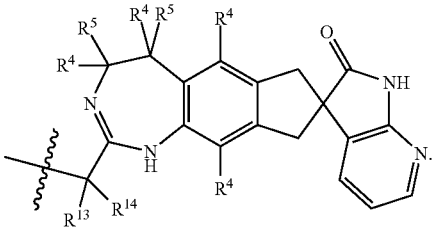

* * * * *

UNITED STATES PATENT AND TRADEMARK OFFICE
CERTIFICATE OF CORRECTION

| | | |
|---|---|---|
| PATENT NO. | : 7,851,464 B2 | Page 1 of 1 |
| APPLICATION NO. | : 12/085057 | |
| DATED | : December 14, 2010 | |
| INVENTOR(S) | : Bell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 158 days.

Signed and Sealed this
Seventh Day of June, 2011

David J. Kappos
*Director of the United States Patent and Trademark Office*